US007005524B2

(12) United States Patent
Aquila et al.

(10) Patent No.: US 7,005,524 B2
(45) Date of Patent: Feb. 28, 2006

(54) METHODS FOR THE STEREOSELECTIVE SYNTHESIS OF SUBSTITUTED PIPERIDINES

(75) Inventors: Brian M. Aquila, Marlborough, MA (US); Thomas D. Bannister, Northborough, MA (US); Gregory D. Cuny, Somerville, MA (US); James R. Hauske, Concord, MA (US); Michelle L. R. Heffernan, Worcester, MA (US); Michael Z. Hoemann, Marlborough, MA (US); Donald W. Kessler, Groton, MA (US); Liming Shao, Lincoln, MA (US); Xinhe Wu, Shrewsbury, MA (US); Roger L. Xie, Natick, MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

(21) Appl. No.: 10/789,414

(22) Filed: Feb. 27, 2004

(65) Prior Publication Data
US 2004/0235893 A1 Nov. 25, 2004

Related U.S. Application Data

(62) Division of application No. 10/012,242, filed on Dec. 4, 2001, now Pat. No. 6,703,508.

(60) Provisional application No. 60/275,600, filed on Mar. 13, 2001, provisional application No. 60/251,209, filed on Dec. 4, 2000.

(51) Int. Cl.
C07D 211/26 (2006.01)
A61K 31/445 (2006.01)

(52) U.S. Cl. ...................... 546/246; 514/331
(58) Field of Classification Search ............... 546/246; 514/331
See application file for complete search history.

(56) References Cited

U.S. PATENT DOCUMENTS

| 4,012,396 | A | 3/1977 | Grethe et al. ........... 260/293.77 |
| 5,013,842 | A | 5/1991 | Fleet et al. ................. 546/220 |
| 5,332,817 | A | 7/1994 | Desai et al. .................. 546/16 |
| 5,420,283 | A | 5/1995 | Dugger ........................ 546/223 |
| 5,952,506 | A | 9/1999 | Jirkovsky .................... 546/221 |
| 5,972,952 | A | 10/1999 | Kamenka et al. ........... 514/279 |

FOREIGN PATENT DOCUMENTS

| EP | 0 406 124 A1 | 1/1991 |
| WO | WO 99/56699 | 11/1999 |
| WO | WO 00/71518 A2 | 11/2000 |
| WO | WO 01/92226 A1 | 12/2001 |

OTHER PUBLICATIONS

International Search Report Mailed on Jul. 5, 2002.
Pu and Yu; "Catalytic Asymmetric Organozinc Additions to Carbonyl Compounds", Chem. Rev. 101: 757-824, (2001).
Seebach et al.; "Enantio-and Diastereoselective Titanium-TADDOLate Catalyzed Addition of Diethyl and bis (3-Buten-1-yl) Zinc to Aldehydes a Full Account with Preparative Details [1,2]", Tetrahedron 50(15): 4363-4384, (1994).

Primary Examiner—Rita Desai
(74) Attorney, Agent, or Firm—Dana M. Gordon; Foley Hoag LLP

(57) ABSTRACT

One aspect of the present invention relates to methods of synthesizing substituted piperidines. A second aspect of the present invention relates to stereoselective methods of synthesizing substituted piperidines. The methods of the present invention will find use in the synthesis of compounds useful for treatment of numerous ailments, conditions and diseases that afflict mammals, including but not limited to addiction and pain. An additional aspect of the present invention relates to the synthesis of combinatorial libraries of the substituted piperidines using the methods of the present invention. An additional aspect of the present invention relates to enantiomerically substituted pyrrolidines, piperidines, and azepines.

28 Claims, 41 Drawing Sheets

Examples of Substituted Piperidines Accessible Via
the Methods of the Present Invention Structure A    Structure B Structure C    Structure D For Structures A, B, C, and D:

n = 0, 1, or 2
$R_1$ = H, alkyl, aryl, heteroaryl, aralkyl, -$CO_2R_4$, or -C(O)NH$R_4$
$R_2$ = alkyl
X = O, NC(O)$R_4$, or NS(O)$_2R_4$, NH, N$R_4$, S, or S(O)
$R_3$ = alkyl, aralkyl, aryl, or heteroaryl
$R_4$ = alkyl, aryl, heteroaryl, or aralkyl Figure 1
Examples of Substituted Piperidines Accessible Via
the Methods of the Present Invention
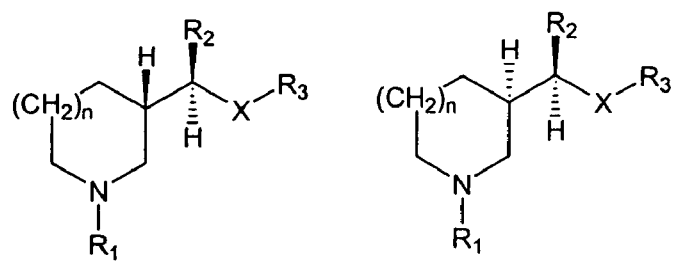
Structure A        Structure B
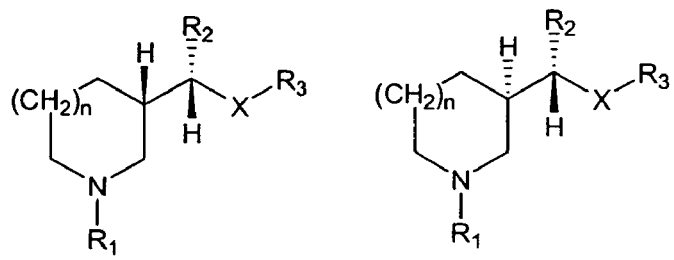
Structure C        Structure D
*For Structures A, B, C, and D:*
n = 0, 1, or 2
$R_1$ = H, alkyl, aryl, heteroaryl, aralkyl, -$CO_2R_4$, or -$C(O)NHR_4$
$R_2$ = alkyl
X = O, $NC(O)R_4$, or $NS(O)_2R_4$, NH, $NR_4$, S, or S(O)
$R_3$ = alkyl, aralkyl, aryl, or heteroaryl
$R_4$ = alkyl, aryl, heteroaryl, or aralkyl Prophetic Asymmetric Synthesis of 3-Substituted Piperidine 1

Prophetic Asymmetric Synthesis of 50

Prophetic Asymmetric Syntheses of 3-Substituted Piperidine 1

Figure 5
Prophetic Asymmetric Synthesis of 3-Substituted Piperidine 3
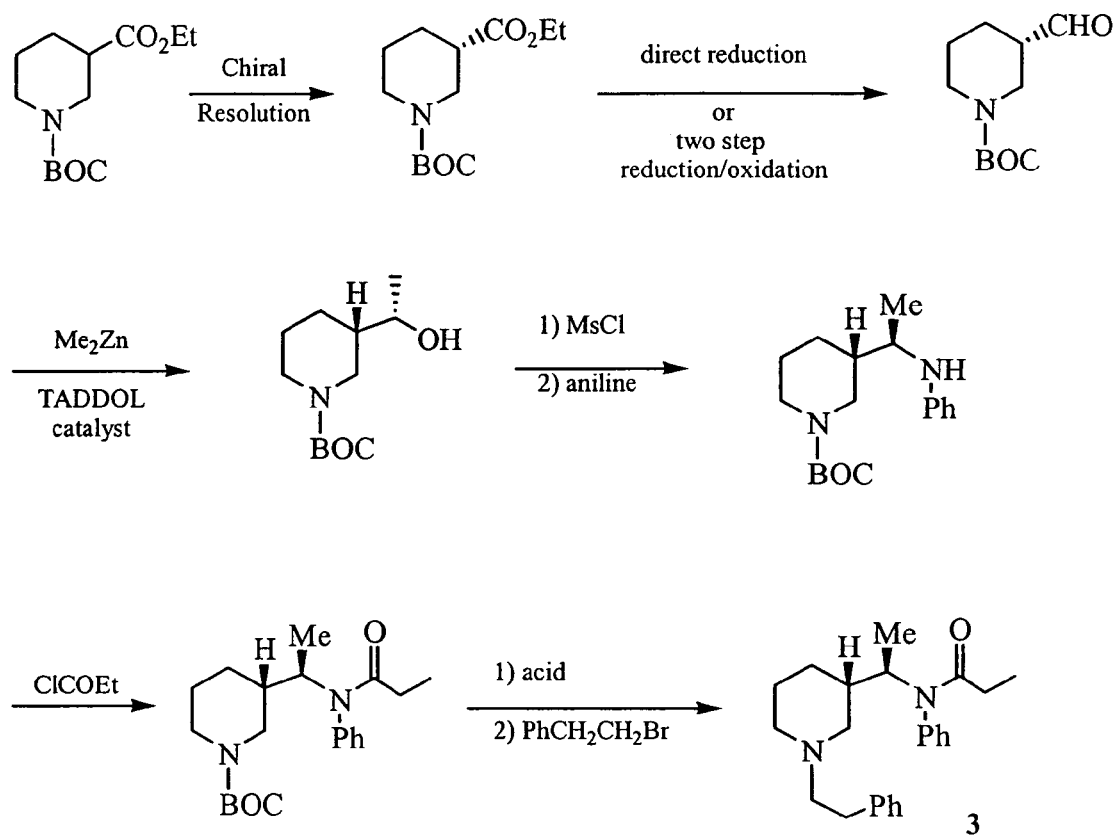
*TADDOL catalysts*
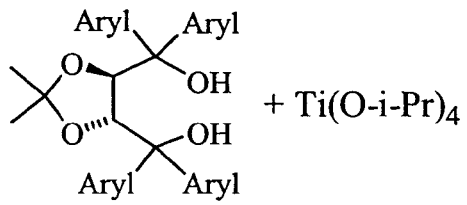
Aryl = Ph,
2-napthyl, or 1-napthyl
*Both enantiomers are commercially available*

Figure 6
Prophetic Asymmetric Synthesis of 3-Substituted Piperidine 51
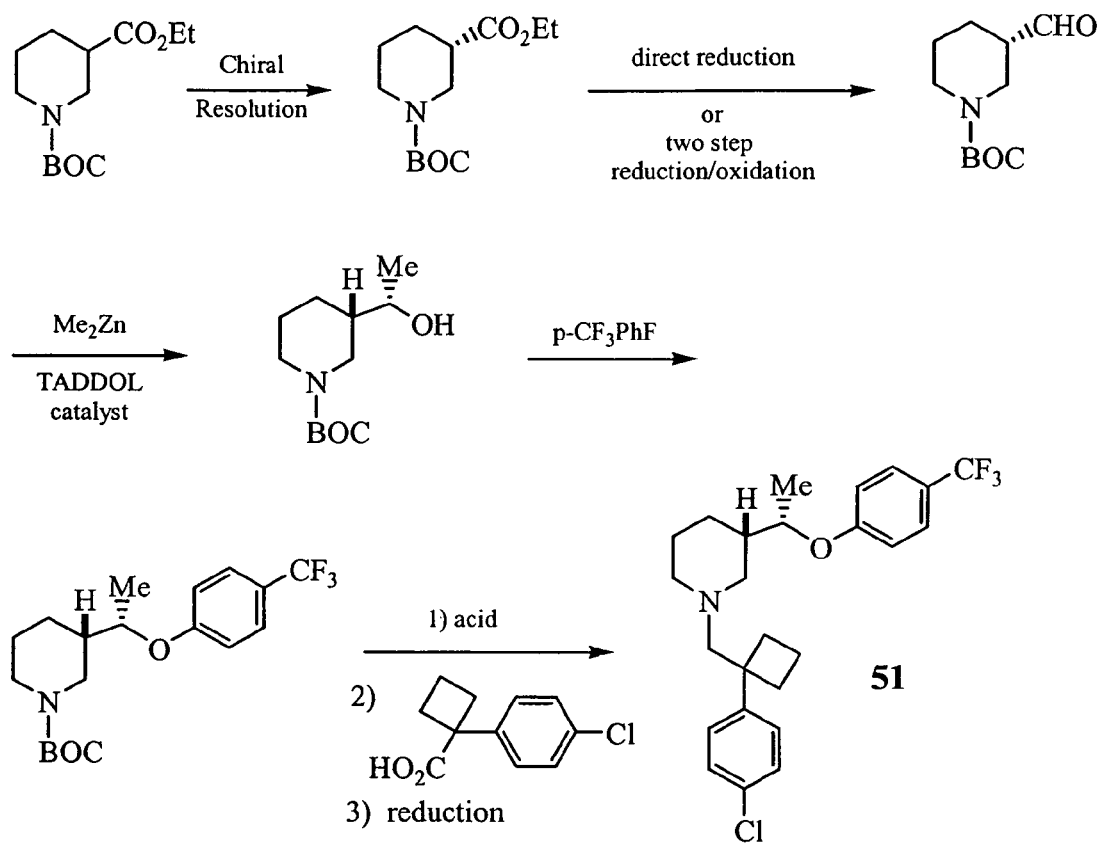
TADDOL catalysts
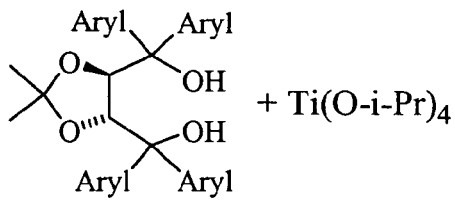
Aryl = Ph,
2-napthyl, or 1-napthyl
Both enantiomers are
commercially available
+ Ti(O-i-Pr)$_4$

*Mixture of 15, 16, 27, and 28*

*15: (R,S)-Isomer Chromatogram*

27: (S,S)-Isomer Chromatogram

*16: (R,R)-Isomer Chromatogram*

*28: (S,R)-Isomer Chromatogram*

Figure 16

| No. | Description of HPLC Trace | Peak Retention Times (min) |
|---|---|---|
| 1 | Catalyst 13 (254 nm) | 8.420, 8.781 |
| 2 | Catalyst 13 (220 nm) | 8.420, 8.781 |
| 3 | Catalyst 13 and non-selective coinjection (254 nm) | 8.155, 8.328, 8.695 |
| 4 | Catalyst 13 and non-selective coinjection (220 nm) | 8.155, 8.333, 8.688 |
| 5 | non-selective (254 nm) | 8.208, 8.395, 8.688 |
| 6 | Catalyst 14 (254 nm) | 8.061, 8.210, 8.399, 8.688, 8.897 |

Figure 17

| No. | Description of HPLC Trace | Peak Retention Times (min) |
|---|---|---|
| 1 | Catalyst 14 (254 nm) | 8.158, 8.423 |
| 2 | Catalyst 14 (220 nm) | 8.030, 8.159, 8.366 |
| 3 | Catalyst 14 and non-selective coinjection (254 nm) | 8.176, 8.386, 8.664 |
| 4 | Catalyst 14 and non-selective coinjection (220 nm) | 8.044, 8.178, 8.387 |
| 5 | non-selective (254 nm) | 8.176, 8.374, 8.646, 9.950 |
| 6 | non-selective (220 nm) | 8.375 |

Figure 18

| No. | Description of HPLC Trace | Peak Retention Times (min) |
|---|---|---|
| 1 | Catalyst 13 (254 nm) | 8.42 |
| 2 | Catalyst 13 (220 nm) | 8.420, 8.781 |
| 3 | Catalyst 13 and Catalyst 14 coinjection (254 nm) | 8.147, 8.337, 8.695 |
| 4 | Catalyst 13 and Catalyst 14 coinjection (220 nm) | 8.147, 8.338, 8.695 |
| 5 | Catalyst 14 (254 nm) | 8.158, 8.423 |
| 6 | Catalyst 14 (220 nm) | 8.030, 8.159, 8.366 |

Figure 20
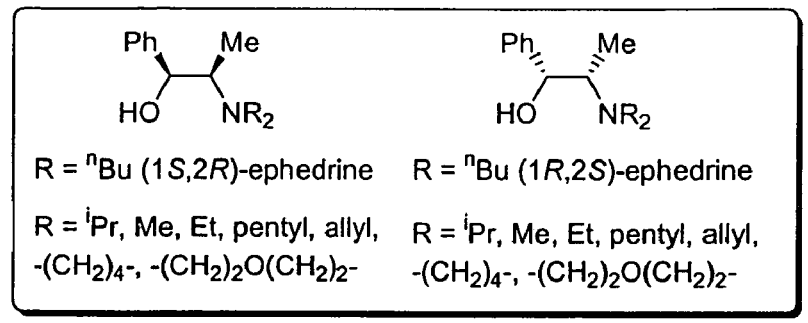
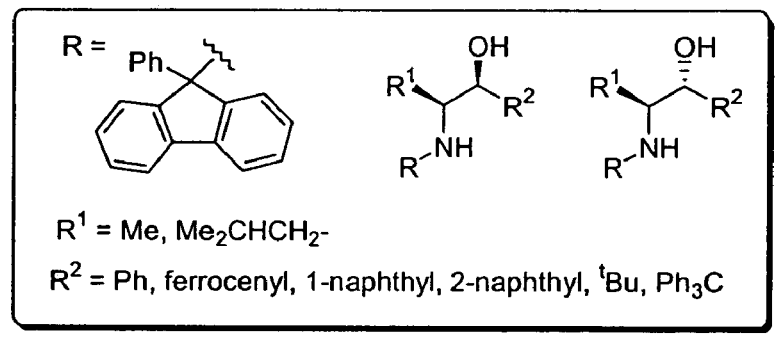
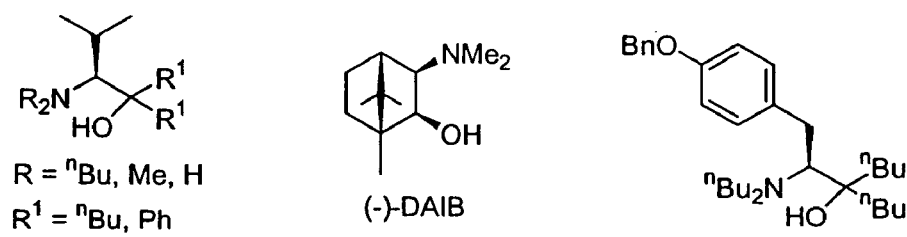
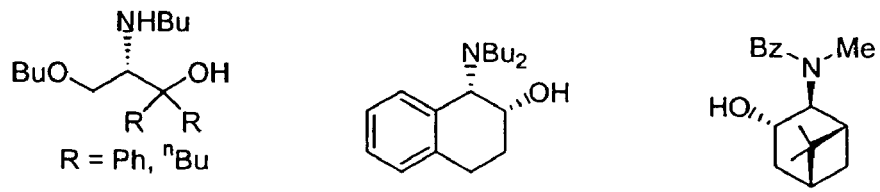

Figure 23
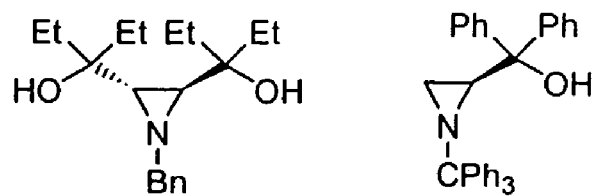
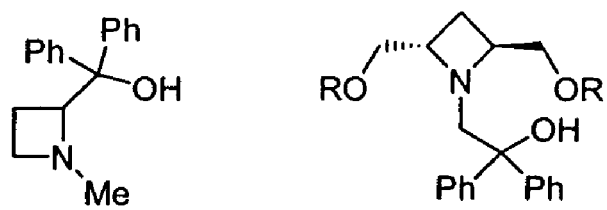
R = Me, TBDMS, TBDPS
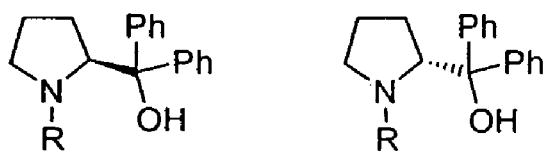
R = Me, H, -CH$_2$CMe$_3$
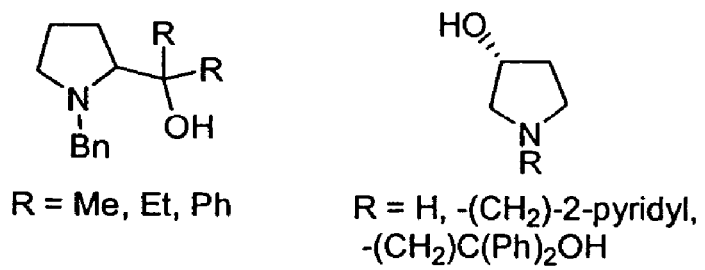
R = Me, Et, Ph          R = H, -(CH$_2$)-2-pyridyl,
                         -(CH$_2$)C(Ph)$_2$OH Figure 25
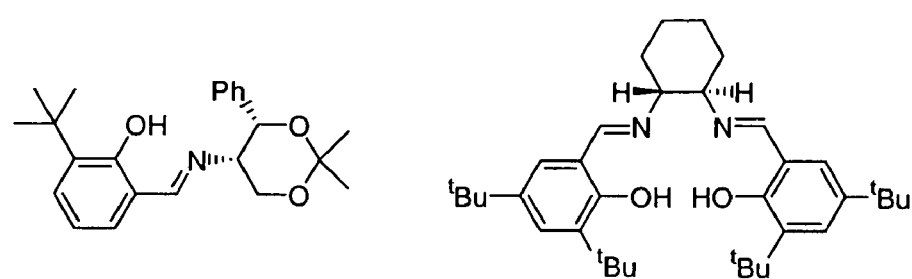
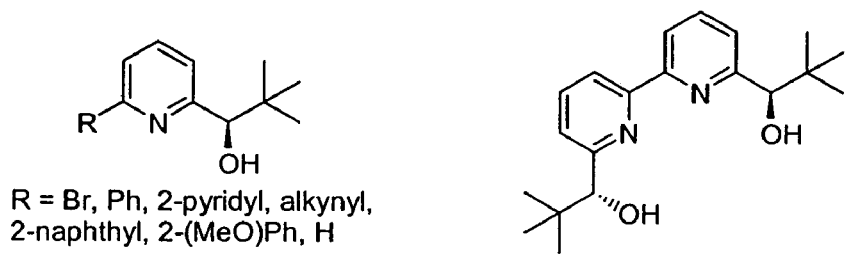
R = Br, Ph, 2-pyridyl, alkynyl,
2-naphthyl, 2-(MeO)Ph, H
Ar = Ph, 1-naphthyl,
2-naphthyl
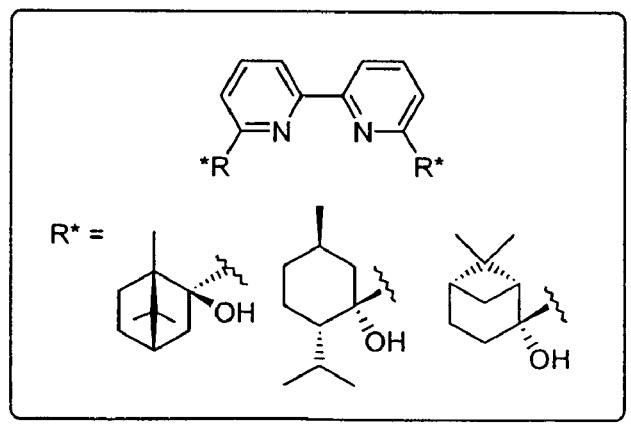
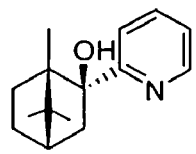

Figure 29
Aminoalcohols
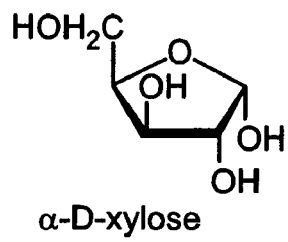
α-D-xylose
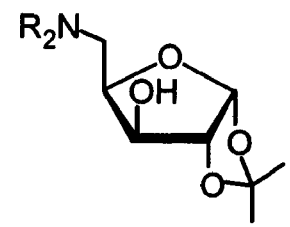
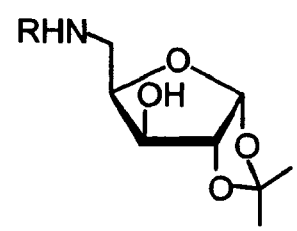
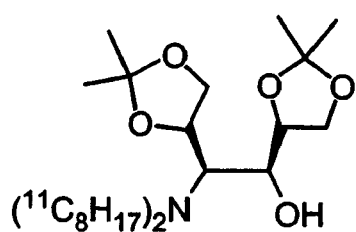
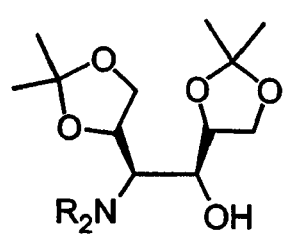
R = $^nBu$, -(CH$_2$)$_4$-,
-(CH$_2$)$_5$-, -(CH$_2$)$_6$-
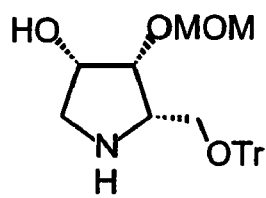
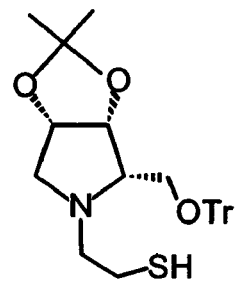
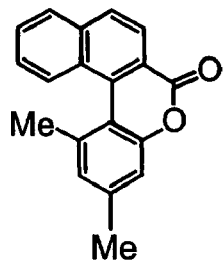
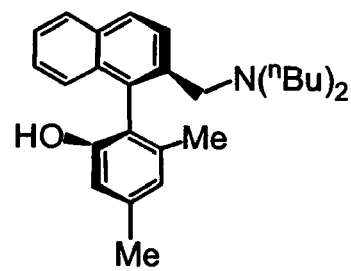
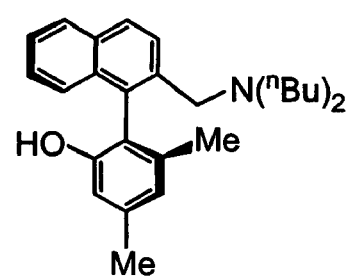
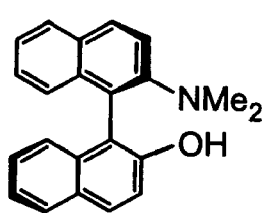
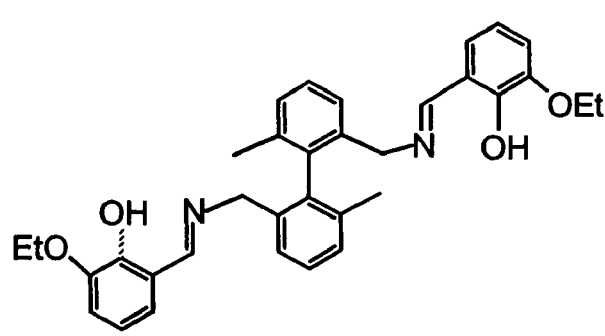

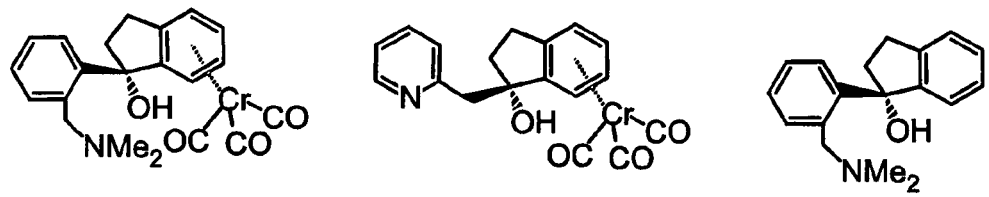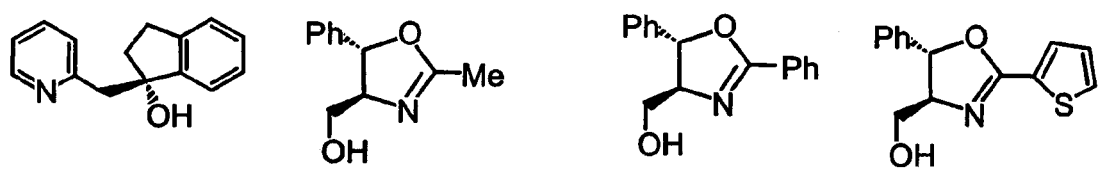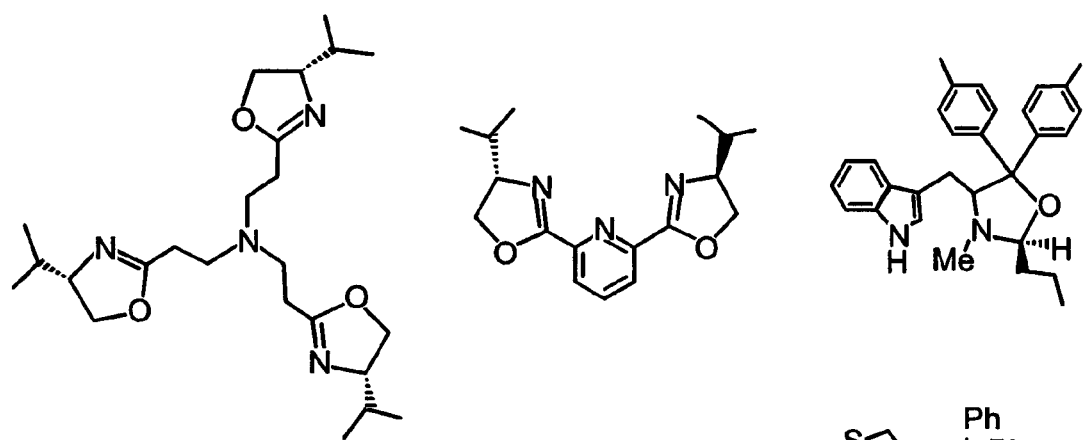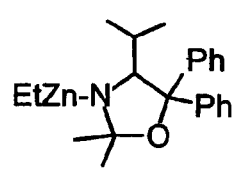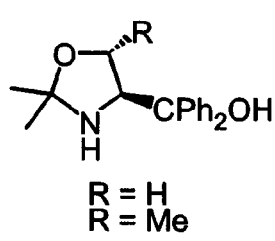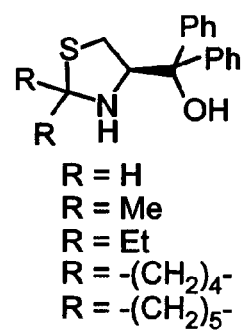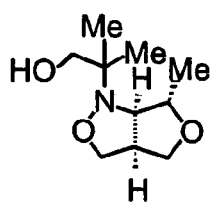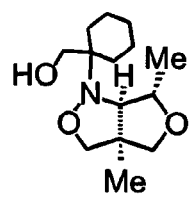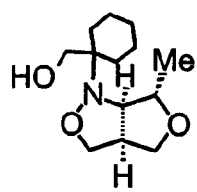
Figure 31

Figure 32
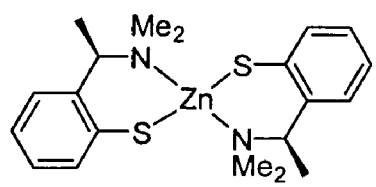 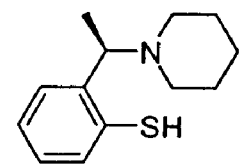
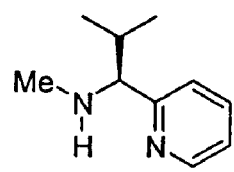 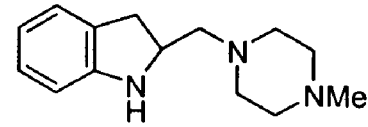
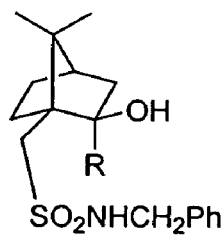
R = H, Me
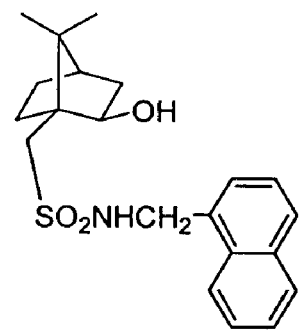
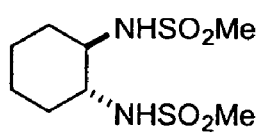 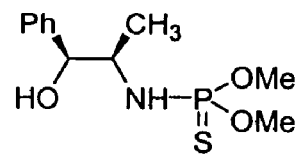

Figure 33

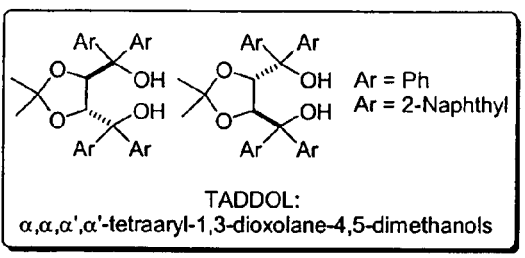

TADDOL:
α,α,α',α'-tetraaryl-1,3-dioxolane-4,5-dimethanols

Ar = Ph
Ar = 2-Naphthyl

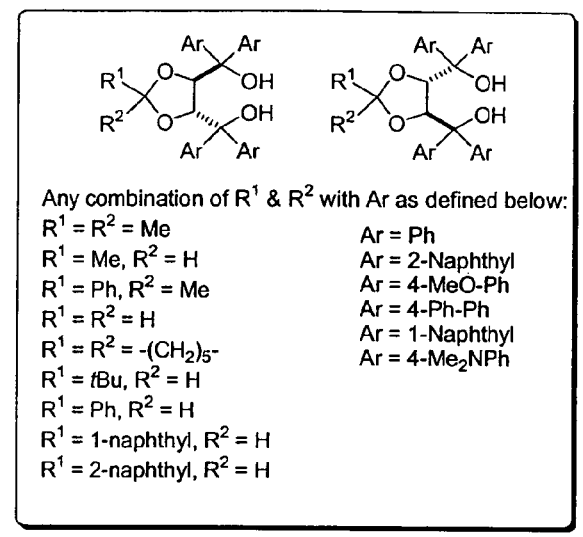

Any combination of $R^1$ & $R^2$ with Ar as defined below:
$R^1 = R^2 = Me$
$R^1 = Me, R^2 = H$
$R^1 = Ph, R^2 = Me$
$R^1 = R^2 = H$
$R^1 = R^2 = -(CH_2)_5-$
$R^1 = tBu, R^2 = H$
$R^1 = Ph, R^2 = H$
$R^1 = $ 1-naphthyl, $R^2 = H$
$R^1 = $ 2-naphthyl, $R^2 = H$ Ar = Ph
Ar = 2-Naphthyl
Ar = 4-MeO-Ph
Ar = 4-Ph-Ph
Ar = 1-Naphthyl
Ar = 4-Me$_2$NPh

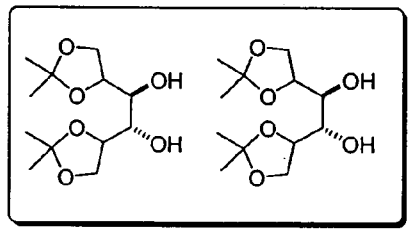

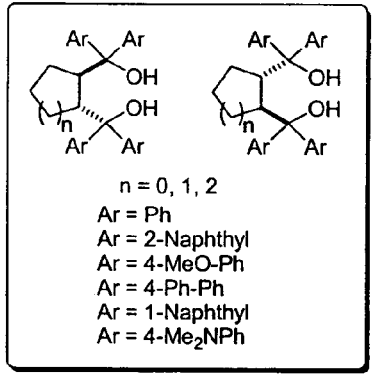

n = 0, 1, 2
Ar = Ph
Ar = 2-Naphthyl
Ar = 4-MeO-Ph
Ar = 4-Ph-Ph
Ar = 1-Naphthyl
Ar = 4-Me$_2$NPh

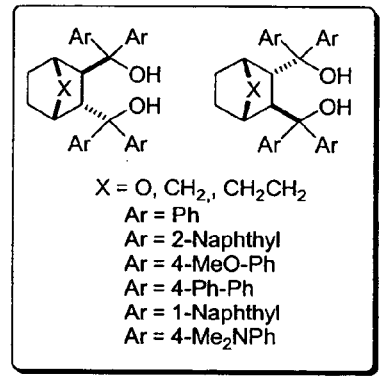

X = O, CH$_2$, CH$_2$CH$_2$
Ar = Ph
Ar = 2-Naphthyl
Ar = 4-MeO-Ph
Ar = 4-Ph-Ph
Ar = 1-Naphthyl
Ar = 4-Me$_2$NPh

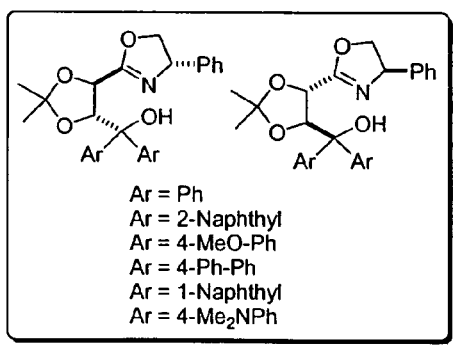

Ar = Ph
Ar = 2-Naphthyl
Ar = 4-MeO-Ph
Ar = 4-Ph-Ph
Ar = 1-Naphthyl
Ar = 4-Me$_2$NPh

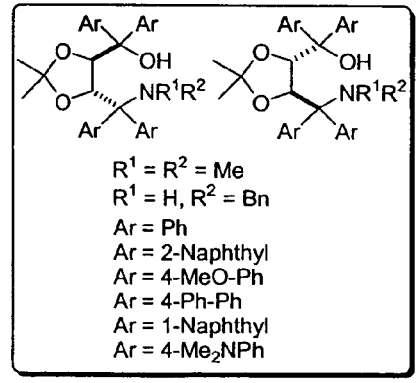

$R^1 = R^2 = Me$
$R^1 = H, R^2 = Bn$
Ar = Ph
Ar = 2-Naphthyl
Ar = 4-MeO-Ph
Ar = 4-Ph-Ph
Ar = 1-Naphthyl
Ar = 4-Me$_2$NPh ● = an organic polymer or inorganic solid support

*Mixture of 1, 2, 3 and 4:*

*2: (R,S)-Isomer Chromatogram*

METHODS FOR THE STEREOSELECTIVE SYNTHESIS OF SUBSTITUTED PIPERIDINES

RELATED APPLICATIONS

This application is a divisional of U.S. patent application Ser. No. 10/012,242, filed Dec. 4, 2001, now U.S. Pat. No. 6,703,508; which claims the benefit of priority to U.S. Provisional Patent Applications Ser. Nos. 60/251,209, filed Dec. 4, 2000; and 60/275,600, filed Mar. 13, 2001.

BACKGROUND OF THE INVENTION

Pain is an unpleasant sensation varying in severity in a local part of the body or several parts of the body resulting from injury, disease, or emotional disorder. Pain can be classified according to its duration. Acute pain, which lasts less than one month, usually has a readily identifiable cause and signals tissue damage. In addition, acute pain syndromes can be episodic, for example recurrent discomfort from arthritis. Chronic pain can be defined as pain that persists more than one month beyond the usual course of an acute illness or injury, or pain that recurs at intervals over months or years, or pain that is associated with a chronic pathologic process. In contrast to acute pain, chronic pain loses its adaptive biologic function. Depression is common, and abnormal illness behavior often compounds the patient's impairment.

Millions of people suffer from chronic or intractable pain. Persistent pain varies in etiology and presentation. In some cases, symptoms and signs may be evident within a few weeks to a few months after the occurrence of an injury or the onset of disease, e.g. cancer or AIDS. Like many illnesses that at one time were not well understood, pain and its many manifestations may be poorly treated and seriously underestimated. Inappropriately treated pain seriously compromises the patient's quality of life, causing emotional suffering and increasing the risk of lost livelihood and disrupted social integration. Severe chronic pain affects both the pediatric and adult population, and often leads to mood disorders, including depression and, in rare cases, suicide.

In the last several years, health policy-makers, health professionals, regulators, and the public have become increasingly interested in the provision of better pain therapies. This interest is evidenced, in part, by the U.S. Department of Health and Human Services' dissemination of Clinical Practice Guidelines for the management of acute pain and cancer pain. There is currently no nationally accepted consensus for the treatment of chronic pain not due to cancer, yet the economic and social costs of chronic pain are substantial, with estimates ranging in the tens of billions of dollars annually.

Three general classes of drugs are currently available for pain management, nonsteriodal anti-inflammatories, opioidids, and adjuvant analgesics. The nonsteriodal anti-inflammatories class includes drugs such as aspirin, ibuprofen, diclofenac, acetaminophen, celecoxib, and rofecoxib. The opioid class includes morphine, oxycodone, fentanyl, and pentazocine. Adjuvant analgesics include various antidepressants, anticonvulsants, neuroleptics, and corticosteroids.

Opioids are the major class of analgesics used in the management of moderate to severe pain because of their effectiveness, ease of titration, and favorable risk-to-benefit ratio. Opioids produce analgesia by binding to specific receptors both within and outside the CNS. Opioid analgesics are classified as full agonists, partial agonists, or mixed agonist-antagonists, depending on the receptors to which they bind and their intrinsic activities at each receptor.

Three subclasses of opioid receptor have been identified in humans, namely the δ-, κ-, and μ-opioid receptors. Analgesia is thought to involve activation of μ and/or κ receptors. Notwithstanding their low selectivity for μ over κ receptors, it is likely that morphine and morphine-like opioid agonists produce analgesia primarily through interaction with μ receptors; selective agonists of κ receptors in humans produce analgesia, because rather than the euphoria associated with morphine and congeners, these compounds often produce dysphoria and psychotomimetic effects. The consequences of activating δ receptors in humans remain unclear.

Although opioids can be very effective in pain management, they do cause several side effects, such as respiratory depression, constipation, physical dependence, tolerance, and withdrawal. These unwanted effects can severely limit their use.

Opioids are known to produce respiratory depression that is proportional to their analgesia. This respiratory depression can be life threatening. This results in a narrow range between the effective dose and a dose that produces respiratory depression. Because of this narrow therapeutic index, patients receiving opioid therapy must be closely monitored for signs of respiratory failure.

Opioids can also cause constipation in individuals receiving them. This side effect can be severe and may require prolonged hospitalization, or even surgical intervention.

Commonly used full agonists include morphine, hydromorphone, meperidine, methadone, levorphanol, and fentanyl. These opioids are classified as full agonists because there is not a ceiling to their analgesic efficacy, nor will they reverse or antagonize the effects of other opioids within this class when given simultaneously. Side effects include respiratory depression, constipation, nausea, urinary retention, confusion, and sedation. Morphine is the most commonly used opioid for moderate to severe pain because of its availability in a wide variety of dosage forms, its well-characterized pharmacokinetics and pharmacodynamics, and its relatively low cost. Meperidine may be useful for brief courses (e.g., a few days) to treat acute pain and to manage rigors (shivering) induced by medication, but it generally should be avoided in patients with cancer because of its short duration of action (2.5 to 3.5 hours) and its toxic metabolite, normeperidine. This metabolite accumulates, particularly when renal function is impaired, and causes CNS stimulation, which may lead to dysphoria, agitation, and seizures; meperidine, therefore, should not be used if continued opioid use is anticipated.

The development of physical dependence with repeated use is a characteristic feature of the opioid drugs, and the possibility of developing drug dependence is one of the major limitations of their clinical use. Almost all opioid users rapidly develop drug dependency which can lead to apathy, weight loss, loss of sex drive, anxiety, insomnia, and drug cravings. Although physical dependence is common, addiction and abuse are not common in pain patients who are treated appropriately with opioid drugs.

Historically, the development of analgesic tolerance was believed to limit the ability to use opioids efficaciously on a long-term basis for pain management. Tolerance, or decreasing pain relief with the same dosage over time, has not proven to be a prevalent limitation to long-term opioid use. Experience with treating cancer pain has shown that what initially appears to be tolerance is usually progression of the disease. Furthermore, for most opioids, there does not appear to be an arbitrary upper dosage limit, as was once thought.

Cessation of opioid administration may result in a withdrawal syndrome. Symptoms of withdrawal are often the opposite of the effects achieved by the drug; withdrawal from morphine, however, results in complex symptoms that may seem unrelated to its effects. Misunderstanding of addiction and mislabeling of patients as addicts result in unnecessary withholding of opioid medications. Addiction is a compulsive disorder in which an individual becomes preoccupied with obtaining and using a substance, the continued use of which results in a decreased quality of life. Studies indicate that the de novo development of addiction is low when opioids are used for the relief of pain. Furthermore, even opioid addicts can benefit from the carefully supervised, judicious use of opioids for the treatment of pain due to cancer, surgery, or recurrent painful illnesses such as sickle cell disease.

The known opioids have been very effective in pain management. However, they have restricted use because of several potentially severe side effects. Therefore, there is a current need for pharmaceutical agents that retain the analgesic properties of the known opioid, but that have reduced side effect profiles.

Additionally, dopamine, norepinephrine and serotonin are mammalian monoamine neurotransmitters that play important roles in a wide variety of physiological processes. Therefore, compounds that selectively modulate the activity of these three neurotransmitters, either individually, in pairs, or as a group, promise to serve as agents effective in the treatment of a wide range of maladies, conditions and diseases that afflict mammals due to atypical activities of these neurotransmitters. Interestingly, a significant portion of the known compounds that modulate the activity of these three neurotransmitters, either individually, in pairs, or as a group, comprise a substituted piperidine moiety.

Dopamine plays a major role in addiction. Many of the concepts that apply to dopamine apply to other neurotransmitters as well. As a chemical messenger, dopamine is similar to adrenaline. Dopamine affects brain processes that control movement, emotional response, and ability to experience pleasure and pain. Regulation of dopamine plays a crucial role in our mental and physical health. Neurons containing the neurotransmitter dopamine are clustered in the midbrain in an area called the substantia nigra. In Parkinson's disease, the dopamine-transmitting neurons in this area die. As a result, the brains of people with Parkinson's disease contain almost no dopamine. To help relieve their symptoms, these patients are given L-DOPA, a drug that can be converted in the brain to dopamine.

Norepinephrine, also called noradrenaline, is a neurotransmitter that also acts as a hormone. As a neurotransmitter, norepinephrine helps to regulate arousal, dreaming, and moods. As a hormone, it acts to increase blood pressure, constrict blood vessels and increase heart rate—responses that occur when we feel stress.

Serotonin (5-hydroxytryptamine, 5-HT) is widely distributed in animals and plants, occurring in vertebrates, fruits, nuts, and venoms. A number of congeners of serotonin are also found in nature and have been shown to possess a variety of peripheral and central nervous system activities. Serotonin may be obtained from a variety of dietary sources; however, endogenous 5-HT is synthesized in situ from tryptophan through the actions of the enzymes tryptophan hydroxylase and aromatic L-amino acid decarboxylase. Both dietary and endogenous 5-HT are rapidly metabolized and inactivated by monoamine oxidase and aldehyde dehydrogenase to the major metabolite, 5-hydroxyindoleacetic acid (5-HIAA).

Serotonin is implicated in the etiology or treatment of various disorders, particularly those of the central nervous system, including anxiety, depression, obsessive-compulsive disorder, schizophrenia, stroke, obesity, pain, hypertension, vascular disorders, migraine, and nausea. Recently, understanding of the role of 5-HT in these and other disorders has advanced rapidly due to increasing understanding of the physiological role of various serotonin receptor subtypes.

Although various methods have been reported for laboratory synthesis of piperidines, the vast majority of these methods are not suitable for a commercial-scale process. Moreover, there are no reliable stereoselective methods for the controled asymmetric synthesis of substituted piperidines. The disadvantages of the traditional synthetic methods include modest overall yields and poor stereoselectivities. Moreover, small amounts of by-products, such as undesired stereoisomers, often accumulate during the synthetic protocol, making complete purification of the final product difficult.

SUMMARY OF THE INVENTION

One aspect of the present invention relates to methods of synthesizing substituted piperidines. A second aspect of the present invention relates to stereoselective methods of synthesizing substituted piperidines. The methods of the present invention will find use in the synthesis of compounds useful for treatment of numerous ailments, conditions and diseases that afflict mammals, including but not limited to addiction and pain. An additional aspect of the present invention relates to the synthesis of combinatorial libraries of the substituted piperidines using the methods of the present invention. An additional aspect of the present invention relates to enantiomerically substituted pyrrolidines, piperidines, and azepines.

BRIEF DESCRIPTION OF THE FIGURES

FIG. 1 depicts certain structural classes of substituted piperidines that can be prepared according to the methods of the present invention.

FIG. 5 depicts a proposed asymmetric synthesis of a 3-substituted piperidine.

FIG. 6 depicts a proposed asymmetric synthesis of a 3-substituted piperidine.

FIG. 16 depicts peak retention times obtained from HPLC traces for various mixtures comprising a compound prepared according to the methods of the present invention.

FIG. 17 depicts peak retention times obtained from HPLC traces for various mixtures comprising a compound prepared according to the methods of the present invention.

FIG. 18 depicts peak retention times obtained from HPLC traces for various mixtures comprising a compound prepared according to the methods of the present invention.

FIG. 20 depicts various asymmetric ligands that may be comprised by the asymmetric catalysts utilized in the asymmetric synthetic methods of the present invention.

FIG. 23 depicts various asymmetric ligands that may be comprised by the asymmetric catalysts utilized in the asymmetric synthetic methods of the present invention.

FIG. 25 depicts various asymmetric ligands that may be comprised by the asymmetric catalysts utilized in the asymmetric synthetic methods of the present invention.

FIG. 29 depicts various asymmetric ligands that may be comprised by the asymmetric catalysts utilized in the asymmetric synthetic methods of the present invention.

FIG. 31 depicts various asymmetric ligands that may be comprised by the asymmetric catalysts utilized in the asymmetric synthetic methods of the present invention.

FIG. 32 depicts various asymmetric ligands that may be comprised by the asymmetric catalysts utilized in the asymmetric synthetic methods of the present invention.

FIG. 33 depicts various asymmetric ligands that may be comprised by the asymmetric catalysts utilized in the asymmetric synthetic methods of the present invention.

DETAILED DESCRIPTION OF THE INVENTION

Figure 2:
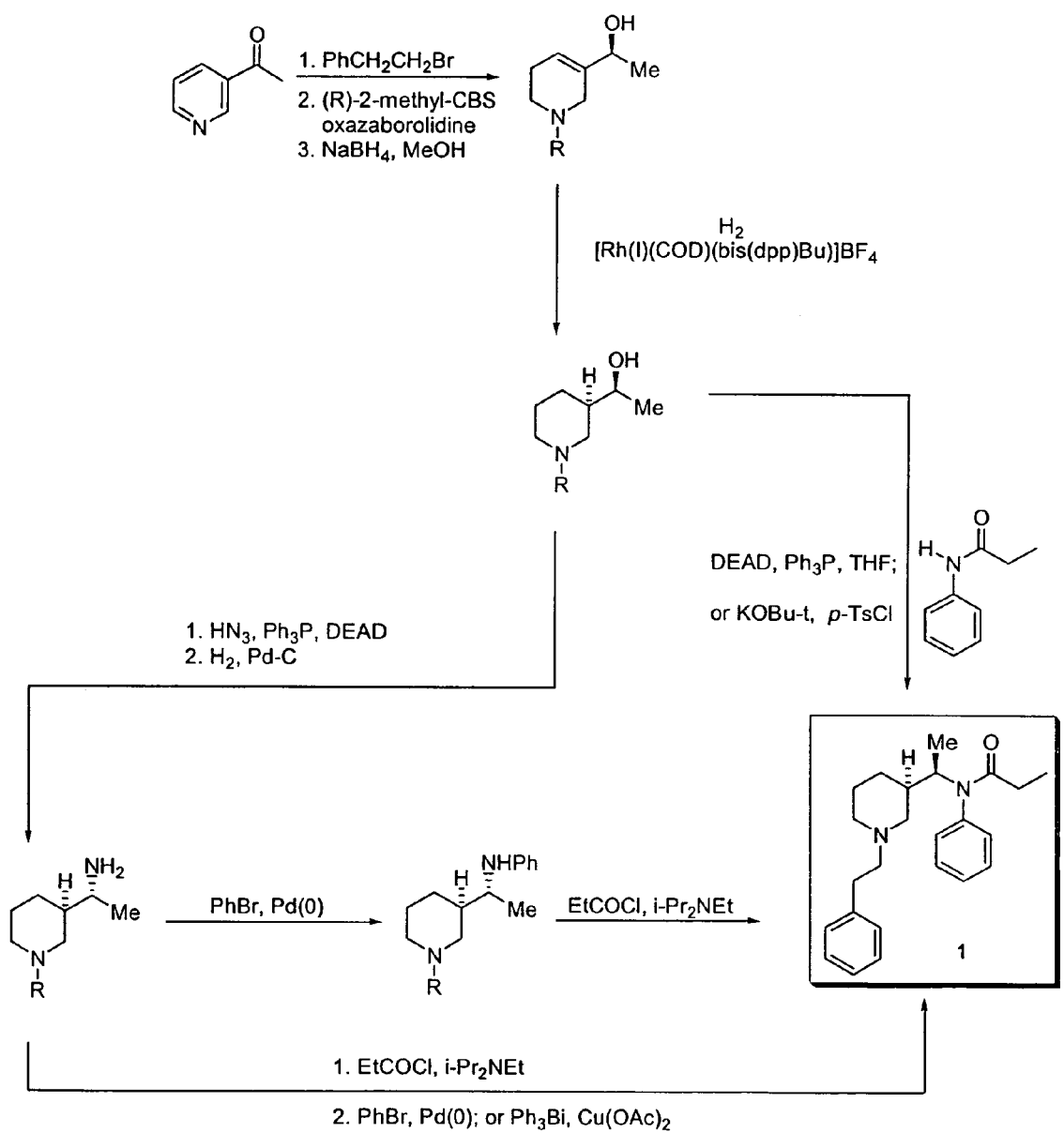
FIG. 2 depicts a proposed asymmetric synthesis of a 3-substituted piperidine.

Pain is an unpleasant sensation varying in severity in a local part of the body or several parts of the body resulting from injury, disease, or emotional disorder. Pain can be classified according to its duration. Acute pain, which lasts less than one month, usually has a readily identifiable cause (e.g., hip fracture) and signals tissue damage. The associated effect is often anxiety, and the concomitant physiologic findings are those of sympathetic stimulation (e.g., tachycardia, tachypnea, diaphoresis). In addition, acute pain syndromes can be episodic, for example recurrent discomfort from arthritis.

Chronic pain can be defined as pain that persists more than one month beyond the usual course of an acute illness or injury, or pain that recurs at intervals over months or years, or pain that is associated with a chronic pathologic process. In contrast to acute pain, chronic pain loses its adaptive biologic function. Depression is common, and abnormal illness behavior often compounds the patient's impairment. Chronic pain can be divided broadly into that which is inferred to be predominantly somatogenic and that which is inferred to be predominantly psychogenic. A similar classification based on inferred pathophysiology designates chronic pain as nociceptive (commensurate with ongoing activation of pain-sensitive nerve fibers), neuropathic (due to aberrant somatosensory processing in afferent neural pathways), or psychogenic.

Nociceptive pain can be somatic or visceral. Most chronic pain in the elderly is nociceptive and somatic; arthritis, cancer pain, and myofascial pain are most common. Relief is likely with removal of the peripheral cause (e.g., reducing periarticular inflammation), and analgesic drugs are often effective.

A common subtype of neuropathic pain, known collectively as peripheral neuropathic pain, is presumably sustained by mechanisms that involve disturbances in the peripheral nerve or nerve root; neuroma formation after axonal injury and nerve compression are the two major processes. Another subtype of neuropathic pain is related to the reorganization of nociceptive information processing by the CNS; it persists without ongoing activation of pain-sensitive fibers. This type of pain, known collectively as the deafferentation syndromes, includes postherpetic neuralgia, central pain (which can result from a lesion at any level of the CNS), phantom limb pain, and others. A third subtype of neuropathic pain, often called sympathetically maintained pain, can be ameliorated by interruption of sympathetic nerves to the painful area; the prototypic disorder is reflex sympathetic dystrophy. The precise mechanisms involved in these disorders are conjectural, but all can produce an unfamiliar pain, often described as burning and stabbing. Currently, this type of pain responds poorly to analgesics.

Some patients have persistent pain without either nociceptive foci or evidence of a neuropathic mechanism for the pain. Many others have nociceptive lesions that do not sufficiently explain the degree of pain and disability. Psychopathologic processes account for these complaints in some patients. If no evidence for a psychological cause is found, the pain is referred to as idiopathic. Many patients have an idiopathic pain syndrome that is best described by the generic diagnosis chronic nonmalignant pain syndrome, a term denoting pain and disability disproportionate to an identifiable somatic cause and usually related to a more pervasive set of abnormal illness behaviors. Some of these patients may be labeled by the more formal psychiatric diagnosis of somatoform pain disorder. Others have complaints that constitute a specific pain diagnosis, most commonly the failed low back syndrome or atypical facial pain. Still others have significant organic lesions (e.g., lumbar arachnoiditis) but also have a clear psychological contribution associated with excessive disability. Diagnosis may be difficult, but the relative contributions of both organic and psychological components of the pain can be defined.

Another clinically useful classification of chronic pain is broadly syndromic. For example, chronic pain may be part of a medical illness (e.g., cancer or arthritis). A mixture of pathophysiologic mechanisms may be involved; e.g., tumor invasion of nerve and bone may cause neuropathic and somatic nociceptive pains, respectively, and psychological factors may be prominent.

Three general classes of drugs are currently available for pain management, nonsteriodal anti-inflammatories, opioids, and adjuvant analgesics. The nonsteriodal anti-inflammatories class includes drugs such as aspirin, ibuprofen, diclofenac, acetaminophen, and rofecoxib. The opioid class includes morphine, oxycodone, fentanyl, and pentazocine. Adjuvant analgesics include various antidepressants, anticonvulsants, neuroleptics, and corticosteroids.

Of the three classes of pharmaceutical agents used for pain management, opioid are usually most efficacious for treating moderate to severe pain. Although opioids can be very effective in pain management, they do cause several side effects, such as respiratory depression, constipation, physical dependence, tolerance, withdraw. These unwanted effects can severely limit their use. Therefore, there is a current need for pharmaceutical agents that retain the analgesic properties of the known opioid, but have reduced side effect profiles for the treatment of pain.

Opioids, specifically ligands for the $\mu$-opioid receptor, are the major class of analgesics used in the management of moderate to severe pain because of their effectiveness, ease of titration, and favorable risk-to-benefit ratio. Unfortunately, the opioids currently available have several unwanted side-effects, such as respiratory depression and constipation. In addition, these agents may lead to tolerance and dependence. Research into the development of new, selective ligands for opioid receptors holds the promise of yielding potent analgesics that lack the side effects of morphine and its congeners. Applicants herein disclose novel analgesics, including selective ligands for opioid receptors. Individual compounds described herein promise to have agonistic, antagonistic, and hybrid effects on opioid and other cellular receptors. Additionally, new compounds reported herein may possess analgesic properties free from respiratory depression and the potential for physical dependence associated with $\mu$-opioid receptor ligands, such as morphine and fentanyl. Moreover, new compounds reported herein may possess properties for the treatment of physical or psychological additions, psychiatric disorders, and neurological pathologies, such as tinnitus.

The $\mu$-opioid receptor is a member of a family of cell surface proteins that permit intracellular transduction of extracellular signals. Cell surface proteins provide eukaryotic and prokaryotic cells a means to detect extracellular signals and transduce such signals intracellularly in a manner that ultimately results in a cellular response or a concerted tissue or organ response. Cell surface proteins, by intracellularly transmitting information regarding the extracellular environment via specific intracellular pathways induce an appropriate response to a particular stimulus. The response may be immediate and transient, slow and sustained, or some mixture thereof. By virtue of an array of varied membrane surface proteins, eukaryotic cells are exquisitely sensitive to their environment.

Definitions

For convenience, certain terms employed in the specification, examples, and appended claims are collected here.

The term "heteroatom" as used herein means an atom of any element other than carbon or hydrogen. Preferred heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, J. March, *Advanced Organic Chemistry*, McGraw Hill Book Company, New York, (1977 edition) pp. 251–259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused-rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "(R)-2-Methyl-CBS-oxazaborolidine" and its systematic name "(R)-tetrahydro-1-methyl-3,3-diphenyl-1H,3H-pyrrolo[1,2-c][1,3,2]oxazaborole" refer to the following reagent:

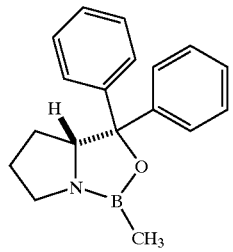

The term "(S)-2-Methyl-CBS-oxazaborolidine" and its systematic name "(S)-tetrahydro-1-methyl-3,3-diphenyl-1H,3H-pyrrolo[1,2-c][1,3,2]oxazaborole" refer to the following reagent:

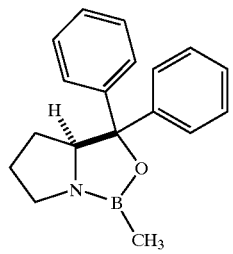

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

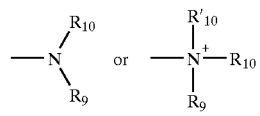

wherein $R_9$, $R_{10}$ and $R'_{10}$ each independently represent a group permitted by the rules of valence.

The term "acylamino" is art-recognized and refers to a moiety that can be represented by the general formula:

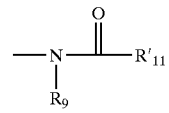

wherein $R_9$ represents a group permitted by the rules of valence, and $R'_{11}$ represents hydrogen, alkyl, cycloalkyl, alkenyl, aryl, heteroaryl, aralkyl, or heteroaralkyl.

The term "amido" is art recognized as an amino-substituted carbonyl and includes a moiety that can be represented by the general formula:

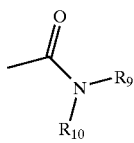

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethyl thio, and the like.

The term "carbonyl" is art recognized and includes such moieties as can be represented by the general formula:

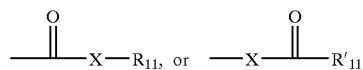

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

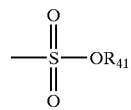

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms, Cbz, and Boc represent methyl, ethyl, phenyl, trifluoromethanesulfonyl, nonafluorobutanesulfonyl, p-toluenesulfonyl, methanesulfonyl, benzyloxycarbonyl, and t-butyloxycarbonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

The term "sulfate" is art recognized and includes a moiety that can be represented by the general formula:

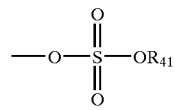

in which $R_{41}$ is as defined above.

The term "sulfonylamino" is art recognized and includes a moiety that can be represented by the general formula:

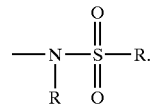

The term "sulfamoyl" is art-recognized and includes a moiety that can be represented by the general formula:

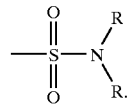

The term "sulfonyl", as used herein, refers to a moiety that can be represented by the general formula:

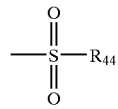

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

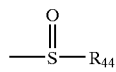

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, and —Se-alkynyl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, carbamates of amines, ureas of amines, and acetals and ketals of aldehydes and ketones, respectively. The field of protecting group chemistry has been reviewed (Greene, T. W. Wuts, P. G. M. *Protective Groups in Organic Synthesis*, 2$^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to opioid receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986–87, inside cover.

Compounds of the Invention

The compounds of the present invention are enantiomerically-enriched substituted pyrrolidines, piperidines, and azepines useful for treatment of numerous ailments, conditions and diseases that afflict mammals, including but not limited to addiction and pain (see FIG. 1).

In certain embodiments, a compound of the present invention is represented by formula I:

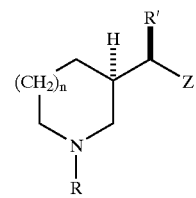

wherein
n is 0, 1, or 2;
R is H, aralkyl, or —CO$_2$R';
R' is alkyl, aryl, or aralkyl;
Z is NHR" or OH; and
R" is H, alkyl, aryl, or aralkyl.

In certain embodiments, the compounds of the present invention are represented by formula I and the attendant definitions, wherein n is 1.

In certain embodiments, the compounds of the present invention are represented by formula I and the attendant definitions, wherein R is Cbz.

In certain embodiments, the compounds of the present invention are represented by formula I and the attendant definitions, wherein R is —CH$_2$CH$_2$Ph.

In certain embodiments, the compounds of the present invention are represented by formula I and the attendant definitions, wherein R is H.

In certain embodiments, the compounds of the present invention are represented by formula I and the attendant definitions, wherein R' is methyl.

In certain embodiments, the compounds of the present invention are represented by formula I and the attendant definitions, wherein Z is OH.

In certain embodiments, the compounds of the present invention are represented by formula I and the attendant definitions, wherein Z is NHR"; and R" is phenyl.

In certain embodiments, the compounds of the present invention are represented by formula I and the attendant definitions, wherein n is 1; and R is Cbz.

In certain embodiments, the compounds of the present invention are represented by formula I and the attendant definitions, wherein n is 1; and R' is Me.

In certain embodiments, the compounds of the present invention are represented by formula I and the attendant definitions, wherein n is 1; R' is Me; and Z is OH.

In certain embodiments, the compounds of the present invention are represented by formula I and the attendant definitions, wherein n is 1; R' is Me; Z is OH; and R is Cbz.

In certain embodiments, the compounds of the present invention are represented by formula I and the attendant definitions, wherein n is 1; R' is Me; Z is NHR"; and R" is phenyl.

In certain embodiments, the compounds of the present invention are represented by formula I and the attendant definitions, wherein n is 1; R' is Me; Z is NHR"; R" is phenyl; and R is Cbz.

In certain embodiments, the compounds of the present invention are represented by formula I and the attendant definitions, wherein n is 1; R is Cbz; and R' is methyl.

In certain embodiments, the compounds of the present invention are represented by formula I and the attendant definitions, wherein n is 1; and R is —CH$_2$CH$_2$Ph.

In certain embodiments, the compounds of the present invention are represented by formula I and the attendant definitions, wherein n is 1; R is —CH$_2$CH$_2$Ph; and R' is methyl.

In certain embodiments, the compounds of the present invention are represented by formula I and the attendant definitions, wherein n is 1; R is —CH$_2$CH$_2$Ph; R' is methyl; and Z is OH.

In certain embodiments, the compounds of the present invention are represented by formula I and the attendant definitions, wherein n is 1; R is —CH$_2$CH$_2$Ph; R' is methyl; Z is NHR"; and R" is phenyl.

In certain embodiments, a compound of the present invention is represented by formula II:

wherein
n is 0, 1, or 2;
R is H, aralkyl, or —CO$_2$R';
R' is alkyl, aryl, or aralkyl;
Z is NHR" or OH; and
R" is H, alkyl, aryl, or aralkyl.

In certain embodiments, the compounds of the present invention are represented by formula II and the attendant definitions, wherein n is 1.

In certain embodiments, the compounds of the present invention are represented by formula II and the attendant definitions, wherein R is Cbz.

In certain embodiments, the compounds of the present invention are represented by formula II and the attendant definitions, wherein R is —CH$_2$CH$_2$Ph.

In certain embodiments, the compounds of the present invention are represented by formula II and the attendant definitions, wherein R is H.

In certain embodiments, the compounds of the present invention are represented by formula II and the attendant definitions, wherein R' is methyl.

In certain embodiments, the compounds of the present invention are represented by formula II and the attendant definitions, wherein Z is OH.

In certain embodiments, the compounds of the present invention are represented by formula II and the attendant definitions, wherein Z is NHR"; and R" is phenyl.

In certain embodiments, the compounds of the present invention are represented by formula II and the attendant definitions, wherein n is 1; and R is Cbz.

In certain embodiments, the compounds of the present invention are represented by formula II and the attendant definitions, wherein n is 1; and R' is Me.

In certain embodiments, the compounds of the present invention are represented by formula II and the attendant definitions, wherein n is 1; R' is Me; and Z is OH.

In certain embodiments, the compounds of the present invention are represented by formula II and the attendant definitions, wherein n is 1; R' is Me; Z is OH; and R is Cbz.

In certain embodiments, the compounds of the present invention are represented by formula II and the attendant definitions, wherein n is 1; R' is Me; Z is NHR"; and R" is phenyl.

In certain embodiments, the compounds of the present invention are represented by formula II and the attendant definitions, wherein n is 1; R' is Me; Z is NHR"; R" is phenyl; and R is Cbz.

In certain embodiments, the compounds of the present invention are represented by formula II and the attendant definitions, wherein n is 1; R is Cbz; and R' is methyl.

In certain embodiments, the compounds of the present invention are represented by formula II and the attendant definitions, wherein n is 1; and R is —CH$_2$CH$_2$Ph.

In certain embodiments, the compounds of the present invention are represented by formula II and the attendant definitions, wherein n is 1; R is —CH$_2$CH$_2$Ph; and R' is methyl.

In certain embodiments, the compounds of the present invention are represented by formula II and the attendant definitions, wherein n is 1; R is —CH$_2$CH$_2$Ph; R' is methyl; and Z is OH.

In certain embodiments, the compounds of the present invention are represented by formula II and the attendant definitions, wherein n is 1; R is —CH$_2$CH$_2$Ph; R' is methyl; Z is NHR"; and R" is phenyl.

In certain embodiments, a compound of the present invention is represented by formula III:

III wherein
n is 0, 1, or 2;
R is H, aralkyl, or —CO$_2$R';
R' is alkyl, aryl, or aralkyl;
Z is NHR" or OH; and
R" is H, alkyl, aryl, or aralkyl.
R" is H, alkyl, aryl, or aralkyl.

In certain embodiments, the compounds of the present invention are represented by formula III and the attendant definitions, wherein n is 1.

In certain embodiments, the compounds of the present invention are represented by formula III and the attendant definitions, wherein R is Cbz.

In certain embodiments, the compounds of the present invention are represented by formula III and the attendant definitions, wherein R is —CH$_2$CH$_2$Ph.

In certain embodiments, the compounds of the present invention are represented by formula III and the attendant definitions, wherein R is H.

In certain embodiments, the compounds of the present invention are represented by formula III and the attendant definitions, wherein R' is methyl.

In certain embodiments, the compounds of the present invention are represented by formula III and the attendant definitions, wherein Z is OH.

In certain embodiments, the compounds of the present invention are represented by formula III and the attendant definitions, wherein Z is NHR"; and R" is phenyl.

In certain embodiments, the compounds of the present invention are represented by formula III and the attendant definitions, wherein n is 1; and R is Cbz.

In certain embodiments, the compounds of the present invention are represented by formula III and the attendant definitions, wherein n is 1; and R' is Me.

In certain embodiments, the compounds of the present invention are represented by formula III and the attendant definitions, wherein n is 1; R' is Me; and Z is OH.

In certain embodiments, the compounds of the present invention are represented by formula III and the attendant definitions, wherein n is 1; R' is Me; Z is OH; and R is Cbz.

In certain embodiments, the compounds of the present invention are represented by formula III and the attendant definitions, wherein n is 1; R' is Me; Z is NHR"; and R" is phenyl.

In certain embodiments, the compounds of the present invention are represented by formula III and the attendant definitions, wherein n is 1; R' is Me; Z is NHR"; R" is phenyl; and R is Cbz.

In certain embodiments, the compounds of the present invention are represented by formula III and the attendant definitions, wherein n is 1; R is Cbz; and R' is methyl.

In certain embodiments, the compounds of the present invention are represented by formula III and the attendant definitions, wherein n is 1; and R is —CH$_2$CH$_2$Ph.

In certain embodiments, the compounds of the present invention are represented by formula III and the attendant definitions, wherein n is 1; R is —CH$_2$CH$_2$Ph; and R' is methyl.

In certain embodiments, the compounds of the present invention are represented by formula III and the attendant definitions, wherein n is 1; R is —CH$_2$CH$_2$Ph; R' is methyl; and Z is OH.

In certain embodiments, the compounds of the present invention are represented by formula III and the attendant definitions, wherein n is 1; R is —CH$_2$CH$_2$Ph; R' is methyl; Z is NHR"; and R" is phenyl.

In certain embodiments, a compound of the present invention is represented by formula IV:

IV wherein
n is 0, 1, or 2;
R is H, aralkyl, or —CO$_2$R';
R' is alkyl, aryl, or aralkyl;
Z is NHR" or OH; and
R" is H, alkyl, aryl, or aralkyl.

In certain embodiments, the compounds of the present invention are represented by formula IV and the attendant definitions, wherein n is 1.

In certain embodiments, the compounds of the present invention are represented by formula IV and the attendant definitions, wherein R is Cbz.

In certain embodiments, the compounds of the present invention are represented by formula IV and the attendant definitions, wherein R is —CH$_2$CH$_2$Ph.

In certain embodiments, the compounds of the present invention are represented by formula IV and the attendant definitions, wherein R is H.

In certain embodiments, the compounds of the present invention are represented by formula IV and the attendant definitions, wherein R' is methyl.

In certain embodiments, the compounds of the present invention are represented by formula IV and the attendant definitions, wherein Z is OH.

In certain embodiments, the compounds of the present invention are represented by formula IV and the attendant definitions, wherein Z is NHR"; and R" is phenyl.

In certain embodiments, the compounds of the present invention are represented by formula IV and the attendant definitions, wherein n is 1; and R is Cbz.

In certain embodiments, the compounds of the present invention are represented by formula IV and the attendant definitions, wherein n is 1; and R' is Me.

In certain embodiments, the compounds of the present invention are represented by formula IV and the attendant definitions, wherein n is 1; R' is Me; and Z is OH.

In certain embodiments, the compounds of the present invention are represented by formula IV and the attendant definitions, wherein n is 1; R' is Me; Z is OH; and R is Cbz.

In certain embodiments, the compounds of the present invention are represented by formula IV and the attendant definitions, wherein n is 1; R' is Me; Z is NHR"; and R" is phenyl.

In certain embodiments, the compounds of the present invention are represented by formula IV and the attendant definitions, wherein n is 1; R' is Me; Z is NHR"; R" is phenyl; and R is Cbz.

In certain embodiments, the compounds of the present invention are represented by formula IV and the attendant definitions, wherein n is 1; R is Cbz; and R' is methyl.

In certain embodiments, the compounds of the present invention are represented by formula IV and the attendant definitions, wherein n is 1; and R is —CH$_2$CH$_2$Ph.

In certain embodiments, the compounds of the present invention are represented by formula IV and the attendant definitions, wherein n is 1; R is —CH$_2$CH$_2$Ph; and R' is methyl.

In certain embodiments, the compounds of the present invention are represented by formula IV and the attendant definitions, wherein n is 1; R is —CH$_2$CH$_2$Ph; R' is methyl; and Z is OH.

In certain embodiments, the compounds of the present invention are represented by formula IV and the attendant definitions, wherein n is 1; R is —CH$_2$CH$_2$Ph; R' is methyl; Z is NHR''; and R'' is phenyl.

Methods of the Invention

One aspect of the present invention relates to synthetic procedures for the enantio- and diastereo-selective syntheses of each of the four stereoisomeric compounds 1, 2, 3 and 4, which procedures are described herein.

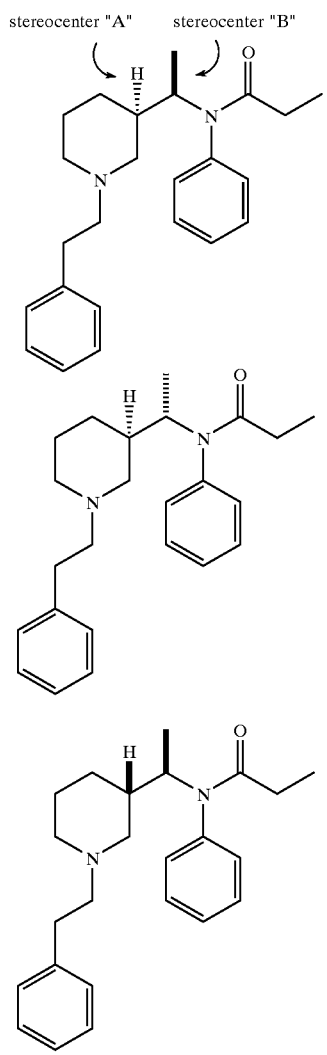

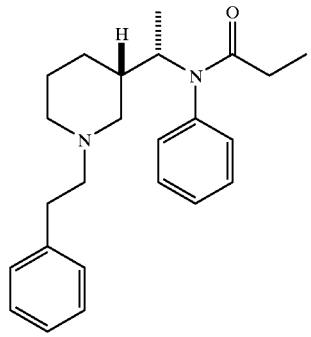

Figure 3:
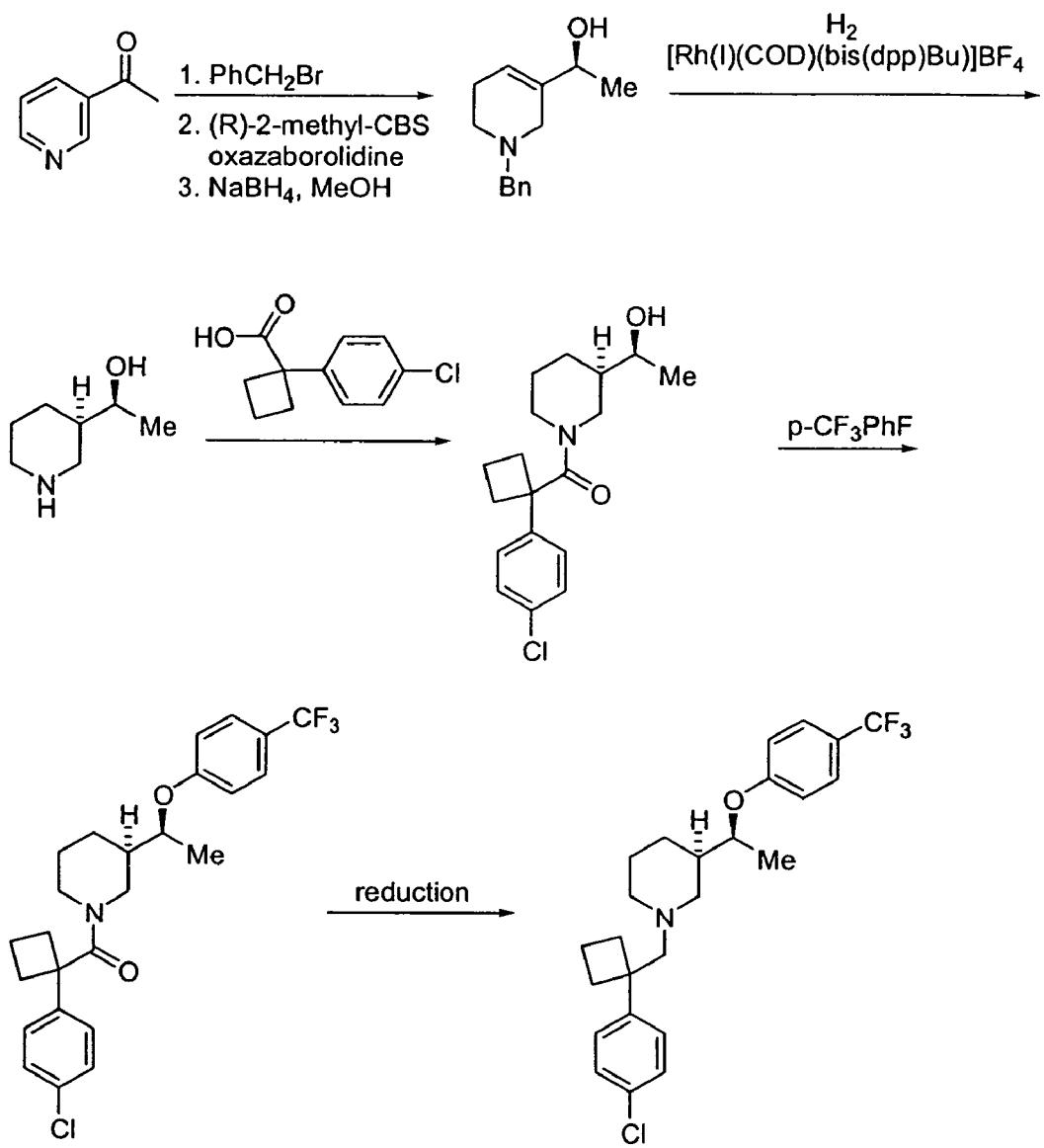
FIG. 3 depicts a proposed asymmetric synthesis of a 3-substituted piperidine.
Figure 4:
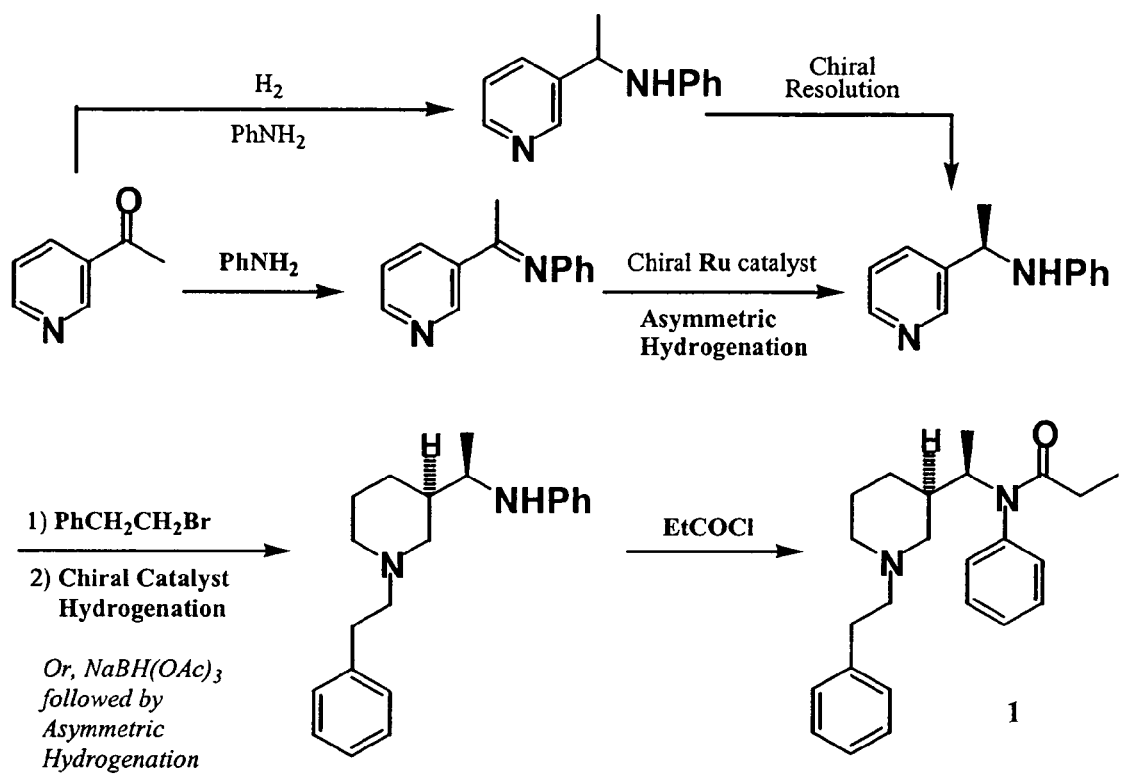
FIG. 4 depicts a proposed asymmetric synthesis of a 3-substituted piperidine.
Figure 7:
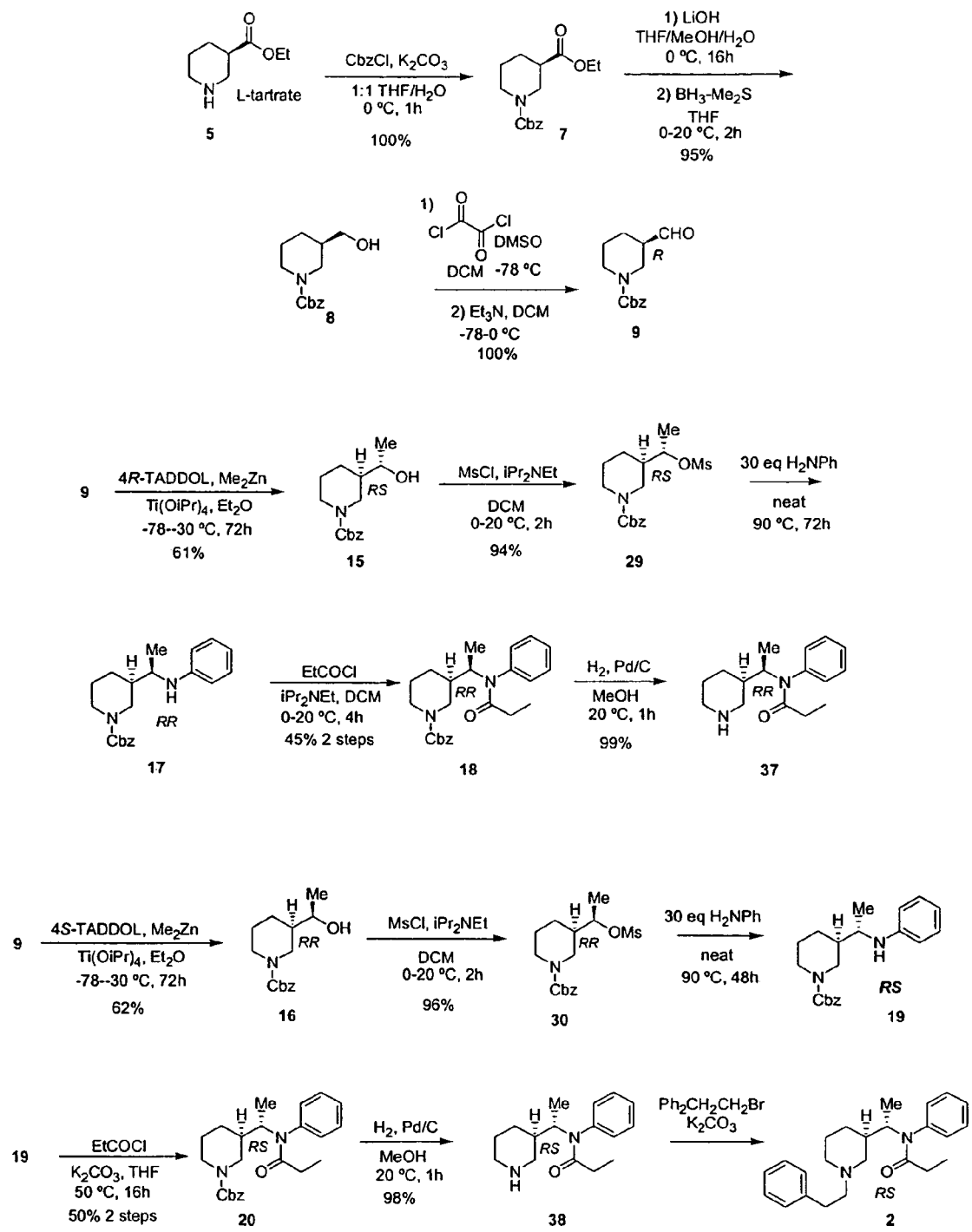
FIG. 7 depicts schematically synthetic routes to compounds 37 and 2.
Figure 8:
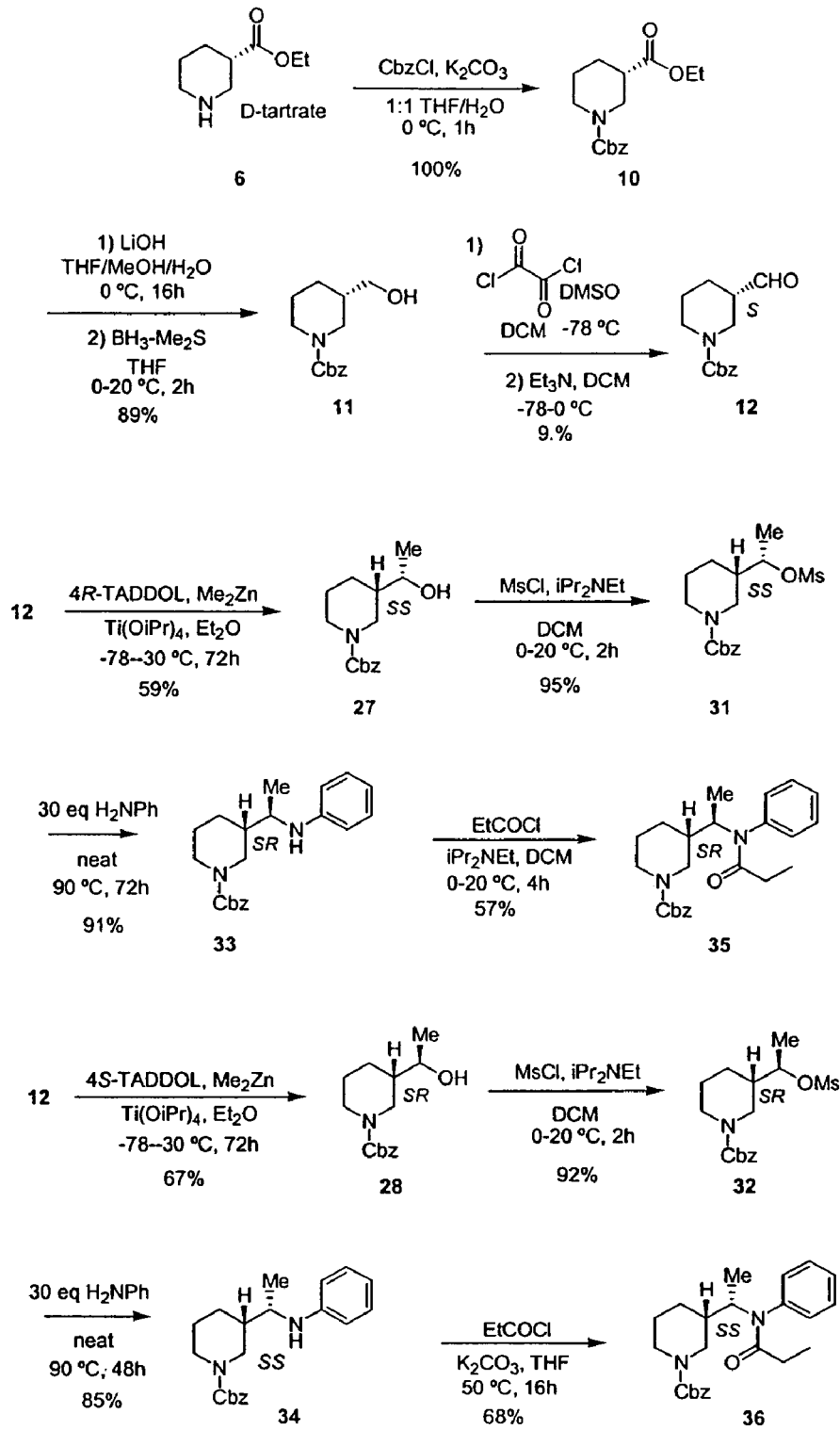
FIG. 8 depicts schematically synthetic routes to compounds 35 and 36.
Figure 9:
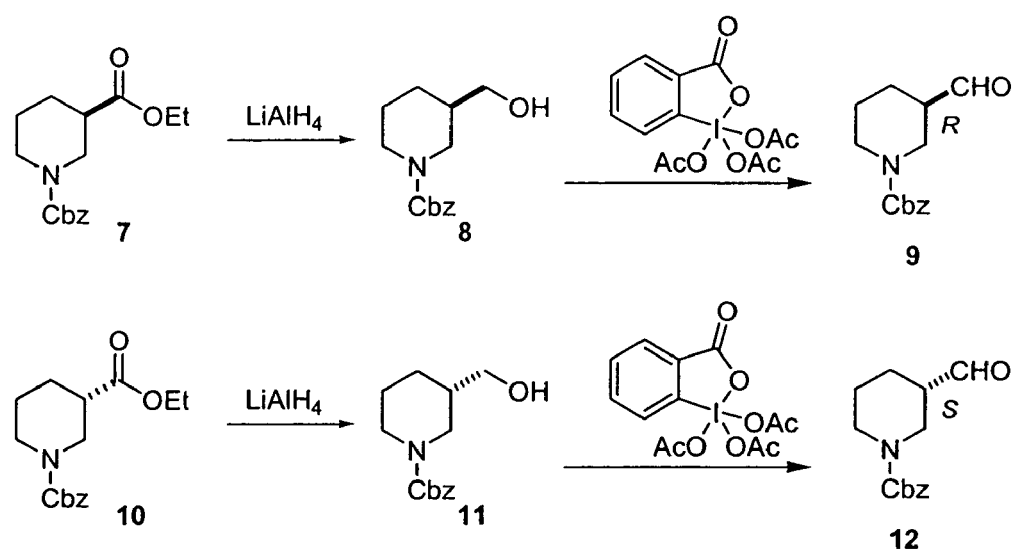
FIG. 9 depicts schematically a synthetic route to compounds 9 and 12.
Figure 10:
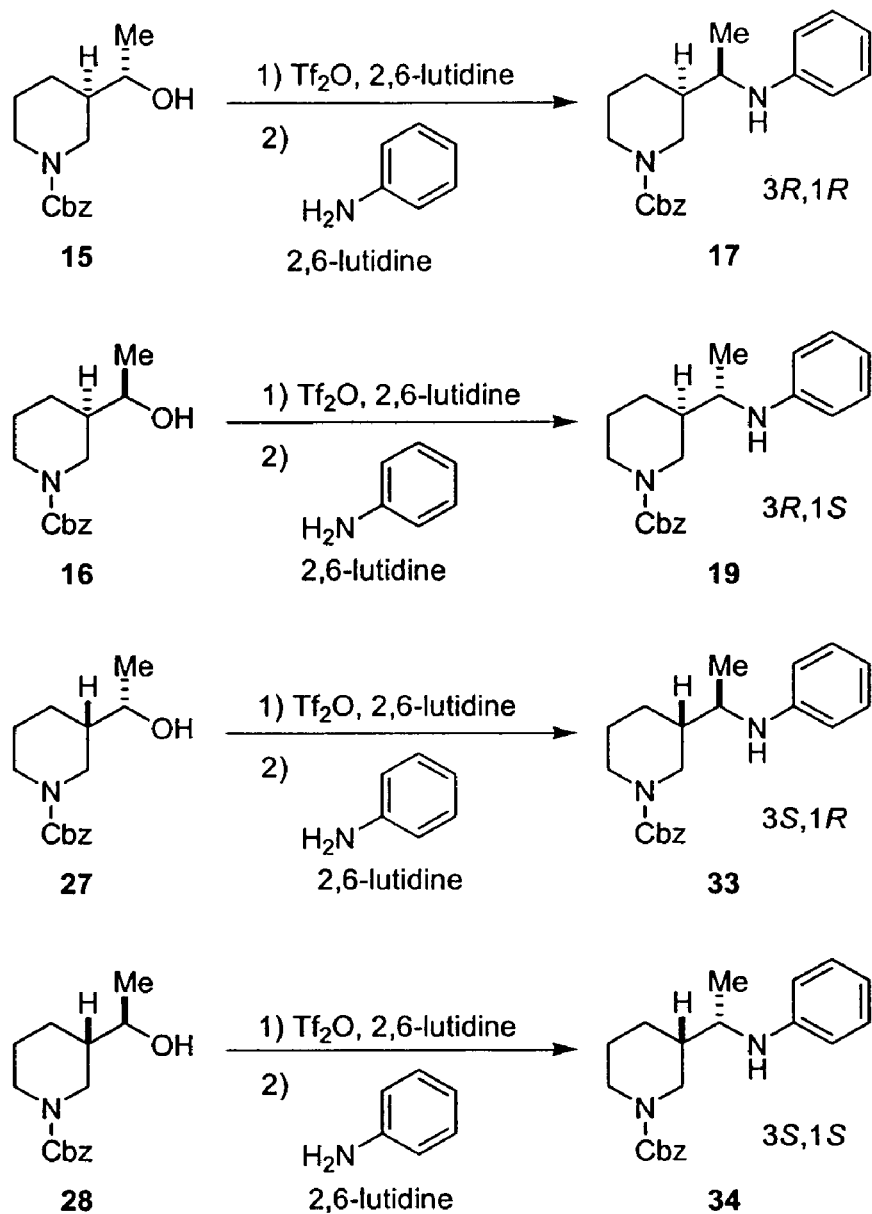
FIG. 10 depicts schematically a synthetic route to compounds 17, 19, 33, and 34.

Several synthetic routes have been envisioned by the inventors, including several that start from 3-acylpyridine and include a stereoselective reduction of the acyl carbonyl to substantially one enantiomer of an alcohol (see FIGS. 2–4). One synthetic route in particular is described in greater detail below and starts from substantially one enantiomer of a 3-ester substituted cyclic amine. The synthetic route converts the ester to an aldehyde followed by a stereoselective nucleophilic addition to the aldehyde to produce substantially one enantiomer of an alcohol (see FIGS. 5 and 6).

In general, the first stereocenter ("A") may be obtained enantiopure in the form of a commercially available tartrate salt of ethyl nipecotate. For example, commercially available (R)-ethyl nipecotate is typically an (l)-tartaric acid (5); whereas, commercially available (S)-ethyl nipecotate is typically a (d)-tartaric acid salt (6).

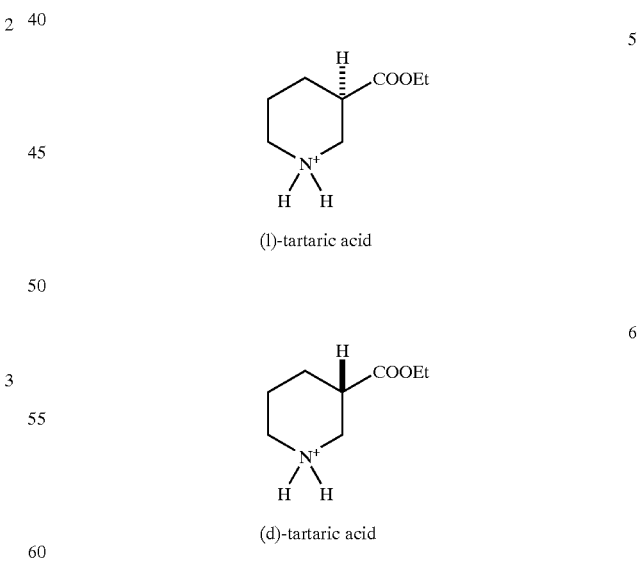

Enantiopure esters 5 and 6 were taken forward to aldehydes 9 and 12 following the reaction scheme outlined below. Amines 5 and 6 were protected as carbamates 7 and 10, respectively. Other protecting groups that render the amine non-basic are anticipated to be acceptable.

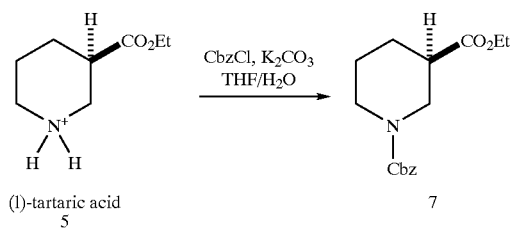

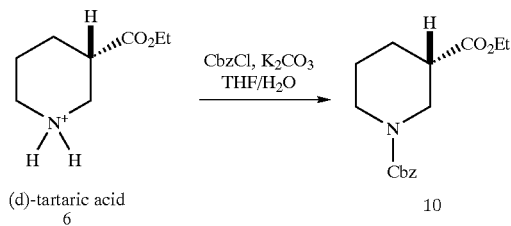

Reduction of the ester by either a one-step or two-step protocol provided alcohols 8 and 11. For the one step procedure, treatment of esters 7 and 10 with lithium aluminum hydride provided the desired alcohols 8 and 11, respectively.

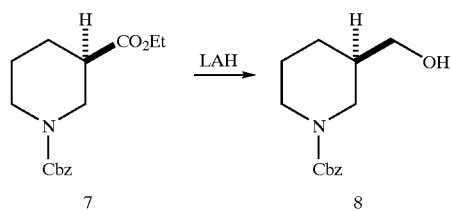

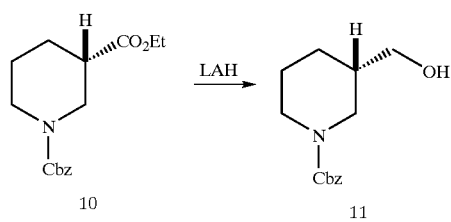

For the two-step procedure, ester hydrolysis to the acid followed by borane-dimethyl sulfide reduction provided alcohols 8 and 11. Other commonly employed reagents for the conversion of these intermediates to the alcohol are anticipated to be acceptable.

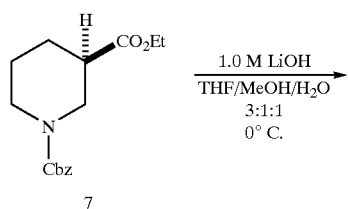

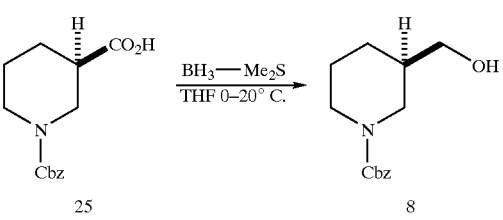

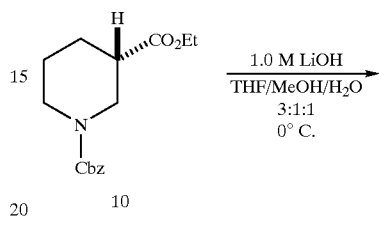

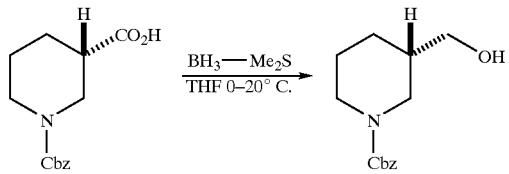

Aldehydes 9 and 12 can be obtained using a variety of reaction conditions commonly used for such transformations. For example, it is anticipated that the esters (7 and 10), acids (25 and 26) or corresponding acid halides could be converted directly to aldehydes 9 and 12.

Aldehydes 9 and 12 were synthesized from alcohols 8 and 11 by Swern oxidation. Aldehyde 9 was also obtained by Dess-Martin oxidation. It is anticipated that Dess-Martin oxidation could be used to convert alcohol 11 to aldehyde 12 equally well. Other commonly used oxidants such as such as pyridinium chlorochromate are also anticipated to work for this transformation.

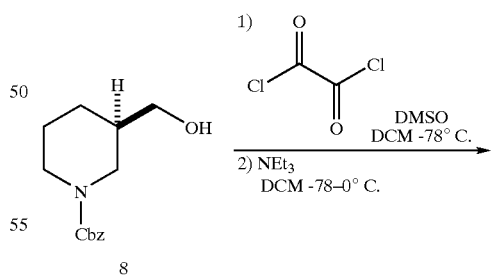

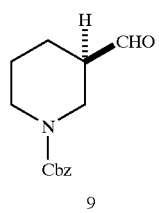

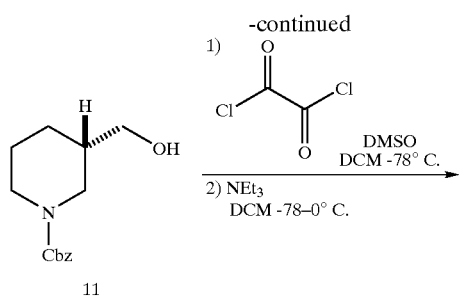

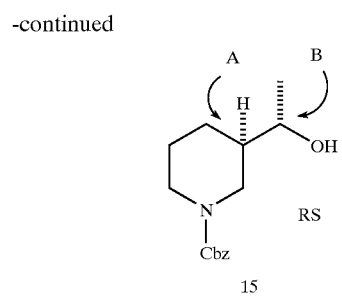

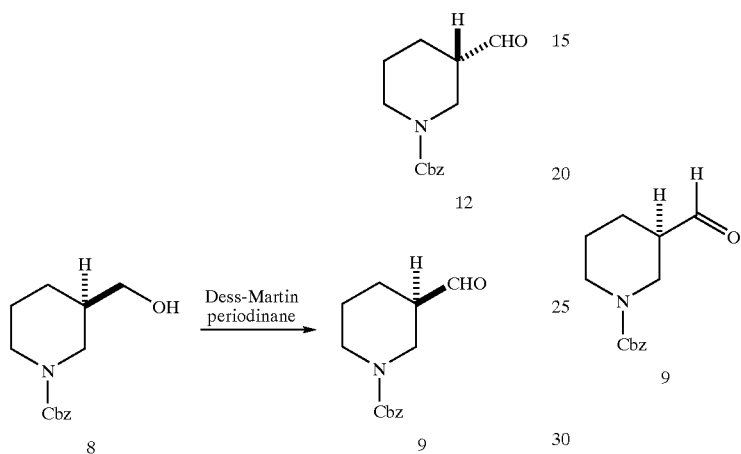

The second stereocenter of the piperidines ("B") was selectively installed utilizing a diastereoselective addition of dimethylzinc catalyzed by the TADDOL catalyst, developed by D. Seebach (J. L. von dem Bussche-Hunnefeld and D. Seebach, *Tetrahedron*, 1992, 48(27), 5719), to aldehydes 9 and 12. Among other catalysts, the TADDOL catalyst with Ar=Phenyl and 1-naphthyl was effective; however, even better results were achieved with the TADDOL catalyst wherein Ar=2-naphthyl. By choosing the correct TADDOL catalyst enantiomer (13 or 14), product with either the (S)-(15) or (R)-(16) configuration for stereocenter "B" was achieved. Assignment of stereochemistry was made based on literature precedents. Catalyst 13 promotes addition to the si face to form 15 (RS) and 27 (SS) from aldehydes 9 and 12, respectively; whereas, catalyst 14 promotes addition to the re face to form alcohol 16 (RR) and 28 (SR) from aldehydes 9 and 12, respectively.

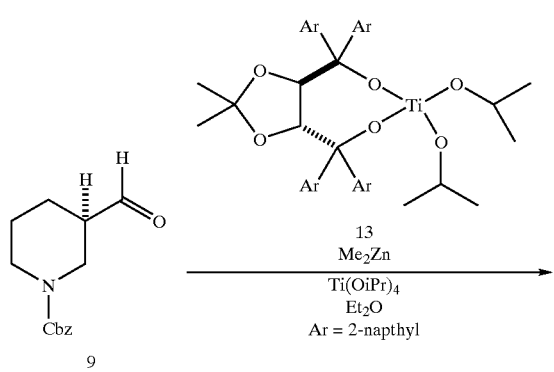

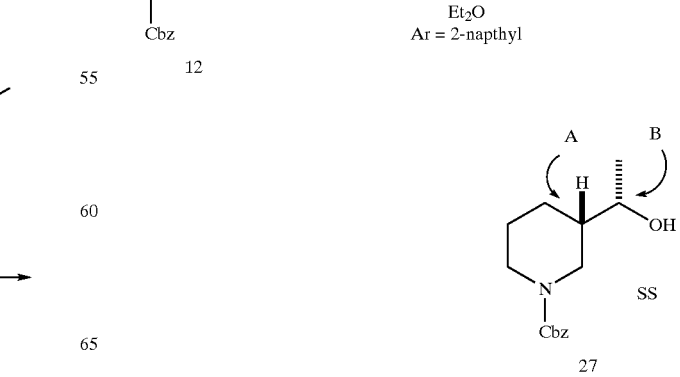

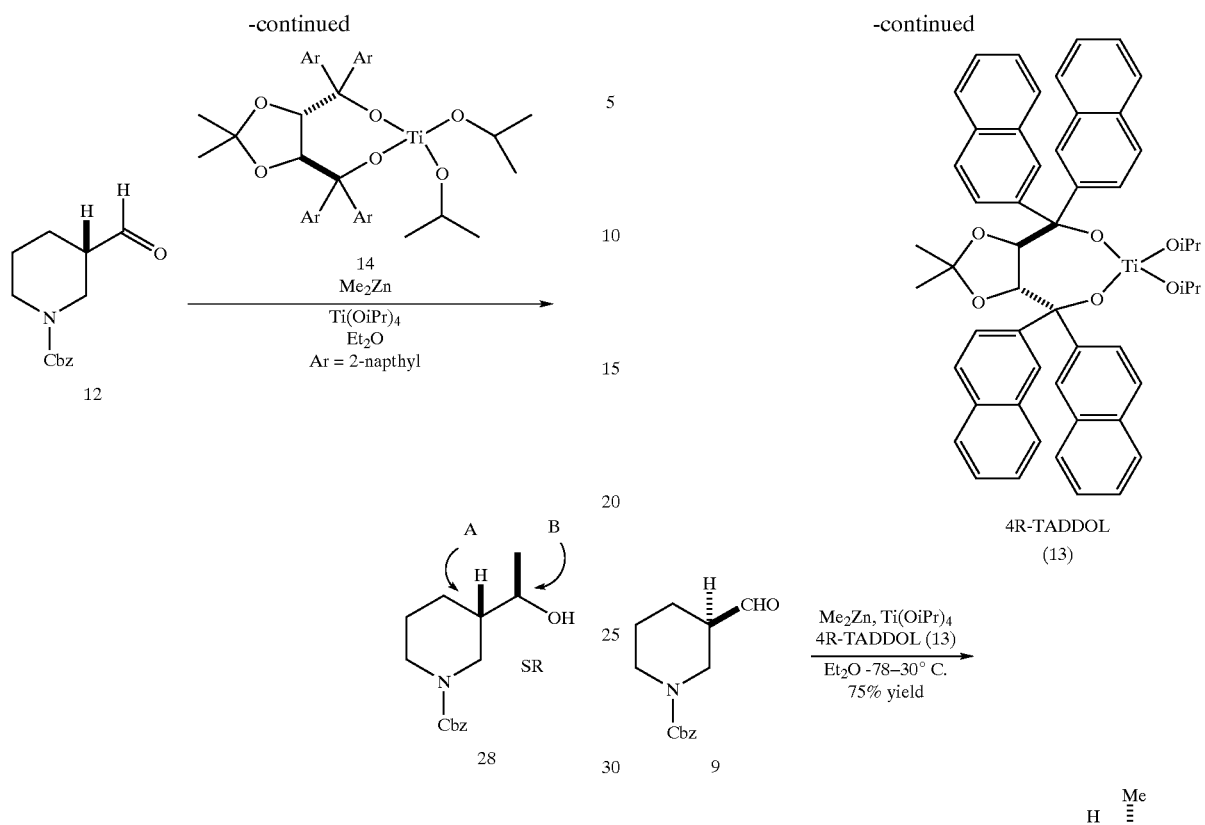

In certain embodiments, the use of about 5 mol % to about 20 mol % TADDOL is preferred. In certain embodiments, the use of about 15 mol % TADDOL is preferred. In certain embodiments, the use of about 10 mol % TADDOL is preferred. In certain embodiments, the use of freshly distilled titanium tetraisopropoxide and dimethyl zinc is preferred. Furthermore, catalyst derived from recovered TADDOL ligand may be used with no loss in yields and selectivities.

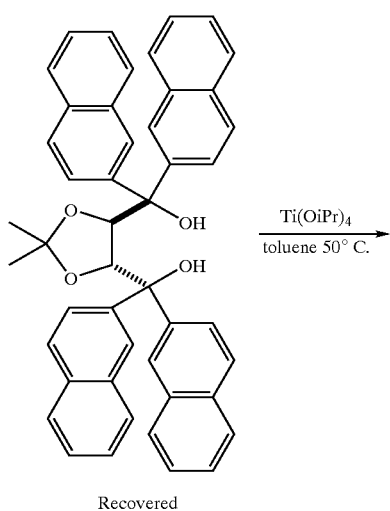

Figure 37:
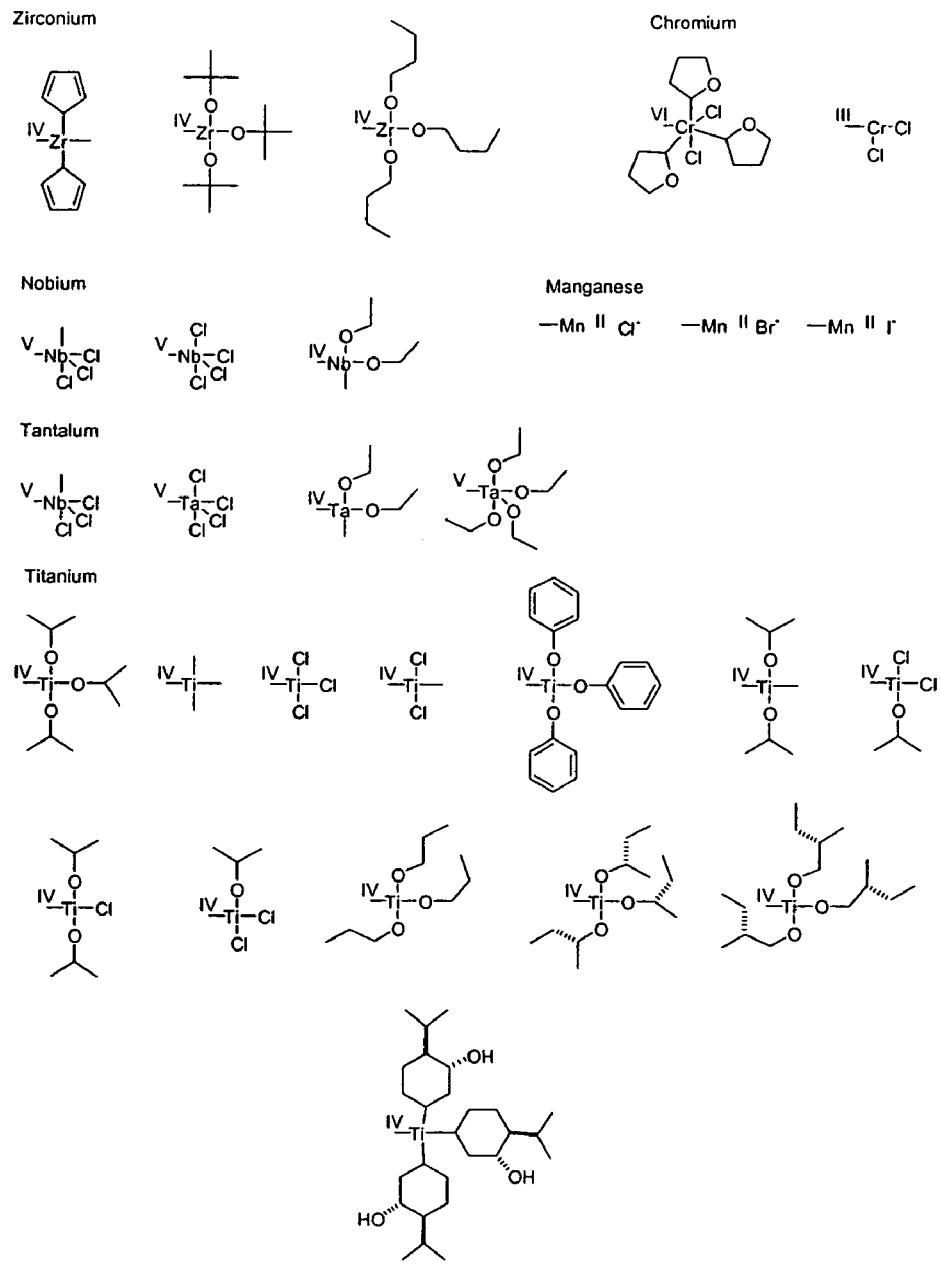
FIG. 37 depicts various sources of nucleophilic carbon that may be utilized in the asymmetric synthetic methods of the present invention.
Figure 38:
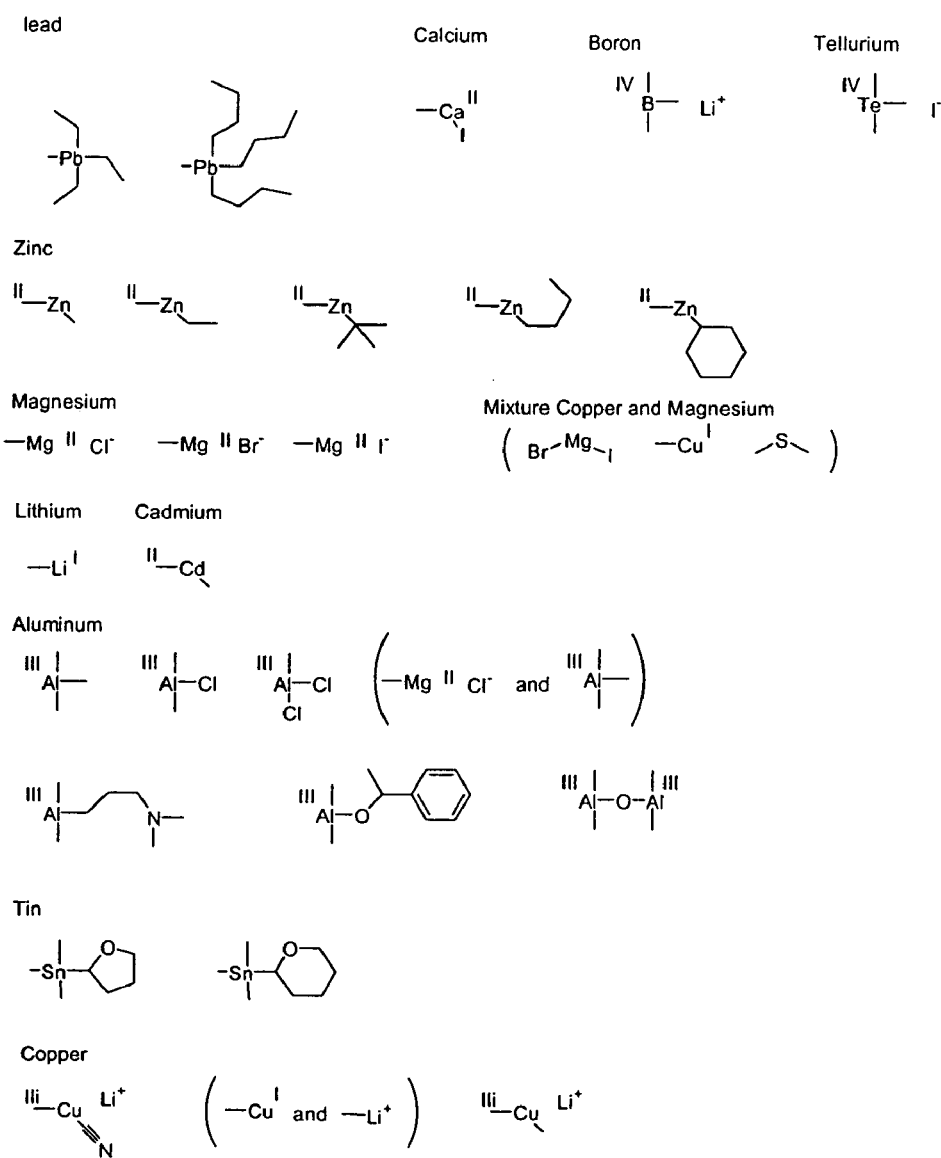
FIG. 38 depicts various sources of nucleophilic carbon that may be utilized in the asymmetric synthetic methods of the present invention.

It is anticipated that other chiral catalysts and reagents designed to stereoselectively add alkyl groups, such as methyl, to aldehydes will work in the methods of the present invention. For a recent review, which is hereby expressly incorporated by reference, see: Pu, L, Yu, H.-B. "Catalytic Asymmetric Organozinc Additions to Carbonyl Compounds" Chem. Rev. 2001, 101, 757–824. In other words, many different chiral ligands may be used in conjunction with a transition metal to catalyze this transformation. Examples of such catalysts and/or ligands include chiral amino alcohols, chiral iminyl alcohols, chiral amino thiols, chiral disulfides, chiral diselenides, chiral amines, chiral diols, chiral sulfonamides, chiral phosphoramides, chiral ligands attached to solid supports, chiral dendrites, and chiral polymers. Various examples of each type of ligand are depicted in FIGS. 20–36. The catalysts for this transformation may be isolated or generated in situ by a complex of any of the above ligands with titanium, zinc, iron, ruthenium, chromium, zirconium, nobium, manganese, lead, calcium, boron, lithium, cadmium, aluminum, tin, or copper. There are many sources of nucleophilic carbon for this transformation, e.g., dimethyl zinc; various examples of nucleophilic carbon sources are depicted in FIGS. 37 and 38.

Once both stereocenters are established, completion of the synthesis to selectively form 1, 2, 3 and 4 is straightforward (see FIGS. 7–10). Alcohols 15, 16, 27 and 28 were converted to the corresponding mesylates with mesyl chloride. $S_N2$ displacement with aniline provided amines 17, 19, 33 and 34, respectively. No loss of enantiopurity was observed for the aniline displacement reaction.

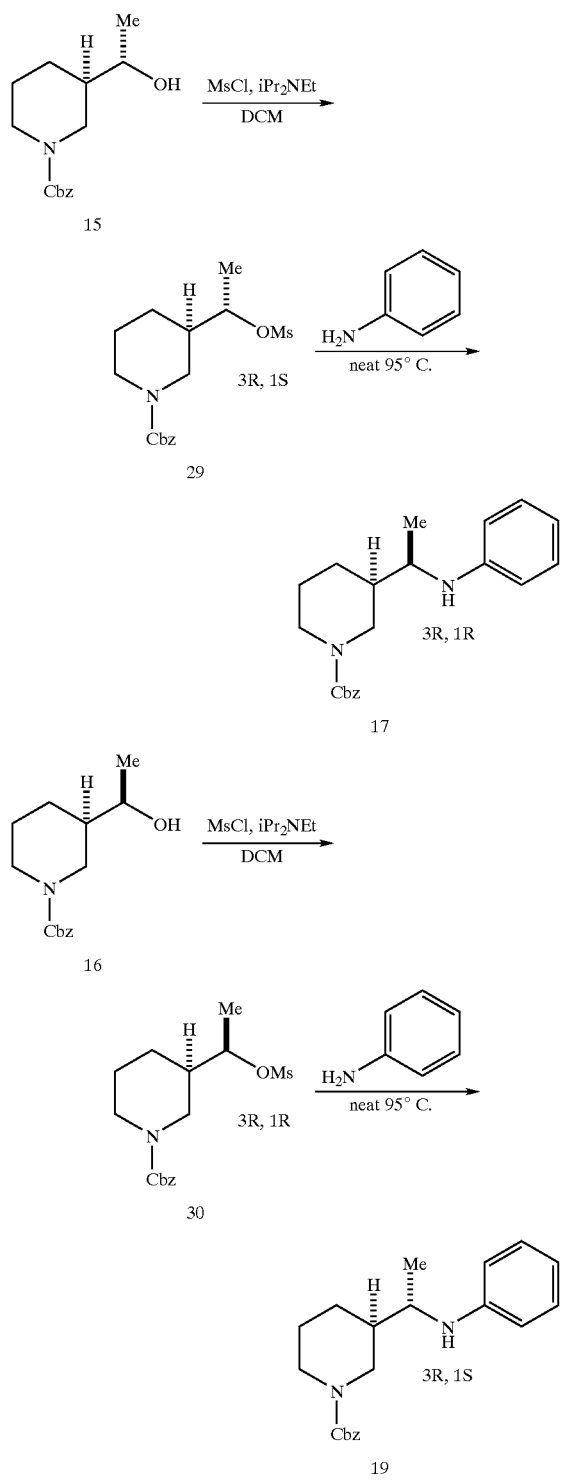

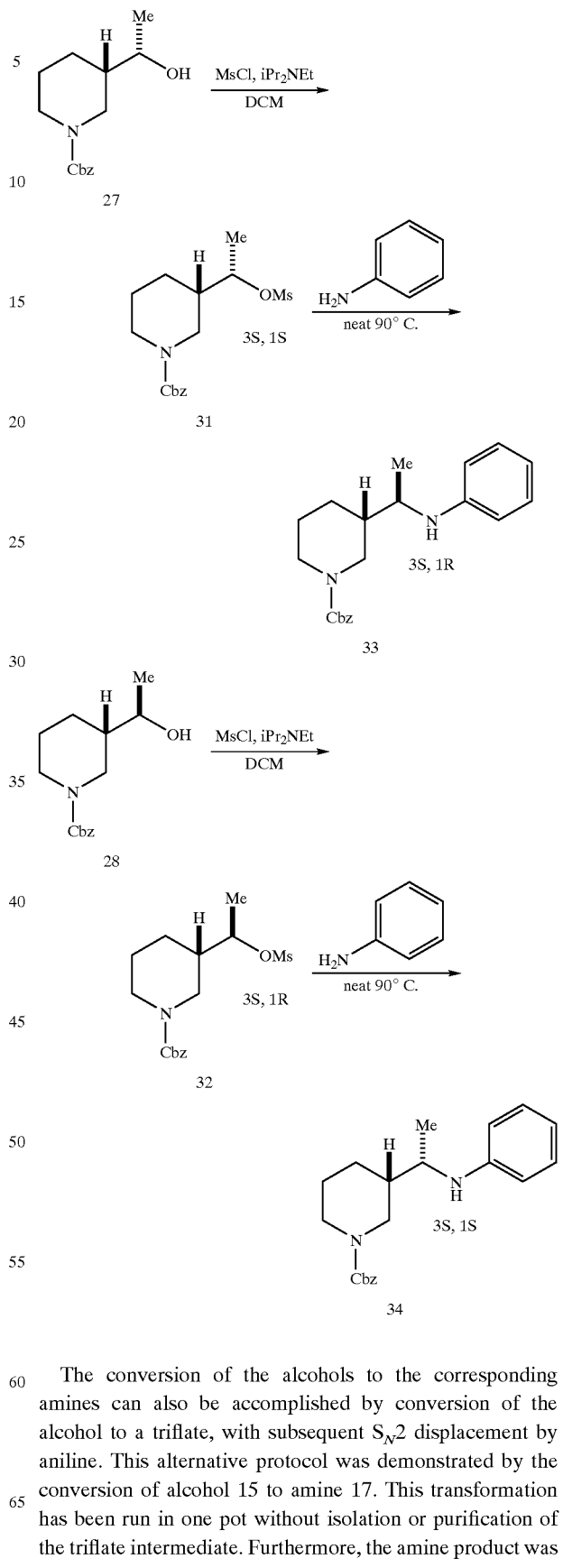

The conversion of the alcohols to the corresponding amines can also be accomplished by conversion of the alcohol to a triflate, with subsequent $S_N2$ displacement by aniline. This alternative protocol was demonstrated by the conversion of alcohol 15 to amine 17. This transformation has been run in one pot without isolation or purification of the triflate intermediate. Furthermore, the amine product was easily obtained with high levels of purity, allowing for higher yields in the subsequent acylation step described below.

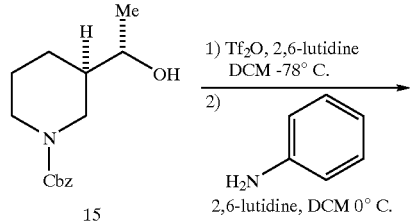

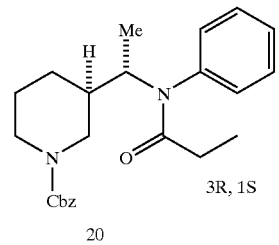

Acylation of amines 17, 19, 33, and 34 with propionyl chloride provided amides 18, 20, 35 and 36. Acylation with other reagents such as propionic anhydride or propionic acids activated with a reagent such as PyBOP are also anticipated to work for this transformation.

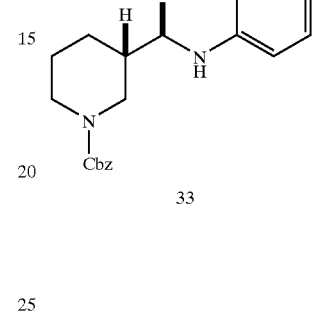

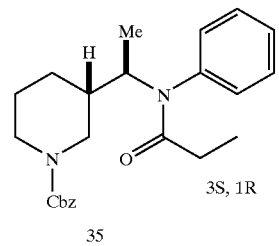

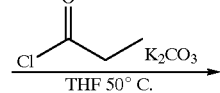

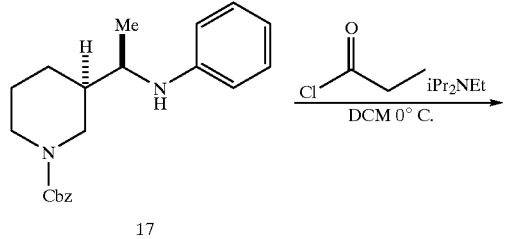

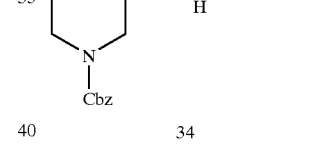

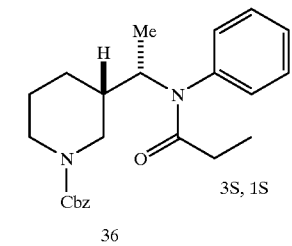

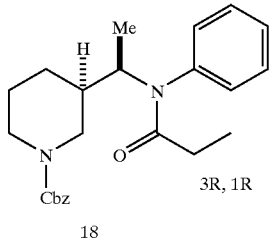

Cbz deprotection was straightforward, as was represented by the conversions of 18 and 20 to secondary amines 37 and 38.

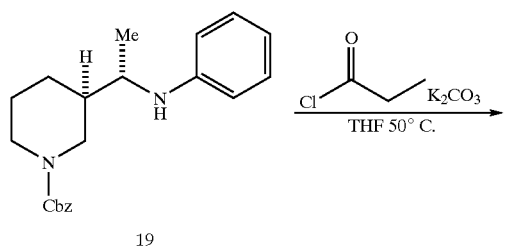

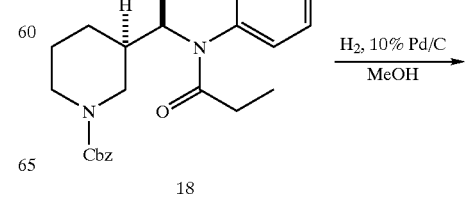

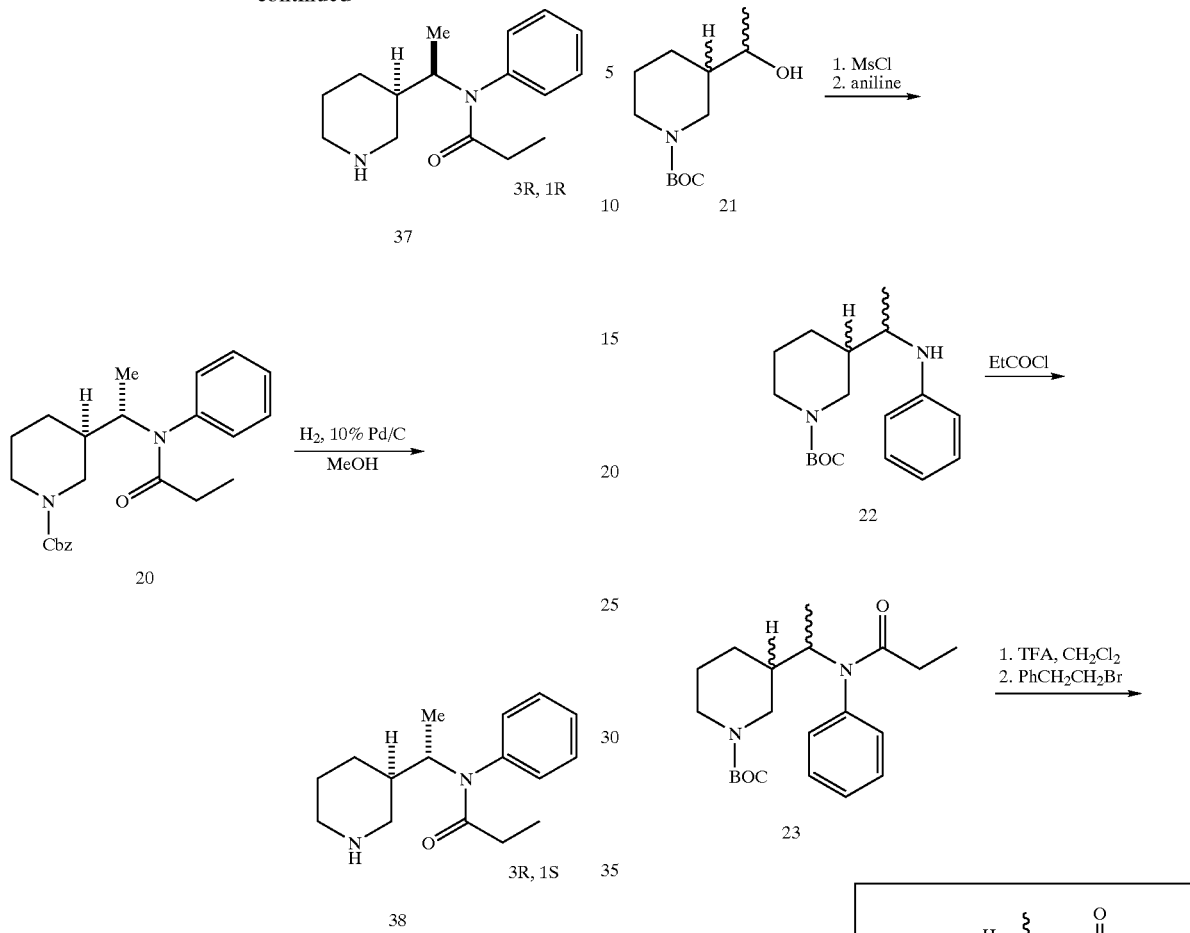

These secondary amines may be converted to a variety of products, such as amides, sulfonamides, ureas, and carbamates. In certain preferred embodiments, the secondary amines are converted to tertiary amine products, such as compounds 1, 2, 3 and 4. In the case of 1–4, treatment with a phenethylhalide and a base such as K$_2$CO$_3$ may be used. This was demonstrated by the chemistry described below for the synthesis of a mixture of 1–4. Of course, one of ordinary skill in the art of organic chemistry will recognize that other methods, e.g., reductive amination, may be used to achieve these alkylations.

As was noted above, it is anticipated that the chemistries described above should work well with BOC protected amine compounds. This was demonstrated in the non-selective synthesis of 24, a mixture of isomers 1–4. 24 was synthesized from alcohol 21, which differs from 15 and 16 only in its carbamate protecting group (BOC instead of Cbz), and its lack of enantio- and diastereo-purity. Compound 21 was obtained by Grignard addition to the corresponding aldehyde. For the stereoselective chemistry described above, N-Cbz protection was chosen over N-BOC protection based only on the fact that the Cbz-compounds have a better chromophore (compared to BOC protected compounds) for analytical HPLC ee and de determinations of intermediates on the route to compounds 1 to 4.

Figure 39:
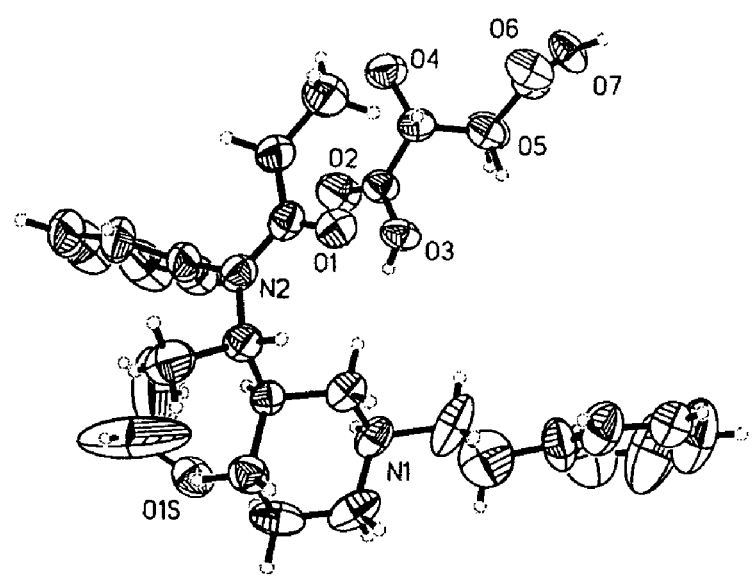
FIG. 39 depicts an ORTEP drawing of the X-ray crystal structure of compound 2.

Compound 24 was separated into the four individual isomers, 1–4, by achiral and chiral chromatographic methods. Furthermore, all four isomers (1–4) were separated by analytical chiral HPLC methods. The absolute stereochemistry of all four isomers (obtained by separation of 24) was determined using x-ray crystallographic and other analytical methods. The absolute stereochemistry of 2 was determined by x-ray crystallography. FIG. 39. This information was then combined with other analytical methods to determine the absolute stereochemistry of all four isomers (1 to 4). Using these authentic samples, the stereochemistry assigned for the products 15, 16, 27 and 28 were confirmed. Analytical HPLC comparison of 2, synthesized stereoselectively by the methods described herein, matched the known sample of 2, synthesized by separation of 24.

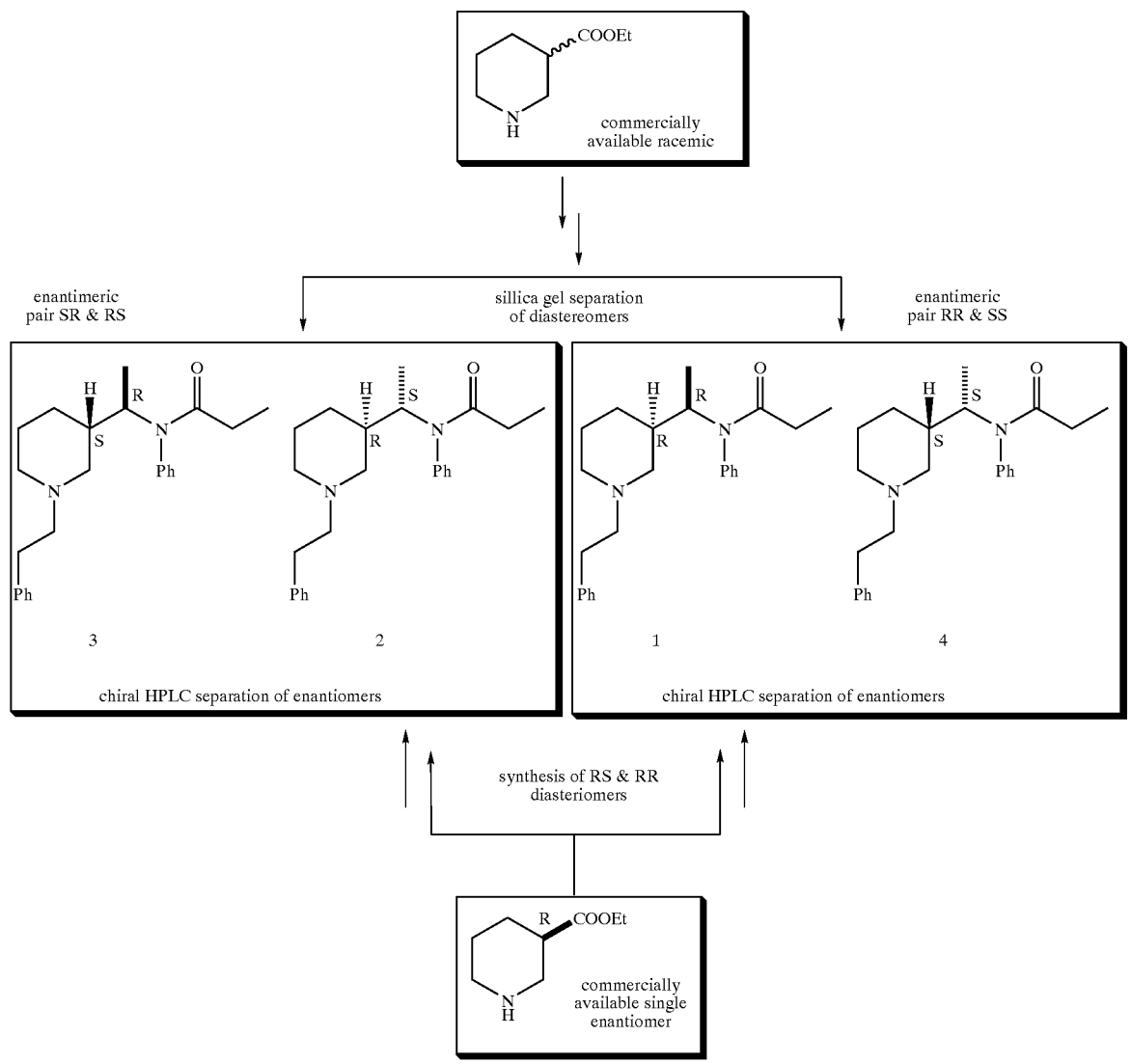

Combinatorial Libraries

The subject methods may be practiced in a combinatorial sense to prepare combinatorial libraries of substituted piperidines for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) Trends Anal. Chem. 14:83; the Affymax U.S. Pat. Nos. 5,359,115 and 5,362,899: the Ellman U.S. Pat. No. 5,288,514: the Still et al. PCT publication WO 94/08051; Chen et al. (1994) JACS 116: 2661: Kerr et al. (1993) JACS 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

A. Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) PNAS 81:3998–4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) Tetrahedron Lett 31:5811–5814; Valerio et al. (1991) Anal Biochem 197:168–177; Bray et al. (1991) Tetrahedron Lett 32:6163–6166).

C) Divide-Couple-Recombine

In yet another embodiment, a variegated library of compounds can be provided on a set of beads utilizing the strategy of divide-couple-recombine (see, e.g., Houghten (1985) PNAS 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) PNAS 82:5131–5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) Annu Rep Med Chem 26:271–280; Fodor, S. P. A. (1991) Science 251:767; Pirrung et al. (1992) U.S. Pat. No. 5,143,854; Jacobs et al. (1994) Trends Biotechnol 12:19–26). The spatial resolution of photolithography affords miniaturization. This technique can be carried out through the use protection/deprotection reactions with photolabile protecting groups.

The key points of this technology are illustrated in Gallop et al. (1994) J Med Chem 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-oligomers

The principle of using oligonucleotides to encode combinatorial synthetic libraries was described in 1992 (Brenher et al; (1992) PNAS 89:5381–5383), and an example of such a library appeared the following year (Needles et al. (1993) PNAS 90:10700–10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) *J Am Chem Soc* 115:2529–2531), orthogonality in synthesis is achieved by employing acid-labile protection for the coding strand and base-labile protection for the compound strand.

In an alternative approach (Nikolaiev et al. (1993) *Pept Res* 6:161–170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) *Tetrahedron Lett* 32:3891–3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-sequenceable Tagging: Binary Encoding

An alternative form of encoding the test compound library employs a set of non-sequencable electrophoric tagging molecules that are used as a binary code (Ohlmeyer et al. (1993) *PNAS* 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J Org Chem* 59:4723–4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027–6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

EXEMPLIFICATION

The invention now being generally described, it will be more readily understood by reference to the following examples, which are included merely for purposes of illustration of certain aspects and embodiments of the present invention, and are not intended to limit the invention.

EXAMPLE 1

Synthesis of (3R)-Piperidine-1,3-dicarboxylic acid 1-benzyl ester 3-ethyl ester (7)

Protocol 1

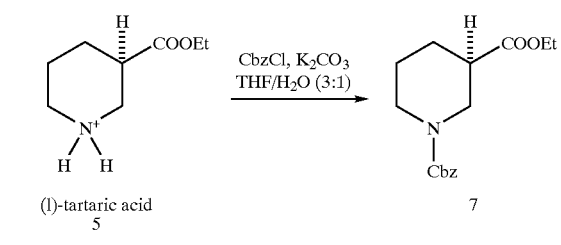

(R)-Ethyl nipecotate-(l)-tartrate salt (15.0 g, 48.81 mmol) was dissolved in 61 mL of 3:1 THF:H₂O, and the solution was stirred under N₂ at 0° C. 20.24 g (146.4 mmol) of K₂CO₃ was added in one portion, then 8.33 mL (51.25 mmol) of (benzyoxy)carbonyl chloride was added dropwise. The reaction was allowed to warm to room temperature with stirring overnight. The solvent was then removed, and EtOAc and H₂O were added. The organic layer was separated, washed with brine, dried with sodium sulfate, filtered, and concentrated. The crude material was used without further purification.

Protocol 2

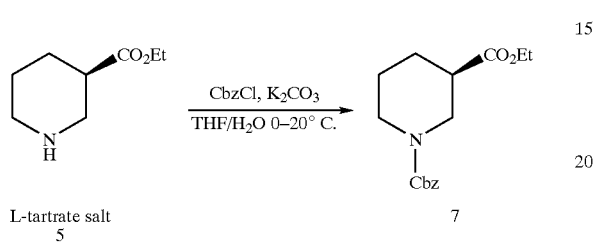

L-tartrate salt
5
7

A 1.0 L round-bottom flask was charged with K₂CO₃ (29.2 g; 171 mmol), piperidine (50 g; 163 mmol), and a 1:1 mixture of THF/H₂O (800 mL). A 150 mL addition funnel was placed on the flask and charged with CbzCl (29.2 g, 171 mmol). The flask was cooled to 0° C. and then CbzCl was added dropwise over 5 minutes. The reaction mixture was warmed to 20° C. and stirred for 1 h. The reaction mixture was extracted with EtOAc (500 mL) and the organic layer was washed with water (500 mL), saturated NaCl (500 mL), dried (MgSO₄), filtered and concentrated in vacuo. The crude material was purified by flash chromatography (silica gel, hexanes/EtOAc 9:1 to 4:1) to give pure product (49.3 g, 100% yield). ¹H-NMR (300 MHz) δ (ppm) 7.40 (m; 5H); 5.17 (s; 2H); 4.19 (q; 2H); 4.04 (m; 1H); 3.12 (m; 1H); 2.95 (m; 1H); 2.48 (m; 1H); 2.08 (m; 1H); 1.75 (m; 3H); 1.53 (m; 1H); 1.28 (t; 3H).

EXAMPLE 2

Synthesis of (3S)-Piperidine-1,3-dicarboxylic acid 1-benzyl ester 3-ethyl ester (10)

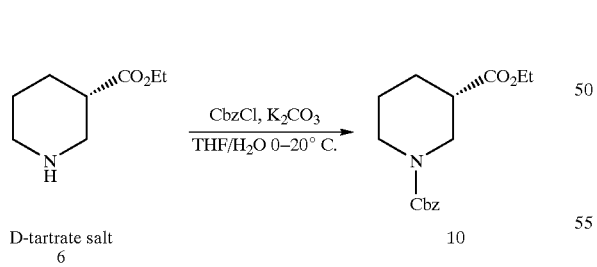

D-tartrate salt
6
10

A 1.0 L round-bottom flask was charged with K₂CO₃ (29.2 g; 171 mmol), piperidine (50 g; 163 mmol), and a 1:1 mixture of THF/H₂O (800 mL). A 150 mL addition funnel was placed on the flask and charged with CbzCl (29.2 g, 171 mmol). The flask was cooled to 0° C. and then CbzCl was added dropwise over 5 minutes. The reaction mixture was warmed to 20° C. and stirred for 1 h. The reaction mixture was extracted with EtOAc (500 mL) and the organic layer was washed with water (500 mL), saturated NaCl (500 mL), dried (MgSO₄), filtered and concentrated in vacuo. The crude material (49.3 g, 100% yield) was carried on without further purification.

EXAMPLE 3

Synthesis of 3-hydroxymethyl-piperidine-1-carboxylic acid benzyl ester (8)

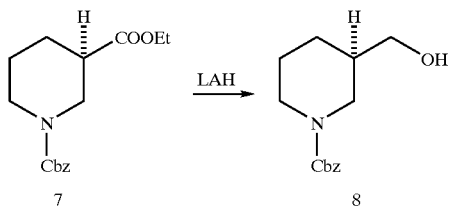

7
8

Piperidine-1,3-dicarboxylic acid 1-benzyl ester 3-ethyl ester (7) (1.5 g, 5.83 mmol) was dissolved in 5.8 mL of anhydrous THF, and the reaction was stirred under N₂ at −5° C. while lithium aluminum hydride dissolved in THF (7.0 mL, 1.0M) was added dropwise by addition funnel over 30 minutes. When the reaction was complete by TLC (10 min.), H₂O (0.6 mL), then 10% NaOH (1.5 mL), then H₂O (0.6 mL) were added, and the reaction was stirred for about 45 minutes. The salts were removed by filtration and the solution was dried with sodium sulfate, filtered, and concentrated. The crude material was purified using an ISCO CombiFlash flash column (silica, 80:20 Hexane:EtOAc to 40:60 Hexane:EtOAc) to achieve 1.24 g of pure 8 (66% yield).

EXAMPLE 4

Synthesis of (3R)-Piperidine-1,3-dicarboxylic acid 1-benzyl ester (25)

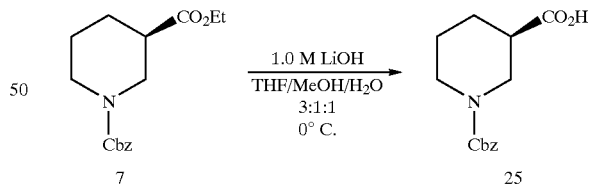

7
25

A 1.0 L round-bottom flask was charged with ester (163 mmol), THF (360 mL), MeOH (120 mL), and water (120 mL). The flask was cooled to 0° C. and a solution of LiOH (1.0 M in water, 325 mL; 325 mmol) was added slowly dropwise. The reaction was stirred overnight at 0° C. and then quenched with 10% HCl slowly dropwise at 0° C. until the pH~3. The mixture was extracted with EtOAc (500 mL), washed with water (500 mL), saturated NaCl (500 mL), dried (Na₂SO₄), filtered and concentrated in vacuo. The crude material (40.5 g, 95% yield) was carried on without further purification.

EXAMPLE 5

Synthesis of (3S)-Piperidine-1,3-dicarboxylic acid 1-benzyl ester (26)

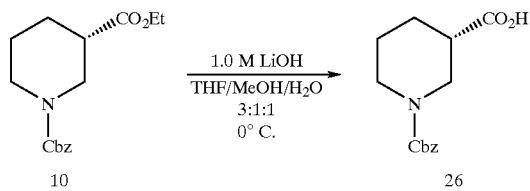

A 1.0 L round-bottom flask was charged with ester (49.3 g, 163 mmol), THF (360 mL), MeOH (120 mL), and water (120 mL) The flask was cooled to 0° C. and a solution of LiOH (1.0 M in water; 325 mL; 325 mmol) was added slowly dropwise. The reaction was stirred overnight at 0° C. and then quenched with 10% HCl slowly dropwise at 0° C. until the pH~3. The mixture was extracted with EtOAc (500 mL), washed with water (500 mL), saturated NaCl (500 mL), dried ($Na_2SO_4$), filtered and concentrated in vacuo. The crude material (39.8 g, 93% yield) was carried on without further purification.

EXAMPLE 6

Synthesis of (3R)-3-Hydroxymethyl-piperidine-1-carboxylic acid benzyl ester (8)

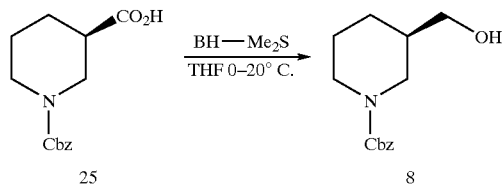

A 1.0 L round-bottom flask was charged with acid (40.5 g; 154 mmol) and THF (600 mL). The reaction mixture was cooled to 0° C. and a 150 mL addition was charged with borane-dimethyl sulfide (10.0 M neat; 46.2 mL; 462 mmol). The borane was added slowly dropwise at 0° C. and the reaction mixture was stirred while warming to 20° C. for 2 hours. The reaction mixture was cooled to 0° C. and quenched slowly with 10% HCl until evolution of gas had ceased. The reaction mixture was stirred a further 30 minutes and then diluted with 10% NaOH (500 mL) and extracted with EtOAc (500 mL). The organic layer was washed with saturated NaCl (500 mL), dried ($Na_2SO_4$), filtered and concentrated in vacuo. The crude material was purified by flash chromatography (silica gel, hecanes/EtOAc 1:1 to 1:2) to give pure product (38.2 g, 100% yield). The enantiomeric purity was 99.16% ee as determined by chiral HPLC analysis. $^1$H-NMR (300 MHz) δ (ppm) 7.38 (m; 5H); 5.17 (s; 2H); 4.01 (m; 1H); 3.88 (bs; 1H); 3.51 (d; 2H); 3.02 (m; 1H); 2.84 (m; 1H); 1.78 (m; 4H); 1.48 (m; 1H); 1.23 (m; 1H). $^{13}$C-NMR (300 MHz) δ (ppm) 155.7; 137.1; 128.7; 128.2; 127.9; 67.2; 64.8; 53.9; 47.3; 45.0; 38.7; 27.2; 24.6.

EXAMPLE 7

Synthesis of (3S)-3-Hydroxymethyl-piperidine-1-carboxylic acid benzyl ester (11)

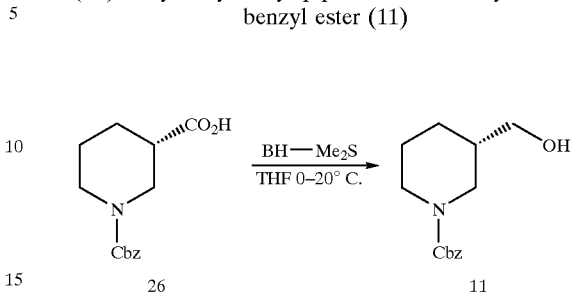

A 1.0 L round-bottom flask was charged with acid (39.8 g, 151 mmol) and THF (600 mL). The reaction mixture was cooled to 0° C. and a 150 mL addition was charged with borane-dimethyl sulfide (10.0 M neat; 45 mL; 450 mmol). The borane was added slowly dropwise at 0° C. and the reaction mixture was stirred while warming to 20° C. for 2 hours. The reaction mixture was cooled to 0° C. and quenched slowly with 10% HCl until evolution of gas had ceased. The reaction mixture was stirred a further 30 minutes and then diluted with 10% NaOH (500 mL) and extracted with EtOAc (500 mL). The organic layer was washed with saturated NaCl (500 mL), dried ($Na_2SO_4$), filtered and concentrated in vacuo. The crude material was purified by flash chromatography (silica gel, hexanes/EtOAc 1:1 to 1:2) to give pure product (36.0 g, 96% yield). The enantiomeric purity was 99.58% ee as determined by chiral HPLC analysis. $^1$H-NMR (300 MHz) δ (ppm) 7.40 (m; 5H); 5.14 (s; 2H); 4.01 (m; 1H); 3.86 (bs; 1H); 3.50 (d; 2H); 3.11 (m; 1H); 2.76 (m; 1H); 1.75 (m; 4H); 1.43 (m; 1H); 1.25 (m; 1H).

EXAMPLE 8

Synthesis of 3-formyl-piperidine-1-carboxylic acid benzyl ester (9)

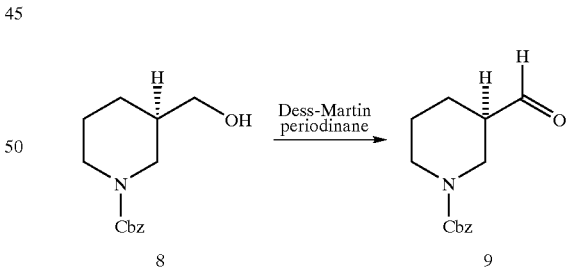

To a stirring, 0° C. solution of 0.303 g (1.20 mmol) of 3-hydroxymethyl-piperidine-1-carboxylic acid benzyl ester (8) in $CH_2Cl_2$ (4.0 mL) was added 0.630 g (1.44 mmol) of Dess-Martin periodinane, and the solution was stirred under $N_2$. When the reaction was complete by TLC (about 30 min.), the reaction was concentrated, and then $Et_2O$ was added. After standing for about 15 min., the reaction was filtered through Celite wet with $Et_2O$, rinsed with $Et_2O$, and concentrated. The crude reaction was purified by column chromatography (florisil®, 100–200 mesh, 2:1 Hexane:EtOAc) to achieve pure 9.

EXAMPLE 9

Synthesis of (3R)-Formyl-piperidine-1-carboxylic acid benzyl ester (8)

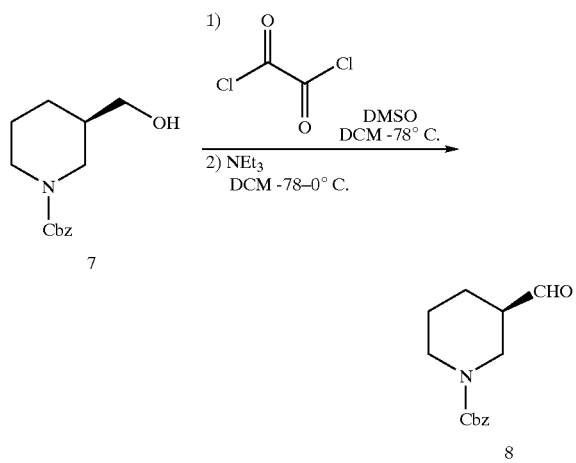

A 500 mL RB flask was charged with DCM (300 mL) and oxalyl chloride (5.8 mL; 66 mmol) and then cooled to −78° C. A 150 mL addition funnel was charged with DMSO (8.5 mL; 120 mmol) and DCM (30 mL). The DMSO was added slowly dropwise at −78° C. and the reaction mixture was stirred for 30 min. The 150 mL addition funnel was charged with alcohol (16.5 g; 60 mmol) and DCM (30 mL). The alcohol was added slowly dropwise at −78° C. and the reaction mixture was stirred for 10 min. The 150 mL addition funnel was charged with triethyl amine (42 mL; 300 mmol). The amine was added slowly dropwise at −78° C. and the reaction mixture was stirred while warming to 0° C. for 30 min. The reaction mixture was quenched with water (500 mL) and extracted with DCM (500 mL). The organic layer was washed with 1.0 M $NaHSO_4$ (500 mL), dried ($Na_2SO_4$), filtered and concentrated in vacuo. The crude material was purified by flash chromatography (florosil, hexanes/EtOAc 2:1) to give pure product (15.1 g, 100% yield). Note: The aldehyde was either used immediately in the next step or stored at −20° C. under an argon atmosphere. $^1$H-NMR (300 MHz) δ (ppm) 9.72 (s; 1H); 7.38 (m; 5H); 5.17 (s; 2H); 4.05 (m; 1H); 3.79 (m; 1H); 3.41 (dd; 1H); 3.19 (m; 1H); 2.48 (m; 1H); 2.02 (m; 1H); 1.73 (m; 2H); 1.58 (m; 1H).

EXAMPLE 10

Synthesis of (3S)-Formyl-piperidine-1-carboxylic acid benzyl ester (12)

A 250 mL RB flask was charged with DCM (100 mL) and oxalyl chloride (2.31 mL; 26.4 mmol) and then cooled to −78° C. A 25 mL addition funnel was charged with DMSO (3.42 mL; 48.2 mmol in 15 mL DCM). The DMSO was added slowly dropwise at −78° C. and the reaction mixture was stirred for 30 min. The 25 mL addition funnel was charged with alcohol (6.0 g; 24.1 mmol in 15 mL DCM. The alcohol was added slowly dropwise at −78° C. and the reaction mixture was stirred for 10 min. The 25 mL addition funnel was charged with triethyl amine (16.8 mL; 120 mmol). The amine was added slowly dropwise at −78° C. and the reaction mixture was stirred while warming to 0° C. for 30 min. The reaction mixture was quenched with water (200 mL) and extracted with DCM (100 mL). The organic layer was washed with 1.0 M $NaHSO_4$ (250 mL), dried ($Na_2SO_4$), filtered and concentrated in vacuo. The crude material was purified by flash chromatography (florosil, hexanes/EtOAc 2:1) to give pure product (5.53 g, 92.7% yield). The aldehyde was either used immediately in the next step or stored at −20° C. under an argon atmosphere. $^1$H-NMR (300 MHz) δ (ppm) 9.74 (5; 1H); 7.37 (m; 5H); 5.15 (s; 2H); 4.08 (m; 1H); 3.76 (m; 1H); 3.41 (dd; 1H); 3.17 (m; 1H); 2.46 (m; 1H); 2.02 (m; 1H); 1.73 (m; 2H); 1.58 (m; 1H).

EXAMPLE 11

Synthesis of 2-napthyl TADDOL catalyst (13)

Protocol 1

Using Schlenck glassware and air-free conditions, freshly distilled titanium tetraisopropoxide (0.079 mL, 0.267 mmol) was added to (4R-trans)-2,2-Dimethyl-α,α,α',α'-tetra-(2-napthyl)-1,3-dioxolane-4,5-dimethanol (0.162 g, 0.243 mmol) in anhydrous toluene freshly distilled from sodium/benzophenone (2.21 mL), and the reaction was stirred at 40° C. for 5 hours. The reaction was then concentrated in vacuo, stored under argon until it was used without further purification.

Protocol 2

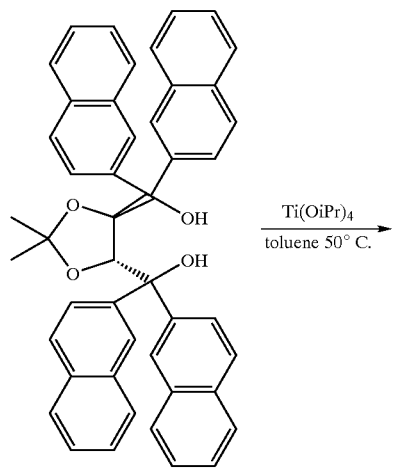

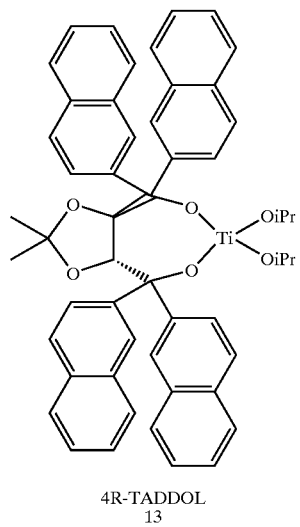

4R-TADDOL
13

A flame dried 200 mL round-bottom flask was purged with argon and then charged with 4R-diol (4.04 g; 6.1 mmol), toluene (60 mL; pre-dried with 4 Å molecular sieves) and titanium (IV) isopropoxide (1.79 mL; 6.1 mmol). The reaction mixture was heated to 50° C. and stirred for 4 h under an argon atmosphere. The toluene was removed in vacuo to give the catalyst as a pale yellow solid. The catalyst was kept under vacuum and then used immediately after purging with argon.

Protocol 3

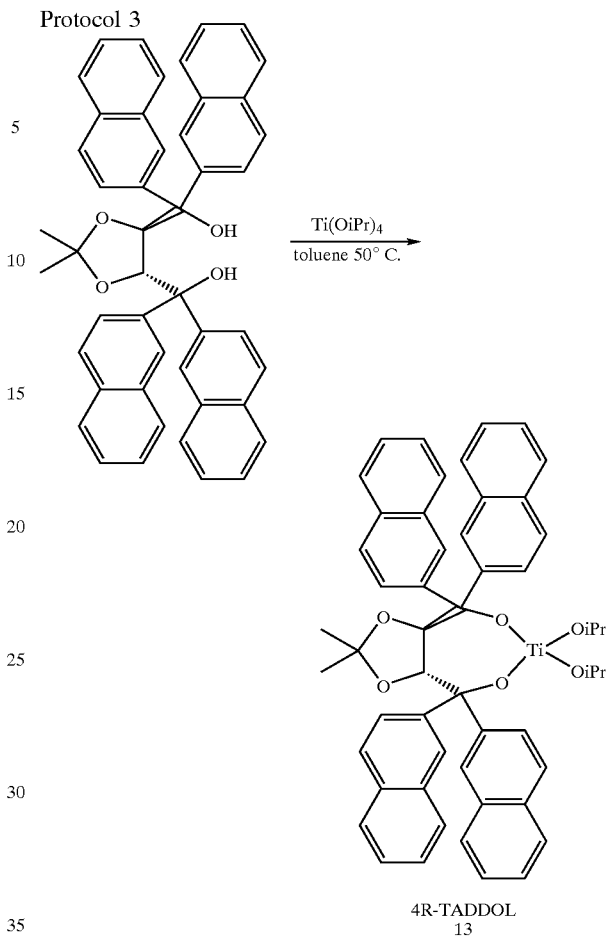

4R-TADDOL
13

A flame dried 200 mL round-bottom flask was purged with argon and then charged with 4R-diol (2.02 g; 3.0 mmol), toluene (30 mL; pre-dried with 4 Å molecular sieves) and titanium (IV) isopropoxide (0.90 mL; 3.0 mmol). The reaction mixture was heated to 50° C. and stirred for 5 h under an argon atmosphere. The toluene was removed in vacuo to give the catalyst as a pale yellow solid. The catalyst was kept under vacuum and then used immediately after purging with argon.

EXAMPLE 12

Synthesis of (R,S)-3-(1-Hydroxyethyl)-piperidine-1-carboxylic acid benzyl ester (15)

Protocol 1

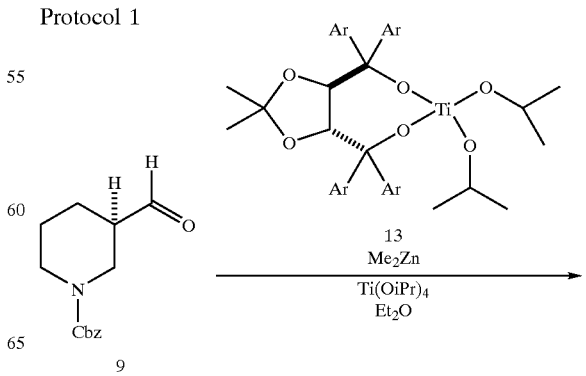

-continued

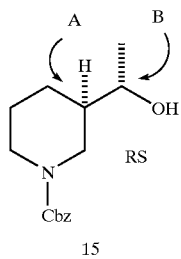

Using Schlenck glassware and air-free conditions, anhydrous ethyl ether freshly distilled from sodium/benzophenone (2.43 mL) was added to catalyst 13 prepared according to Example 11, protocol 1. Freshly distilled titanium tetraisopropoxide (0.430 mL, 1.46 mmol) was added, and the reaction was cooled to −78° C. Commercial Me$_2$Zn (1.21 mL, 2 M in toluene) was added, and the reaction was stirred at −78° C. for 1 hour. Aldehyde 9 (0.300 g, 1.21 mmol) in Et$_2$O (0.3 mL) was added, and the reaction was warmed to −30° C. and stirred overnight. The reaction was then quenched at −30° C. with saturated aqueous NH$_4$Cl. Et$_2$O was added, and the reaction was filtered through Celite wet with Et$_2$O. The reaction was dried with sodium sulfate, filtered, concentrated, and purified using an ISCO Combi-Flash column (silica, 2:1 Hexane:EtOAc) to obtain 15 (0.162 g, 51%). HLPC analysis of the product presented in the Figures. $^1$H NMR (CDCl$_3$, 300 MHz) 7.43–7.31 (5H, broad s), 5.16 (2H, s), 4.30–3.60 (2H, broad m), 3.63 (1H, dq, J=6.4, 6.4 Hz), 3.30–2.70 (2H, broad s), 2.15–1.90 (1H, broad s), 1.84–1.72 (1H, m), 1.76–1.56 (1H, m), 1.58–1.36 (2H, m), 1.23 (3H, d, J=6.4 Hz) ppm. $^{13}$C NMR (CDCl$_3$, 75 MHz) 155.81, 137.04, 128.61, 128.08, 127.93, 68.35, 67.19, 46.61, 45.02, 43.25, 27.08, 24.37, 20.95 ppm. LRMS m/z 263.68 (M$^+$, C$_{15}$H$_{21}$NO$_3$, requires 263.15.

Protocol 2

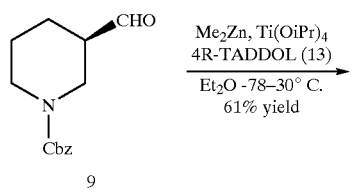

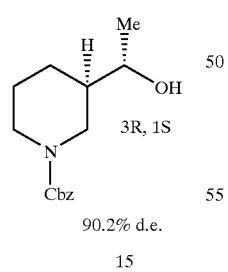

90.2% d.e.

15

A 200 mL round-bottom flask containing 4R-TADDOL (6.12 mmol) was charged with anhydrous ether (80 mL) and titanium isopropoxide (14.3 mL; 49 mmol). The solution was cooled to −78° C. and a 2.0 M solution of dimethyl zinc (40.5 mL; 81 mmol) was added. The solution was stirred at −78° C. for 1 h. To the solution was added aldehyde (10.0 g; 40.4 mmol) dissolved in ether (10 mL). The reaction mixture was warmed to −30° C. and stirred for 72 h. The reaction mixture was diluted with ether (500 mL) and quenched by the slow addition of saturated NH$_4$Cl (10 mL). The slurry was stirred at 20° C. for 10 min and then filtered through celite. The celite pad was washed with ether and the combined organic layers were concentrated in vacuo. The crude material was purified by flash chromatography (silica gel, hexanes/EtOAc 2:1 to 1:1) to give first, recovered 4R-ligand (3.62 g; 90% recovery) and second, pure product (6.51 g, 61% yield). The diastereomeric purity was 90.2% de as determined by achiral HPLC analysis. The enantiomeric purity of the major diastereomer was 99.8% ee as determined by chiral HPLC analysis. $^1$H-NMR (300 MHz) δ (ppm) 7.38 (m; 5H); 5.17 (s; 2H); 4.20 (m; 1H); 3.98 (m; 2H); 3.77 (m; 1H); 3.51 (m; 1H); 3.18 (m; 1H); 2.87 (m; 1H); 1.80 (m; 1H); 1.68 (m; 1H); 1.48 (m; 2H); 1.23 (d; 3H). $^{13}$C-NMR (300 MHz) δ (ppm) 155.8; 137.2; 128.7; 128.1; 128.0; 68.8; 67.2; 46.8; 45.0; 43.5; 27.2; 24.8; 21.1.

EXAMPLE 13

Synthesis of (3R)-3-((1S)-1-Hydroxy-ethyl)-piperidine-1-carboxylic acid benzyl ester (15) using catalyst (13) obtained from recycled diol ligand

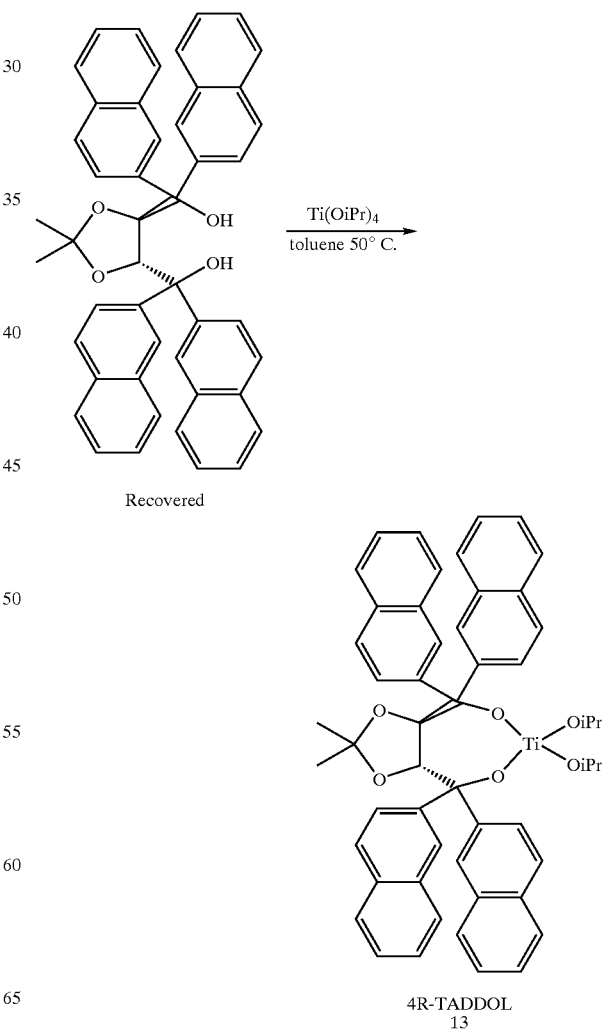

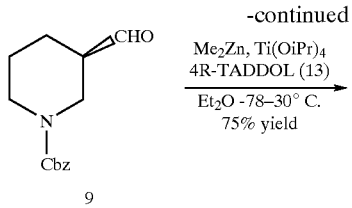

The 4R-Ligand recovered from the column chromatography can be used again without any loss in yield (75% yield) or diastereoselectivity (90.3% d.e.) of 15.

EXAMPLE 14

Synthesis of (3S)-3-((1S)-1-Hydroxy-ethyl)-piperidine-1-carboxylic acid benzyl ester (27)

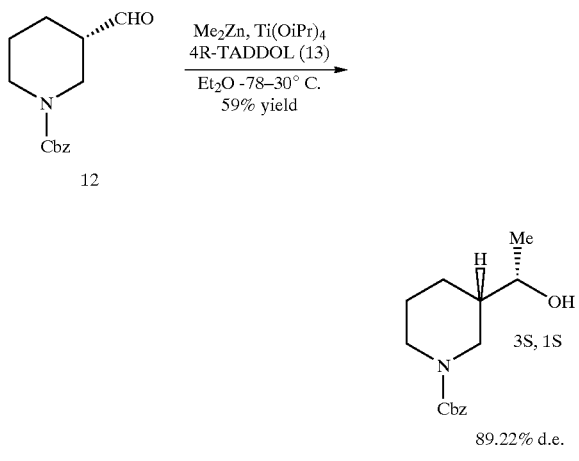

A 200 mL round-bottom flask containing 4R-TADDOL (3.0 mmol) was charged with anhydrous ether (40 mL) and titanium isopropoxide (7.16 mL; 24.5 mmol). The solution was cooled to −78° C. and a 2.0 M solution of dimethyl zinc (20.2 mL; 40.5 mmol) was added. The solution was stirred at −78° C. for 1 h. To the solution was added aldehyde (5.0 g; 20.2 mmol) dissolved in ether (2.5 mL). The reaction mixture was warmed to −30° C. and stirred for 72 h. The reaction mixture was diluted with ether (250 mL) and quenched by the slow addition of saturated NH$_4$Cl (5 mL). The slurry was stirred at 20° C. for 10 min and then filtered through celite. The celite pad was washed with ether and the combined organic layers were concentrated in vacuo. The crude material was purified by flash chromatography (silica gel, hexanes/EtOAc 2:1 to 1:1) pure product (3.15 g, 59% yield). The diastereomeric purity was 89.22% de as determined by achiral HPLC analysis. The enantiomeric purity of the major diastereomer was >98.9% ee as determined by chiral HPLC analysis. $^1$H-NMR (300 MHz) δ (ppm) 7.38 (m; 5H); 5.17 (s; 2H); 4.10 (m; 2H); 3.66 (m; 1H); 2.82 (m; 1H); 2.76 (m; 1H); 1.98 (m; 2H); 1.75 (m; 1H); 1.48 (m; 2H); 1.30 (m; 1H); 1.22 (d; 3H). $^{13}$C-NMR (300 MHz) δ (ppm) 155.7; 137.1; 128.7; 128.2; 128.0; 69.4; 67.3; 47.1; 44.9; 43.3; 25.8; 24.9; 21.1.

EXAMPLE 15

Synthesis of 2-napthyl TADDOL catalyst (14)

Protocol 1

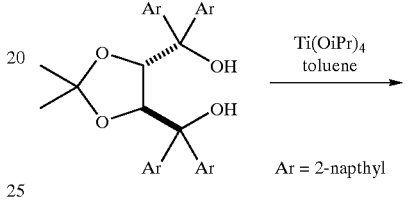

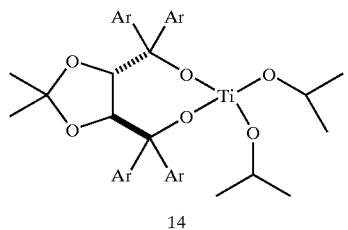

Using Schlenck glassware and air-free conditions, freshly distilled titanium tetraisopropoxide (0.079 mL, 0.267 mmol) was added to (4S-trans)-2,2-Dimethyl-α,α,α',α'-tetra-(2-napthyl)-1,3-dioxolane-4,5-dimethanol (0.162 g, 0.243 mmol) in anhydrous toluene freshly distilled from sodium/benzophenone (2.21 mL), and the reaction was stirred at 40° C. for 5 hours. The reaction was then concentrated in vacuo, stored under argon until it was used without further purification.

Protocol 2

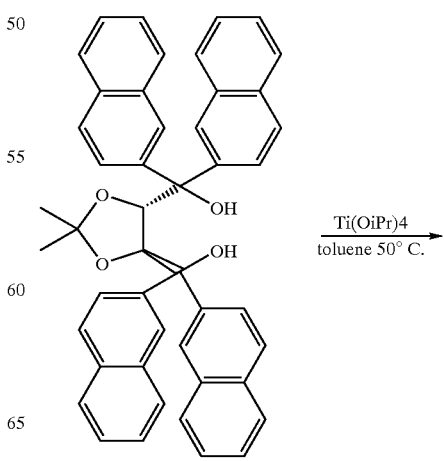

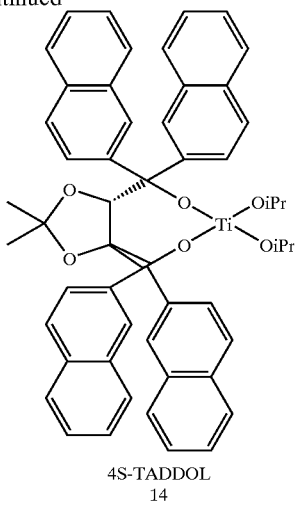

4S-TADDOL
14

A flame dried 200 mL round-bottom flask was purged with argon and then charged with 4S-diol (4.04 g; 6.1 mmol), toluene (60 mL; pre-dried with 4 Å molecular sieves) and titanium (IV) isopropoxide (1.79 mL; 6.1 mmol). The reaction mixture was heated to 50° C. and stirred for 4 h under an argon atmosphere. The toluene was removed in vacuo to give the catalyst as a pale yellow solid. The catalyst was kept under vacuum and then used immediately after purging with argon.

Protocol 3

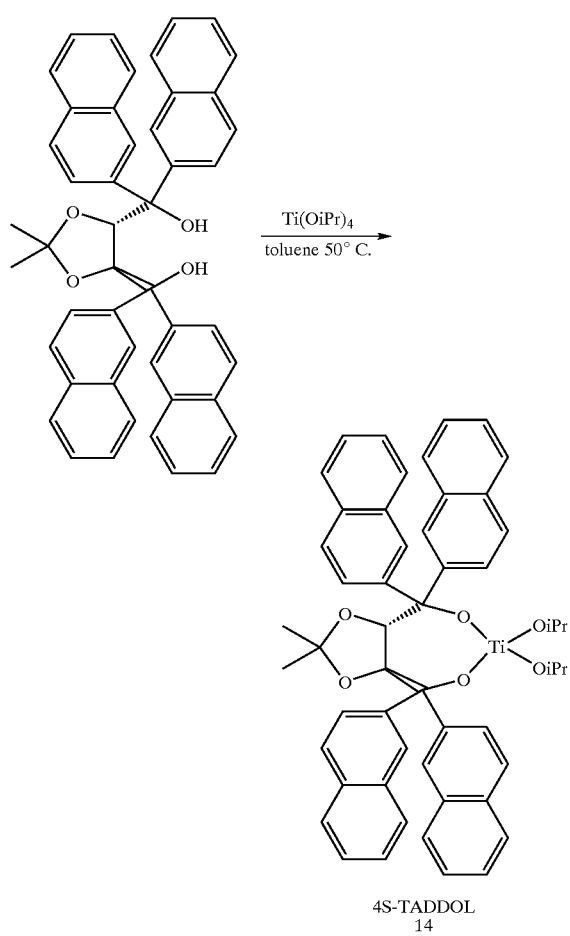

Ti(OiPr)4
toluene 50° C.

4S-TADDOL
14

A flame dried 200 mL round-bottom flask was purged with argon and then charged with 4S-diol (2.02 g; 3.0 mmol), toluene (30 mL; pre-dried with 4 Å molecular sieves) and titanium (IV) isopropoxide (0.90 mL; 3.0 mmol). The reaction mixture was heated to 50° C. and stirred for 5 h under an argon atmosphere. The toluene was removed in vacuo to give the catalyst as a pale yellow solid. The catalyst was kept under vacuum and then used immediately after purging with argon.

EXAMPLE 16

Synthesis of (R,R)-3-(1-Hydroxyethyl)-piperidine-1-carboxylic acid benzyl ester (16)

Protocol 1

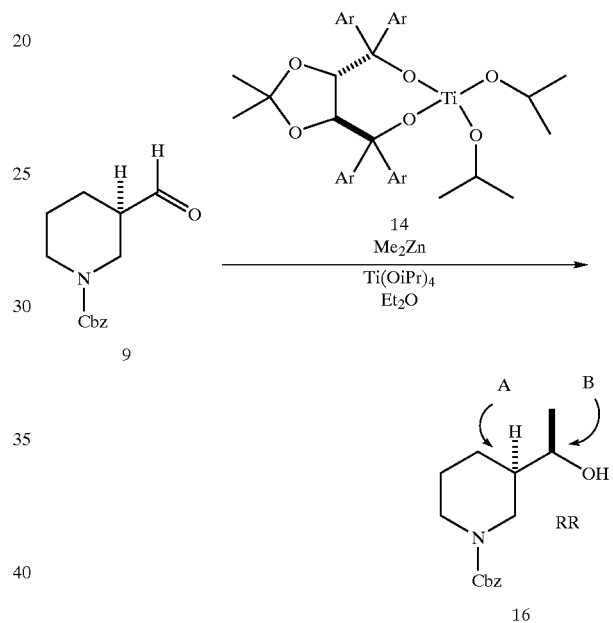

Using Schlenck glassware and air-free conditions, anhydrous ethyl ether freshly distilled from sodium/benzophenone (2.43 mL) was added to catalyst 14 prepared according to Example 15, protocol 1. Freshly distilled titanium tetraisopropoxide (0.430 mL, 1.46 mmol) was added, and the reaction was cooled to −78° C. Commercial Me$_2$Zn (1.21 mL, 2 M in toluene) was added, and the reaction was stirred at −78° C. for 1 hour. Aldehyde 9 (0.300 g, 1.21 mmol) in Et$_2$O (0.3 mL) was added, and the reaction was warmed to −30° C. and stirred overnight. The reaction was then quenched at −30° C. with saturated aqueous NH$_4$Cl. Et$_2$O was added, and the reaction was filtered through Celite wet with Et$_2$O. The reaction was dried with sodium sulfate, filtered, concentrated, and purified using an ISCO CombiFlash column (silica, 2:1 Hexane:EtOAc) to obtain 16 (0.167 g, 52%). HLPC analysis of the product is depicted in the Figures. $^1$H NMR (CDCl$_3$, 300 MHz) 7.42–7.30 (5H, broad s), 5.15 (2H, s), 4.08 (2H, broad d, J=12.8 Hz), 3.67 (1H, dq, J=6.2, 6.2 Hz), 2.81 (1H, td, J=12.4, 3.1 Hz), 3.90–2.60 (1H, broad), 2.40–1.90 (2H, broad), 1.80–1.68 (1H, m), 1.56–1.40 (2H, m), 1.23 (3H, d, J=6.3 Hz) ppm. $^{13}$C NMR (CDCl$_3$, 75 MHz) 155.58, 137.06, 128.61, 128.07, 127.91, 69.38, 67.14, 46.94, 44.81, 43.14, 25.71, 24.95, 21.03 ppm.

Protocol 2

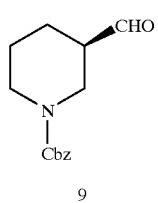 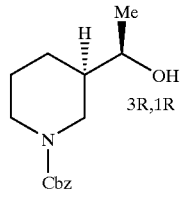

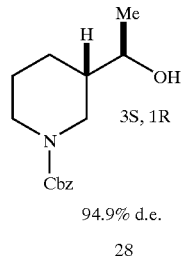

A 200 mL round-bottom flask containing 4S-TADDOL (14) (6.12 mmol) was charged with anhydrous ether (80 mL) and titanium isopropoxide (14.3 mL; 49 mmol). The solution was cooled to −78° C. and a 2.0 M solution of dimethyl zinc (40.5 mL; 81 mmol) was added. The solution was stirred at −78° C. for 1 h. To the solution was added aldehyde (10.6 g; 42.5 mmol) dissolved in ether (10 mL). The reaction mixture was warmed to −30° C. and stirred for 72 h. The reaction mixture was diluted with ether (500 mL) and quenched by the slow addition of saturated NH$_4$Cl (10 mL). The slurry was stirred at 20° C. for 10 min and then filtered through celite. The celite pad was washed with ether and the combined organic layers were concentrated in vacuo. The crude material was purified by flash chromatography (silica gel, hexanes/EtOAc 2:1 to 1:1) to give pure product (6.95 g, 62% yield). The diastereomeric purity was 90.1% de as determined by achiral HPLC analysis. The enantiomeric purity of the major diastereomer was >99.0% ee as determined by chiral HPLC analysis. $^1$H-NMR (300 MHz) δ (ppm) 7.38 (m; 5H); 5.17 (s; 2H); 4.06 (m; 2H); 3.65 (m; 1H); 2.81 (m; 1H); 2.76 (m; 1H); 1.98 (m; 2H); 1.75 (m; 1H); 1.48 (m; 2H); 1.30 (m; 1H); 1.21 (d; 3H). $^{13}$C-NMR (300 MHz) δ (ppm) 155.7; 137.1; 128.7; 128.2; 128.0; 69.2; 67.3; 47.1; 44.9; 43.3; 25.9; 25.2; 21.0.

EXAMPLE 17

Synthesis of (3S)-3-((1R)-1-Hydroxy-ethyl)-piperidine-1-carboxylic acid benzyl ester (28)

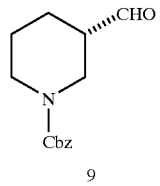

A 200 mL round-bottom flask containing 4S-TADDOL (14, 3.0 mmol) was charged with anhydrous ether (40 mL) and titanium isopropoxide (7.16 mL; 24.5 mmol). The solution was cooled to −78° C. and a 2.0 M solution of dimethyl zinc (20.2 mL; 40.5 mmol) was added. The solution was stirred at −78° C. for 1 h. To the solution was added aldehyde (5.0 g; 20.2 mmol) dissolved in ether (2.5 mL). The reaction mixture was warmed to −30° C. and stirred for 72 h. The reaction mixture was diluted with ether (250 mL) and quenched by the slow addition of saturated NH$_4$Cl (5 mL). The slurry was stirred at 20° C. for 10 min and then filtered through celite. The celite pad was washed with ether and the combined organic layers were concentrated in vacuo. The crude material was purified by flash chromatography (silica gel, hexanes/EtOAc 2:1 to 1:1) to give pure product (3.6 g, 67% yield). The diastereomeric purity was 94.9% de as determined by achiral HPLC analysis. The enantiomeric purity of the major diastereomer was >99.0% ee as determined by chiral HPLC analysis. $^1$H-NMR (300 MHz) δ (ppm) 7.38 (m; 5H); 5.14(s; 2H); 4.17 (m; 1H); 3.99 (m; 2H); 3.77 (m; 1H); 3.58 (m; 1H); 3.18 (m; 1H; 2.87 (m; 1H); 1.80 (m; 1H); 1.65 (m; 1H); 1.48 (m; 2H); 1.23 (d; 3H). $^{13}$C-NMR (300 MHz) δ (ppm) 155.9; 137.2; 128.7; 128.2; 128.0; 68.4; 67.3; 46.7; 45.1; 43.3; 27.2; 24.5; 21.1.

EXAMPLE 18

Figure 11:
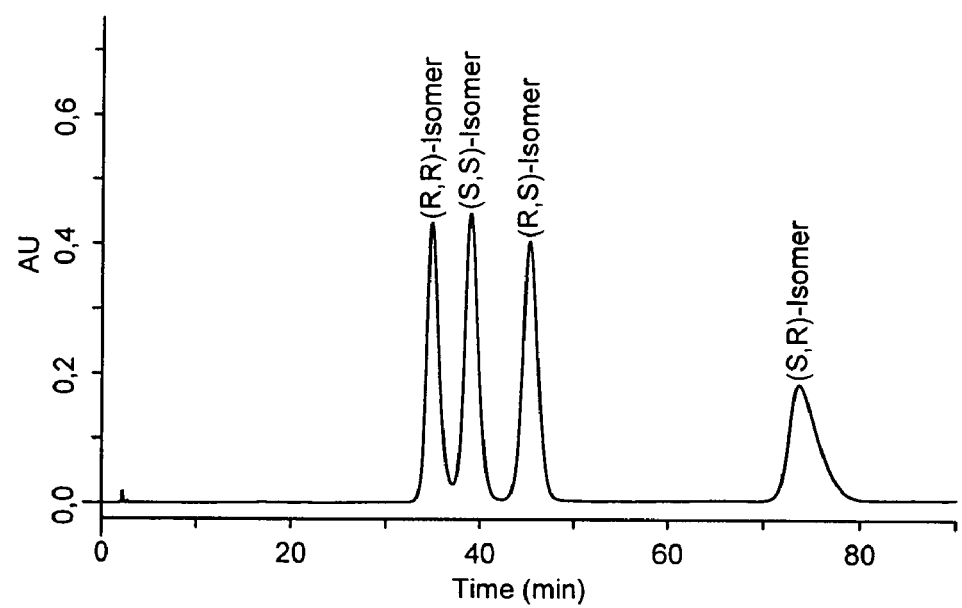
FIG. 11 depicts an HPLC chromatogram of a mixture of stereoisomers 15, 16, 27, and 28.
Figure 12:
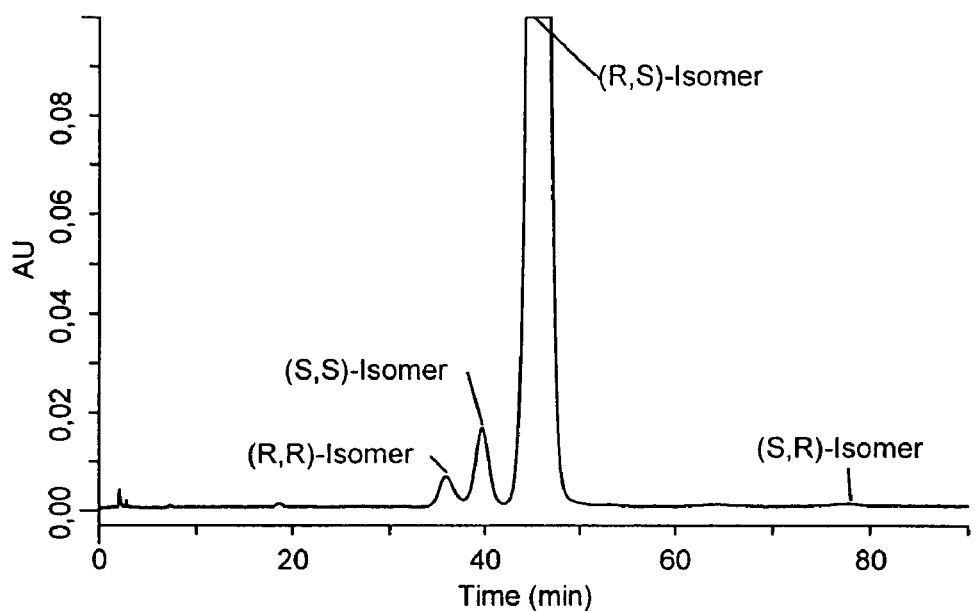
FIG. 12 depicts the HPLC chromatogram of purified stereoisomer 15 (R,S).
Figure 13:
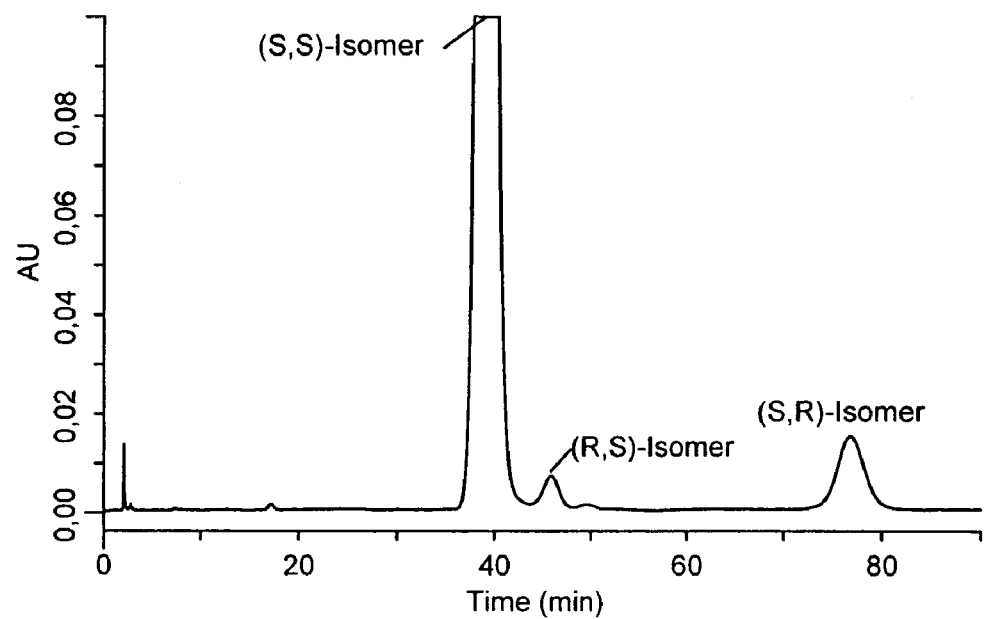
FIG. 13 depicts the HPLC chromatograms of purified stereoisomer 27 (S,S).
Figure 14:
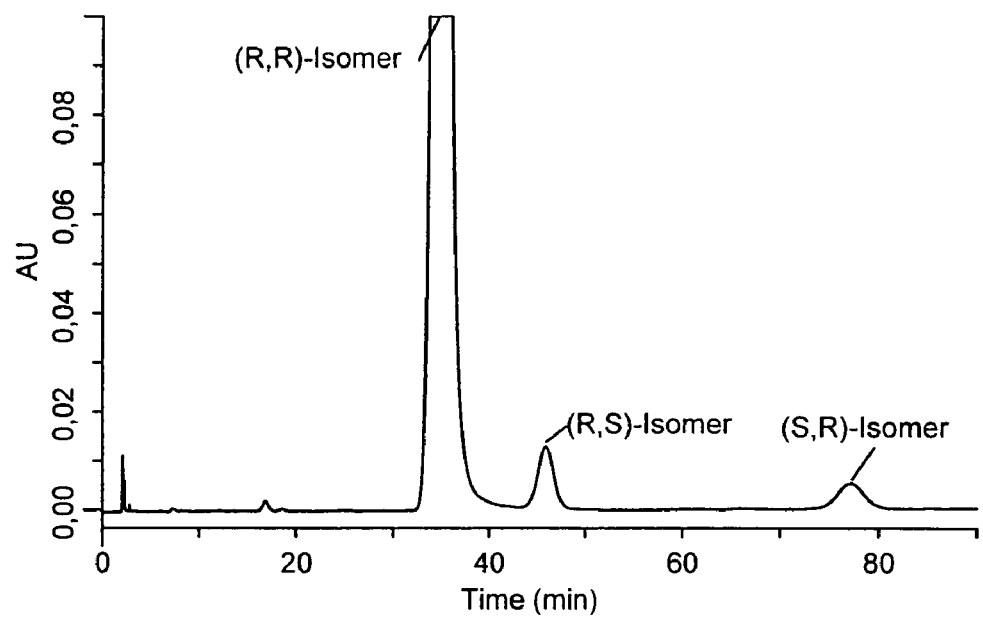
FIG. 14 depicts the HPLC chromatograms of purified stereoisomer 16 (R,R).
Figure 15:
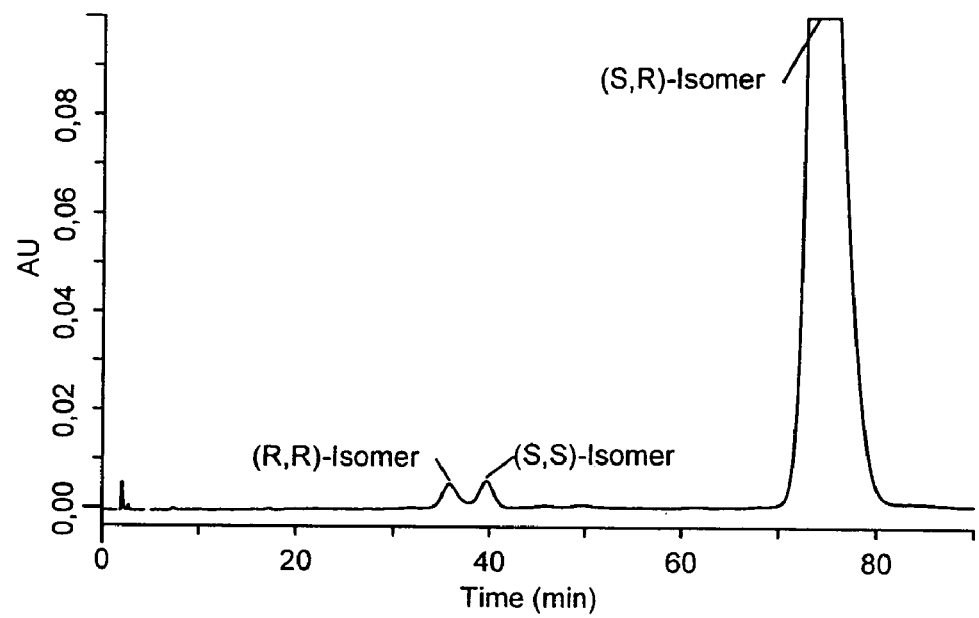
FIG. 15 depicts the HPLC chromatogram of purified stereoisomer 28 (S,R).

The chromatographic conditions used to separate the four isomers, 15, 16, 27 and 28, are described below. The chromatographic conditions generated the chromatographic separation depicted in FIG. 11.

Column: Chiralpak AD, 5 um, 4.6×250 mm
Mobile Phase: Hexane/IPA (97:3)
Flow Rate: 1.5 mL/min
Detection: UV 210 nm
Temperature: 5° C.

Identification of each peak was determined using authentic samples of each stereoisomer of 3-(1-hydroxyethyl) piperidine-1-carboxylic acid benzyl ester. This chiral HPLC method was subsequently used to analyze several samples of individual isomers. Representative chromatograms for each of the samples are presented in FIGS. 12–15.

Using peak area normalization to quantify the amount of individual isomers in each sample, the following data were obtained.

| Sample | % (R,R)-Isomer 16 | % (S,S)-Isomer 27 | % (R,S)-Isomer 15 | % (S,R)-Isomer 28 | % de major isomer | % ee major isomer |
|---|---|---|---|---|---|---|
| Example 12 (Protocol 2) | 1.23 | 3.02 | 95.65 | 0.11 | 91.3 | 99.8 |

| Sample | % (R,R)-Isomer 16 | % (S,S)-Isomer 27 | % (R,S)-Isomer 15 | % (S,R)-Isomer 28 | % de major isomer | % ee major isomer |
|---|---|---|---|---|---|---|
| Example 14 | <0.5%, ND | 94.61 | 1.13 | 4.26 | 89.2 | >98.9 |
| Example 16 (Protocol 2) | 96.17 | <0.5%, ND | 2.30 | 1.53 | 92.3 | >99.0 |
| Example 17 | 1.22 | 1.28 | <0.5%, ND | 97.50 | 95.0 | >99.0 |

ND = None Detected.

Since there was insufficient sample available to perform a spiked recovery study, the detection limit for the minor isomers in the presence of the major isomer was estimated at approximately 0.5%. In the case of Example 12, (R,S)-Isomer, there was a trace of the minor (S,R)-Isomer observed in the sample, and the integration determined it to be 0.11%.

EXAMPLE 19

Non-selective Synthesis of a Mixture of 15 and 16

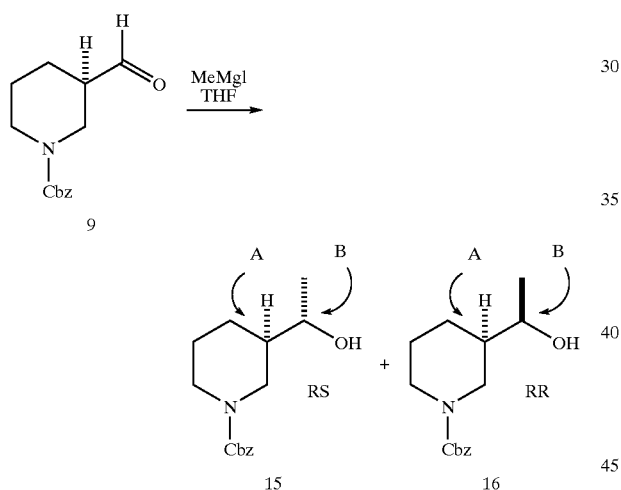

MeMgI (0.80 mL, 3.0M in Et$_2$O) was added dropwise to a stirring, −78° C. solution of aldehyde 9 (0.313 g, 1.20 mmol) in THF (6.0 mL). When the reaction was complete by TLC, the reaction was quenched with aqueous NH$_4$Cl, washed with H$_2$O, and extracted with EtOAc. The crude reaction mixture was dried with sodium sulfate and purified using an ISCO CombiFlash column (silica, 2:1 Hexane: EtOAc). HPLC analysis of the product is depicted in the Figures.

EXAMPLE 20

Testing Reaction Conditions for the Conversion of 9 to 15 Catalyzed by Catalyst 13

Using Schlenck glassware and air-free conditions, ethyl ether (2.12 mL) was added to catalyst 13. Catalyst 13 had been prepared either from toluene freshly distilled from sodium/benzophenone under argon, or it had been prepared from anhydrous toluene purchased from Aldrich and pre-dried for 24 hours with 4 Å molecular sieves that had been heated in a vacuum oven for 24 hours prior to their use. The amount of catalyst 13 was 5 mol %, 10 mol %, or 20 mol %. The ether solvent was either freshly distilled from sodium/benzophenone under argon, or was anhydrous ether purchased from Aldrich and pre-dried for 24 hours with 4 Å molecular sieves that had been heated in a vacuum oven for 24 hours prior to their use. Titanium tetraisopropoxide (0.347 mL, 1.27 mmol) was added, and the reaction was cooled to −78° C. Commercial Me$_2$Zn (1.06 mL, 2 M in toluene) was added, and the reaction was stirred at −78° C. for 1 hour. Aldehyde 9 (0.262 g, 1.06 mmol) in Et$_2$O (0.2 mL) was added, and the reaction was warmed to −30° C. and stirred overnight. The reaction was then quenched at −30° C. with saturated aqueous NH$_4$Cl. Et$_2$O was added, and the reaction was filtered through Celite wet with Et$_2$O. The reaction was dried with sodium sulfate, filtered, concentrated, and purified using an ISCO CombiFlash column (silica, 2:1 Hexane:EtOAc) to obtain 15. HLPC analysis of the results of these reactions is depicted in the Figures.

EXAMPLE 21

Synthesis of 3-(1-phenylaminoethyl)piperidine-1-carboxylic acid tert-butyl ester 22

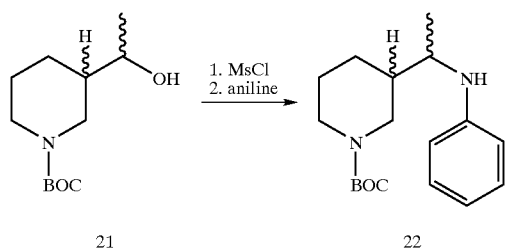

To a stirred suspension of 3-(1-hydroxyethyl)piperidine-1-carboxylic acid tert-butyl ester 21 (31 mg, 0.135 mmol) and piperidinomethyl polystyrene resin (60 mg) in 0.5 mL of CH$_2$Cl$_2$ was added methanesulfonyl chloride (15.7 µL, 1.5 eq.). The mixture was stirred at room temperature for 60 min. After removal of solvent, aniline (50 µL) was introduced. The mixture was heated at 95° C. overnight. The crude product was purified by a preparative thin layer chromatography (EtOAc/Hexane, 1:2) to afford 3-(1-phenylaminoethyl)piperidine-1-carboxylic acid tert-butyl ester 22 (21 mg, 51%).

EXAMPLE 22

Synthesis of (3R)-3-((1S)-1-Methanesulfonyloxy-ethyl)-piperidine-1-carboxylic acid benzyl ester (29)

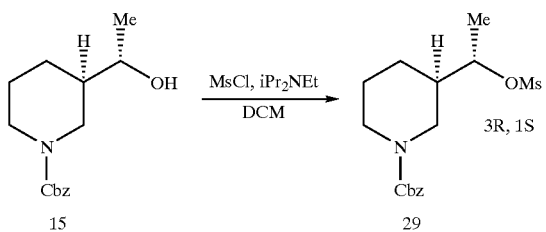

A 200 mL round-bottom flask was charged with alcohol (7.19 g; 27.3 mmol), DCM (100 mL) and diisopropylethylamine (5.23 mL; 30.0 mmol). The flask was cooled to 0° C. and methanesulfonyl chloride (2.32 mL; 30.0 mmol) was added dropwise. The reaction was warmed to 20° C. and stirred for 2 h. The reaction mixture was diluted with DCM (150 mL). The organic layer was washed with saturated NaHCO$_3$ (250 mL), saturated NaCl (250 mL), dried (Na$_2$SO$_4$), filtered and concentrated in vacuo. The crude material was purified by flash chromatography (silica gel, hexanes/EtOAc 4:1 to 2:1 with 2% 2.0 M NH$_3$ in EtOH) to give pure product (8.76 g, 94% yield). $^1$H-NMR (300 MHz) δ (ppm) 7.38 (m; 5H); 5.17 (s; 2H); 4.71 (m; 1H); 4.25 (m; 1H); 4.08 (m; 1H); 3.02 (m; 2H); 2;89 (bs: 3H); 2.76 (m; 1H); 1.85 (m; 1H); 1.78 (m; 2H); 1.48 (d; 3H); 1.21 (m; 1H). $^{13}$C-NMR (300 MHz) δ (ppm) 155.5; 137.0; 128.8; 128.2; 128.0; 81.0; 67.3; 45.8; 44.6; 41.4; 38.8; 27.0; 24.8; 19.2.

EXAMPLE 23

Synthesis of (3R)-3-((1R)-1-Methanesulfonyloxy-ethyl)-piperidine-1-carboxylic acid benzyl ester (30)

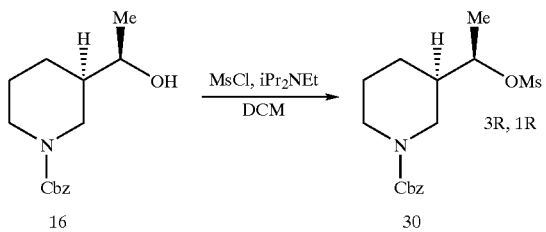

A 200 mL round-bottom flask was charged with alcohol (3.15 g; 12.0 mmol), DCM (100 mL) and diisopropylethylamine (2.29 mL; 13.2 mmol). The flask was cooled to 0° C. and methanesulfonyl chloride (1.02 mL; 13.2 mmol) was added dropwise. The reaction was warmed to 20° C. and stirred for 2 h. The reaction mixture was diluted with DCM (150 mL). The organic layer was washed with saturated NaHCO$_3$ (250 mL), saturated NaCl (250 mL), dried (Na$_2$SO$_4$), filtered and concentrated in vacuo. The crude material was purified by flash chromatography (silica gel, hexanes/EtOAc 4:1 to 2:1 with 2% 2.0 M NH$_3$ in EtOH) to give pure product (3.92 g, 96% yield). $^1$H-NMR (300 MHz) δ (ppm) 7.40 (m; 5H); 5.19 (s; 2H); 4.75 (m; 1H); 4.16 (m; 2H); 3.02 (bs; 3H); 2.82 (m: 2H); 1.99 (m; 1H); 1.78 (m; 2H); 1.42 (d; 3H); 1.39 (m; 2H). $^{13}$C-NMR (300 MHz) δ (ppm) 155.4; 137.0; 128.8; 128.3; 128.0; 80.8; 67.3; 46.2; 44.7; 41.4; 39.0; 26.0; 24.7; 18.9.

EXAMPLE 24

Synthesis of (3S)-3-((1S)-1-Methanesulfonyloxy-ethyl)-piperidine-1-carboxylic acid benzyl ester (31)

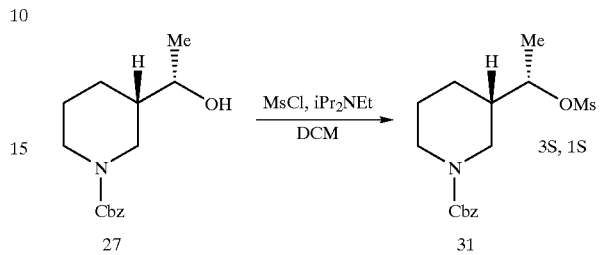

A 200 mL round-bottom flask was charged with alcohol (0.5 g; 1.9 mmol), DCM (10 mL) and diisopropylethylamine (0.4 mL; 2.09 mmol). The flask was cooled to 0° C. and methanesulfonyl chloride (0.16 mL; 2.09 mmol) was added dropwise. The reaction was warmed to 20° C. and stirred for 2 h. The reaction mixture was diluted with DCM (15 mL). The organic layer was washed with saturated NaHCO$_3$ (25 mL), saturated NaCl (25 mL), dried (Na$_2$SO$_4$), filtered and concentrated in vacuo. The crude material was purified by flash chromatography (silica gel, hexanes/EtOAc 4:1 to 2:1 with 2% 2.0 M NH$_3$ in EtOH) to give pure product (616 g, 95% yield). $^1$H-NMR (300 MHz) δ (ppm) 7.40 (m; 5H); 5.19 (s; 2H); 4.75 (m; 1H); 4.16 (m; 2H); 3.02 (bs; 3H); 2.82 (m: 2H); 1.99 (m; 1H); 1.78 (m; 2H); 1.42 (d; 3H); 1.39 (m; 2H). $^{13}$C-NMR (300 MHz) δ (ppm) 155.3; 137.1; 128.7; 128.2; 128.0; 80.7; 67.2; 46.2; 44.7; 41.4; 38.8; 25.9; 24.6; 18.8.

EXAMPLE 25

Synthesis of (3S)-3-((1R)-1-Methanesulfonyloxy-ethyl)-piperidine-1-carboxylic acid benzyl ester (32)

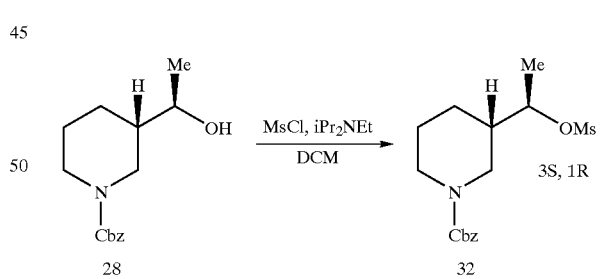

A 200 mL round-bottom flask was charged with alcohol (0.5 g; 1.9 mmol), DCM (10 mL) and diisopropylethylamine (0.4 mL; 2.09 mmol). The flask was cooled to 0° C. and methanesulfonyl chloride (0.16 mL; 2.09 mmol) was added dropwise. The reaction was warmed to 20° C. and stirred for 2 h. The reaction mixture was diluted with DCM (15 mL). The organic layer was washed with saturated NaHCO$_3$ (25 mL), saturated NaCl (25 mL), dried (Na$_2$SO$_4$), filtered and concentrated in vacuo. The crude material was purified by flash chromatography (silica gel, hexanes/EtOAc 4:1 to 2:1 with 2% 2.0 M NH$_3$ in EtOH) to give pure product (0.596 g, 92% yield). $^1$H-NMR (300 MHz) δ (ppm) 7.38 (m; 5H);

5.17 (s; 2H); 4.71 (m; 1H); 4.25 (m; 1H); 4.08 (m; 1H); 3.02 (m; 2H); 2;89 (bs: 3H); 2.76 (m; 1H); 1.85 (m; 1H); 1.78 (m; 2H); 1.48 (d; 3H); 1.21 (m; 1H). $^{13}$C-NMR (300 MHz) δ (ppm) 155.5; 137.0; 128.8; 128.2; 128.0; 81.0; 67.3; 45.8; 44.6; 41.4; 38.8; 27.0; 24.8; 19.2.

EXAMPLE 26

Synthesis of (3R)-3-((1R)-1-Phenylamino-ethyl)-piperidine-1-carboxylic acid benzyl ester (17)

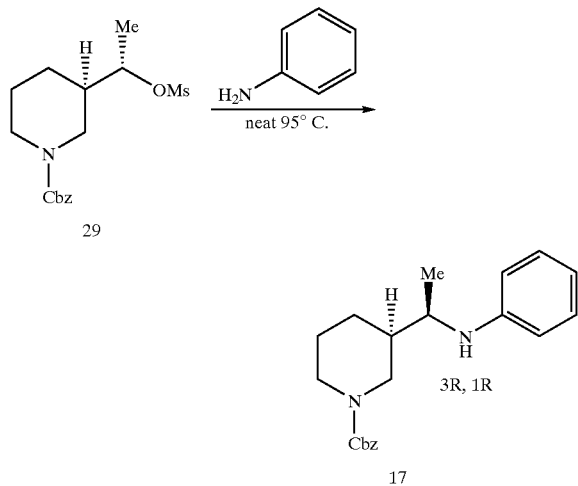

A 100 mL par-shaker flask was charged with mesylate (6.95 g, 20.4 mmol) and aniline (55 mL; 611 mmol). The reaction mixture was sealed and heated to 95° C. for 48 h. The excess aniline was removed by vacuum distillation and the crude material was purified by flash chromatography (silica gel, hexanes/EtOAc 19:1 to 4:1 with 2% 2.0 M NH$_3$ in EtOH) to give product (7.52 g, >100% yield). The crude product was contaminated by aniline that could not be completely removed by additional column chromatography. The diastereomeric purity was 90.6% de as determined by HPLC analysis. $^1$H-NMR (300 MHz) δ (ppm) 7.38 (m; 5H); 7.20 (t; 2H); 6.77 (t; 1H); 6.61 (d; 2H); 5.17 (s; 2H): 4.15 (m; 2H); 3.40 (m; 2H); 2.85 (m; 2H); 2.00 (m; 1H); 1.88 (m; 1H); 1.63 (m; 1H); 1.50 (m; 1H); 1.30 (m; 1H); 1.21 (d; 3H). $^{13}$C-NMR (300 MHz) δ (ppm) 155.7; 148.0; 137.3; 129.7; 128.8; 128.3; 128.1; 117.3; 113.4; 67.3; 51.1; 47.4; 45.0; 42.1; 27.5; 25.4; 18.5.

EXAMPLE 27

Synthesis of (3R)-3-((1S)-1-Phenylamino-ethyl)-piperidine-1-carboxylic acid benzyl ester (19)

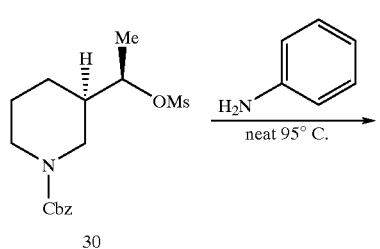

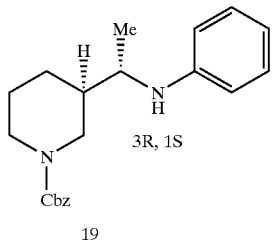

A 100 mL par-shaker flask was charged with mesylate (3.92 g, 11.5 mmol) and aniline (31 mL; 344 mmol). The reaction mixture was sealed and heated to 95° C. for 48 h. The excess aniline was removed by vacuum distillation and the crude material was purified by flash chromatography (silica gel, hexanes/EtOAc 19:1 to 4:1 with 2% 2.0 M NH$_3$ in EtOH) to give product (4.09 g, >100% crude yield). The crude product was contaminated by aniline that could not be completely removed by additional column chromatography. $^1$H-NMR (300 MHz) δ (ppm) 7.38 (m; 5H); 7.20 (t; 2H); 6.77 (t; 2H); 6.61 (d; 1H); 5.17 (s; 2H): 4.40 (m; 1H); 4.18 (m; 1H); 3.39 (m; 1H); 2.80 (m; 2H); 2.58 (m; 1H); 1.92 (m; 1H); 1.78 (m; 1H); 1.53 (m; 2H); 1.28 (m; 1H); 1.19 (d; 3H). $^{13}$C-NMR (300 MHz) δ (ppm) 155.7; 148.0; 137.4; 129.8; 128.9; 128.3; 128.2; 117.4; 113.6; 67.4; 51.2; 48.1; 45.1; 42.1; 27.5; 25.8; 18.3.

EXAMPLE 28

Synthesis of (3S)-3-((1R)-1-Phenylamino-ethyl)-piperidine-1-carboxylic acid benzyl ester (33)

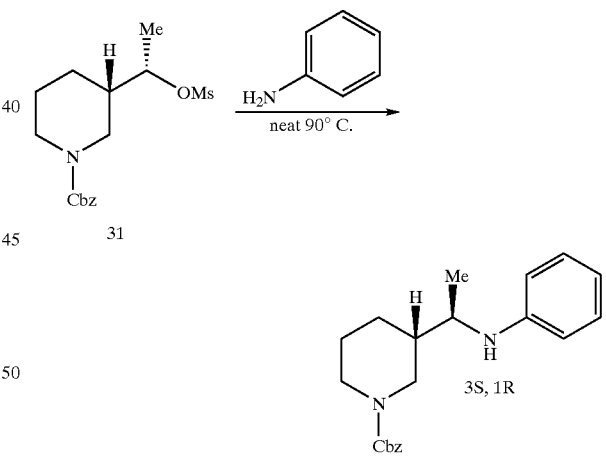

A 100 mL par-shaker flask was charged with mesylate (0.3 g, 0.88 mmol) and aniline (5 mL; 55.5 mmol). The reaction mixture was sealed and heated to 90° C. for 48 h. The excess aniline was removed by vacuum distillation and the crude material was purified by flash chromatography (silica gel, hexanes/EtOAc 19:1 to 4:1 with 2% 2.0 M NH$_3$ in EtOH) to give product (0.272 g, 91% yield). The diastereomeric purity was 84.36% de as determined by HPLC analysis. $^1$H-NMR (300 MHz) δ (ppm) 7.37 (m; 5H); 7.20 (t; 2H); 6.70 (t; 2H); 6.61 (d; 1H); 5.15 (s; 2H): 4.40 (m; 1H); 4.15 (m; 1h); 3.40 (m; 1H); 2.78 (m; 2H); 2.52 (m; 1H);

1.92 (m; 1H); 1.78 (m; 1H); 1.53 (m; 2H); 1.28 (m; 1H); 1.19 (d; 3H). $^{13}$C-NMR (300 MHz) δ (ppm) 155.6; 147.8; 137.3; 129.6; 128.9; 128.2; 128.1; 117.4; 113.5; 67.3; 51.0; 48.0; 45.0; 42.1; 27.4; 25.6; 18.2.

The lower % de observed for this reaction reflects the % de of the starting alcohol (27), and not of a lack of stereochemical integrity for this reaction. Alcohol 27 was synthesized from aldehyde 12 that had been stored at room temperature. Storage of the aldehyde at room temperature results in reduced enantiopurity.

EXAMPLE 29

Synthesis of (3S)-3-((1S)-1-Phenylamino-ethyl)-piperidine-1-carboxylic acid benzyl ester (34)

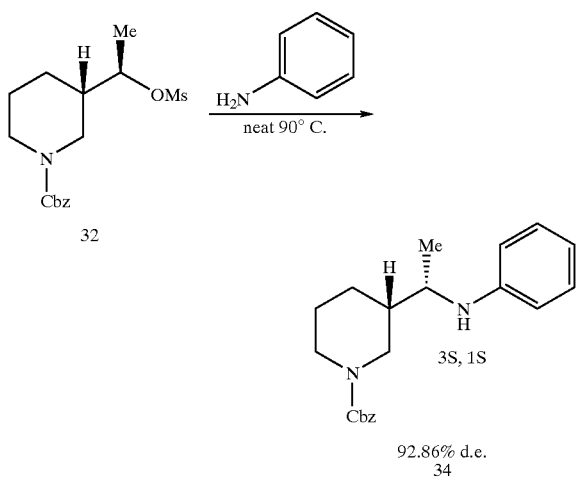

A 100 mL par-shaker flask was charged with mesylate (0.45 g, 1.32 mmol) and aniline (7.5 mL; 83.25 mmol). The reaction mixture was sealed and heated to 90° C. for 48 h. The excess aniline was removed by vacuum distillation and the crude material was purified by flash chromatography (silica gel, hexanes/EtOAc 19:1 to 4:1 with 2% 2.0 M NH$_3$ in EtOH) to give product (0.381 g, 85% yield). The diastereomeric purity was 92.86% de as determined by HPLC analysis. $^1$H-NMR (300 MHz) δ (ppm) 7.38 (m; 5H); 7.20 (t; 2H); 6.77 (t; 1H); 6.61 (d; 2H); 5.17 (s; 2H): 4.15 (m; 2H); 3.40 (m; 2H); 2.85 (m; 2H); 2.00 (m; 1H); 1.88 (m; 1H); 1.63 (m; 1H); 1.50 (m; 1H); 1.30 (m; 1H); 1.21 (d; 3H). $^{13}$C-NMR (300 MHz) δ (ppm) 155.7; 148.0; 137.3; 129.7; 128.8; 128.3; 128.1; 117.3; 113.4; 67.3; 51.1; 47.4; 45.0; 42.1; 27.5; 25.4; 18.5.

EXAMPLE 30

Synthesis of (3R)-3-((1R)-1-Phenylamino-ethyl)-piperidine-1-carboxylic acid benzyl ester (17)

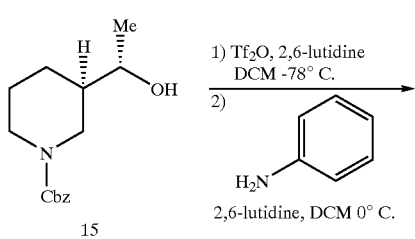

-continued

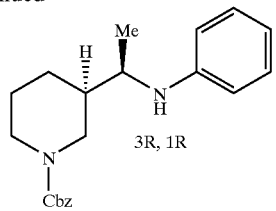

A 50 mL round-bottom flask was charged with alcohol (1.0 g, 3.80 mmol), DCM (5 mL) and 2,6-lutidine (487 μL; 4.20 mol). The reaction mixture was cooled to −78° C. and Tf$_2$O (703 μL ; 4.18 mmol) was added dropwise. The reaction mixture was stirred at −78° C. for 1 h. To the reaction mixture was added aniline (519 mL; 5.70 μmol) and 2,6-lutidine (663 μL; 5.70 mmol). The reaction mixture was warmed to 0° C. and stirred for 2 h. The reaction mixture was diluted with DCM (50 mL), washed with saturated NaHCO$_3$ (50 mL), saturated NaCl (50 mL), dried (Na$_2$SO$_4$), filtered and concentrated in vacuo. The crude material was purified by flash chromatography (silica gel, hexanes/EtOAc 19:1 to 4:1 with 2% 2.0 M NH$_3$ in EtOH) to give product (720 mg, 56% yield). $^1$H-NMR (300 MHz) δ (ppm) 7.38 (m; 5H); 7.20 (t; 2H); 6.77 (t; 1H); 6.61 (d; 2H); 5.17 (s; 2H): 4.15 (m; 2H); 3.40 (m; 2H); 2.85 (m; 2H); 2.00 (m; 1H); 1.88 (m; 1H); 1.63 (m; 1H); 1.50 (m; 1H); 1.30 (m; 1H); 1.21 (d; 3H). $^{13}$C-NMR (300 MHz) δ (ppm) 155.7; 148.0; 137.3; 129.7; 128.8; 128.3; 128.1; 117.3; 113.4; 67.3; 51.1; 47.4; 45.0; 42.1; 27.5; 25.4; 18.5.

EXAMPLE 31

Synthesis of N-[1-(1-phenethylpiperidin-3-yl)ethyl]-N-Phenylpropionamide 23

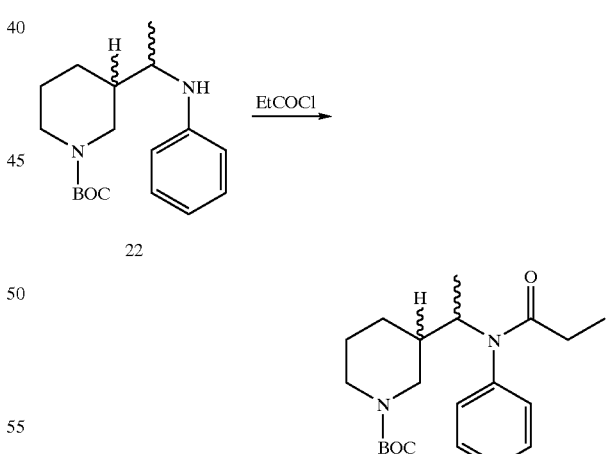

To a solution of afford 3-(1-phenylaminoethyl)piperidine-1-carboxylic acid tert-butyl ester 22 and N,N-diisopropylethylamine (5 equiv) in CH$_2$Cl$_2$ (0.5 M) at 0° C. was added propionyl chloride (3.0 equiv). The reaction mixture was shaken overnight. The mixture was poured into 10% NaOH, then extracted with EtOAc. The extracts were combined and washed with aqueous NaHCO$_3$, dried over sodium sulfate, filtered, and concentrated. The crude material was purified by column chromatography (silica gel, hexane:EtOAc, 4:1) to give N-[1-(1-phenethylpiperidin-3-yl)ethyl]-N-Phenyl-propionamide 23.

EXAMPLE 32

Synthesis of (3R)-3-[(1R)-1-(Phenyl-propionyl-amino)-ethyl]-piperidine-1-carboxylic acid benzyl ester (18)

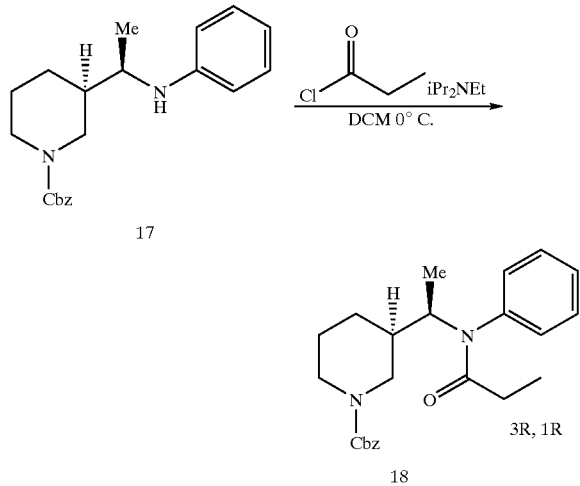

A 100 mL round-bottom flask was charged with amine (obtained by $S_N2$ displacement of the corresponding triflate) (5.45 g; 16.1 mmol), DCM (20 mL) and diisopropylethylamine (5.61 mL: 32.2 mmol). The reaction mixture was cooled to 0° C. and propionyl chloride (2.80 mL; 32.2 mmol) was added. The reaction mixture was stirred at 20° C. for 16 h. The reaction mixture was diluted with EtOAc (1.00 mL). The organic layer was washed with saturated NaHCO₃ (100 mL), saturated NaCl (100 mL), dried (Na₂SO₄), filtered and concentrated in vacuo. The crude material was purified by flash chromatography (silica gel, hexanes/EtOAc 4:1 to 2:1) to give product (5.72 g, 90% yield). ¹H-NMR (300 MHz) δ (ppm) 7.40 (m; 7H); 7.10 (d; 3H); 5.08 (s; 2H); 4.78 (m; 1H); 4.00 (m; 2H); 2.93 (m; 1H); 2.76 (t; 1H); 2.05 (m; 1H); 1.98 (q; 2H); 1.80 (m; 2H); 1.50 (m; 4H); 1.02 (m; 5H). ¹³C-NMR (300 MHz) δ (ppm) 174.2; 155.4; 139.0; 137.1; 131.0; 129.7; 128.7; 128.5; 128.1; 128.0; 67.2; 52.8; 47.5; 44.7; 39.6; 28.8; 28.7; 24.9; 17.3; 10.0.

EXAMPLE 33

Synthesis of (3R)-3-[(1S)-1-(Phenyl-propionyl-amino)-ethyl]-piperidine-1-carboxylic acid benzyl ester (20)

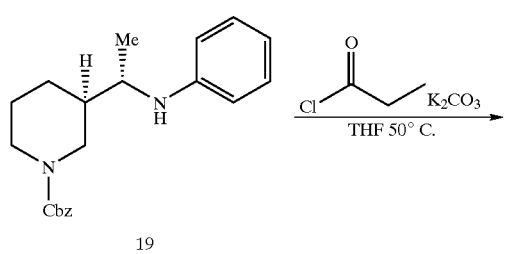

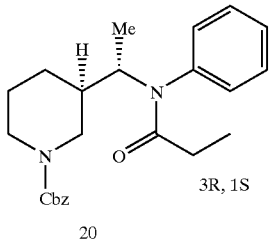

A 100 mL round-bottom flask was charged with amine (obtained by $S_N2$ displacement of the corresponding mesylate) (1.37 g; 4.05 mmol), THF (25 mL), potassium bicarbonate (2.79 g mL: 20.0 mmol) and propionyl chloride (1.76 mL; 20.0 mmol). The reaction mixture was heated to 50° C. and stirred for 16 h. The reaction mixture was cooled to room temperature and diluted with EtOAc (100 mL). The organic layer was washed with saturated NaHCO₃ (100 mL), saturated NaCl (100 mL), dried (Na₂SO₄), filtered and concentrated in vacuo. The crude material was purified by flash chromatography (silica gel, hexanes/EtOAc 4:1 to 2:1) to give product (2.28 g, 50% yield). ¹H-NMR (300 MHz) δ (ppm) 7.48 (d; 1H); 7.40 (m; 6H); 7.10 (d; 3H); 5.18 (s; 2H); 4.78 (m; 1H); 4.44 (m; 1H); 4.22 (m; 1H); 2.78 (m; 2H); 1.98 (m; 2H); 1.80 (m; 4H); 1.40 (m; 2H); 1.02 (m; 5H). ¹³C-NMR (300 MHz) δ (ppm) 174.5; 155.0; 138.8; 137.1; 129.5; 129.0; 128.8; 128.5; 124.0; 120.1; 67.6; 52.2; 48.6; 44.7; 40.5; 30.8; 28.5; 25.5; 17.1; 10.0.

EXAMPLE 34

Synthesis of (3S)-3-[(1R)-1-(Phenyl-propionyl-amino)-ethyl]-piperidine-1-carboxylic acid benzyl ester (35)

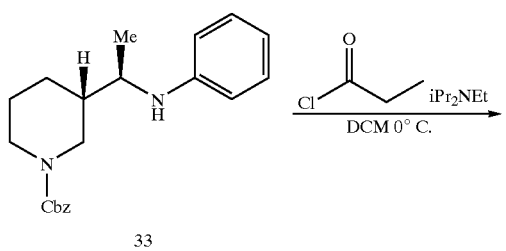

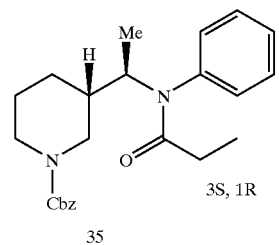

A 100 mL round-bottom flask was charged with amine (obtained by $S_N2$ displacement of the corresponding mesylate) (250 g; 0.73 mmol), DCM (5 mL) and diisopropyl-ethylamine (0.65 mL: 3.65 mmol). The reaction mixture was cooled to 0° C. and propionyl chloride (0.20 mL; 2.28 mmol) was added. The reaction mixture was stirred at 0° C. for 4 h. The reaction mixture was diluted with EtOAc (5 mL). The organic layer was washed with saturated NaHCO₃ (10 mL), saturated NaCl (10 mL), dried (Na₂SO₄), filtered and concentrated in vacuo. The crude material was purified by flash chromatography (silica gel, hexanes/EtOAc 4:1 to 2:1) to give product (0.165 g, 57% yield). ¹H-NMR (300 MHz) δ (ppm) 7.48 (d; 1H); 7.40 (m; 6H); 7.10 (d; 3H); 5.18 (s; 2H); 4.78 (m; 1H); 4.44 (m; 1H); 4.22 (m; 1H); 2.78 (m; 2H); 1.98 (m; 2H); 1.80 (m; 4H); 1.40 (m; 2H); 1.02 (m; 5H). ¹³C-NMR (300 MHz) δ (ppm) 174.5; 155.0; 138.8; 137.1; 129.5; 129.0; 128.8; 128.5; 124.0; 120.1; 67.6; 52.2; 48.6; 44.7; 40.5; 30.8; 28.5; 25.5; 17.1; 10.0.

EXAMPLE 35

Synthesis of (3S)-3-[(1S)-1-(Phenyl-propionyl-amino)-ethyl]-piperidine-1-carboxylic acid benzyl ester (36)

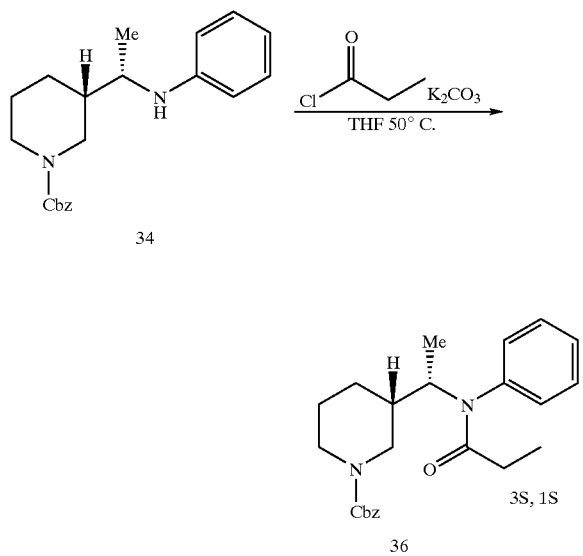

A 100 mL round-bottom flask was charged with amine (obtained by S$_N$2 displacement of the corresponding mesylate) (0.300 g; 0.88 mmol), DCM (6 mL), and diisopropylethylamine (0.78 mL: 4.38 mmol). The reaction mixture was cooled to 0° C. and propionyl chloride (0.24 mL; 2.74 mmol) was added. The reaction mixture was stirred at 0° C. for 4 h. The reaction mixture was diluted with EtOAc (6 mL). The organic layer was washed with saturated NaHCO₃ (10 mL), saturated NaCl (10 mL), dried (Na₂SO₄), filtered and concentrated in vacuo. The crude material was purified by flash chromatography (silica gel, hexanes/EtOAc 4:1 to 2:1) to give product (0.236 g, 68% yield). ¹H-NMR (300 MHz) δ (ppm) 7.40 (m; 7H); 7.10 (d; 3H); 5.08 (s; 2H); 4.78 (m; 1H); 4.00 (m; 2H); 2.93 (m; 1H); 2.76 (m; 1H); 1.98 (q; 2H); 1.80 (m; 2H); 1.50 (m; 4H); 1.02 (m; 5H). ¹³C-NMR (300 MHz) δ (ppm) 174.2; 155.4; 139.0; 137.1; 131.0; 129.7; 128.7; 128.5; 128.1; 128.0; 67.2; 53.8; 52.8; 47.5; 44.7; 39.6; 28.8; 28.7; 24.9; 17.3; 10.0.

EXAMPLE 36

Synthesis of N-[1-(1-phenethylpiperidine-3-yl)ethyl]-N-Phenylpropionamide 24

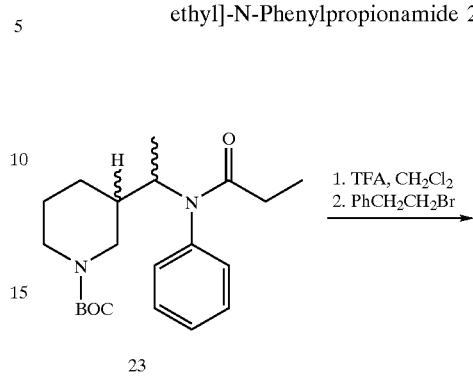

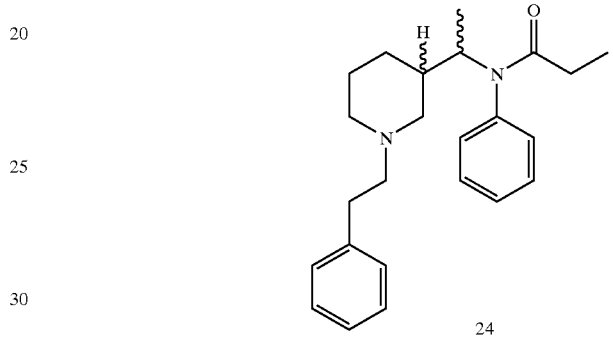

To a solution of N-[1-(1-phenethylpiperidin-3-yl)ethyl]-N-Phenylpropionamide 23 in CH₂Cl₂ (0.45 M) at 0° C. was added TFA. After stirring for 30 min., the solvent and excess TFA was removed by evaporation. The residue was dissolved in 1.5 mL of CH₃CN, to which K₂CO₃ and (2-bromoethyl)benzene (2 equiv) were added. The mixture was stirred at 50° C. overnight. After cooling down to room temperature, 10% NaOH was added. The organic layer was separated, and the aqueous layer was extracted with EtOAc. The combined organic layers were washed with brine and dried with sodium sulfate, filtered, and concentrated. The crude product was purified by flash silica gel chromatography (5% MeOH in CH₂Cl₂) to provide N-[1-(1-phenethylpiperidine-3-yl)ethyl]-N-Phenylpropionamide 24.

EXAMPLE 37

Synthesis of (3R)-3-[(1R)-1-(Phenyl-propionyl-amino)-ethyl]-piperidine (37)

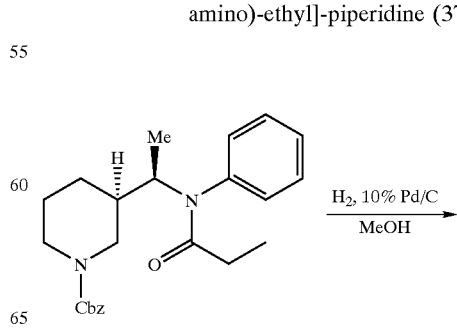

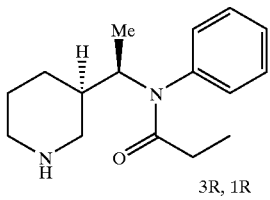

37

A 100 mL Parr shaker-flask was charged with Cbz-protected amine (1.01 g; 2.53 mmol) and MeOH (10 mL). The flask was purged with argon and 10% (w/w) Pd/C was added (270 mg; 0.25 mmol). The reaction mixture was fitted with a hydrogen balloon and hydrogenated at 20° C. for 16 h. The reaction mixture was filtered through celite and the celite pad washed with MeOH. The combined organics were concentrated in vacuo to give product (660 mg, 99% yield). ¹H-NMR (300 MHz) δ (ppm) 7.41 (m; 3H); 7.10 (d; 2H); 4.75 (m; 1H); 3.25 (dd; 2H); 2.68 (dt; 1H); 2.51 (t; 1H); 2.16 (dd; 1H); 1.95 (m; 4H); 1.80 (m; 2H); 1.40 (m; 1H); 1.02 (m; 5H). ¹³C-NMR (300 MHz) δ (ppm) 174.4; 139.3; 129.8; 129.5; 128.7; 53.2; 47.6; 44.8; 38.5; 28.7; 27.8; 23.2; 17.0; 9.9.

EXAMPLE 38

Synthesis of (3R)-3-[(1S)-1-(Phenyl-propionyl-amino)-ethyl]-piperidine (38)

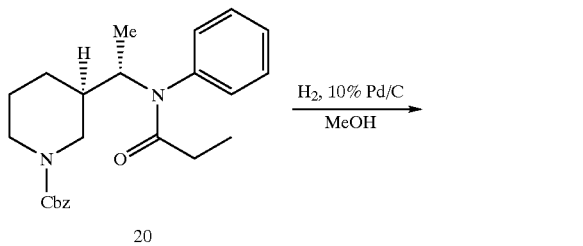

20

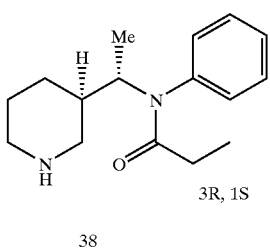

38

A 100 mL Parr shaker-flask was charged with Cbz-protected amine (2.28 g; 5.70 mmol) and MeOH (10 mL). The flask was purged with argon and 10% (w/w) Pd/C was added (604 mg; 0.57 mmol). The reaction mixture was fitted with a hydrogen balloon and hydrogenated at 20° C. for 16 h. The reaction mixture was filtered through celite and the celite pad washed with MeOH. The combined organics were concentrated in vacuo to give product (1.45 g, 98% yield). ¹H-NMR (300 MHz) δ (ppm) 7.41 (m; 3H); 7.10 (d; 2H); 4.78 (m; 1H); 3.50 (d; 1H); 3.23 (d; 1H); 2.79 (t; 2H); 2.00 (m; 3H); 1.80 (m; 4H); 1.23 (m; 1H); 1.02 (m; 5H). ¹³C-NMR (300 MHz) δ (ppm) 174.6; 138.7; 130.2; 129.3; 128.76; 52.4; 48.7; 45.2; 38.6; 28.6; 27.2; 23.5; 16.9; 9.9.

EXAMPLE 39

Synthesis of N-[(1R)-1-((3S)-1-Phenethyl-piperidin-3-yl)-ethyl]-N-phenyl-propionamide (2)

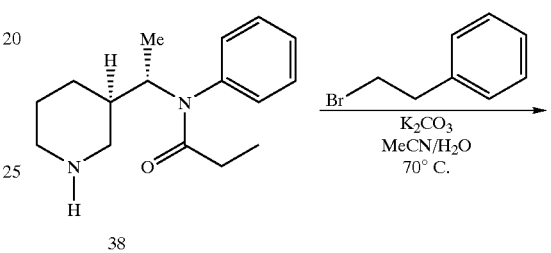

38

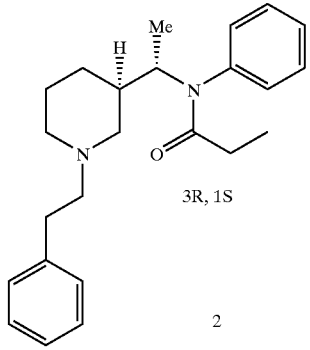

2

A 25 mL round-bottom flask was charged with amine (133 mg; 0.51 mmol), K₂CO₃ (218 mg; 1.5 mmol), MeCN (1 mL), H₂O (1 mL) and phenethyl bromide (84 μL; 0.61 mmol). The reaction mixture was heated to 70° C. and stirred for 3 h. The reaction mixture was cooled to room temperature and diluted with DCM (50 mL). The organic layer was washed with water (50 mL), saturated NaCl (50 mL), dried (Na₂SO₄), filtered and concentrated in vacuo. The crude material was purified chromatography (silica gel, hexanes/EtOAc 4:1 with 2% 2.0 M NH₃ in EtOH) to give pure product (72 mg, 40% yield). ¹H-NMR (300 MHz) δ (ppm) 7.42 (m; 5H); 7.21 (t; 2H); 6.78 (t; 1H); 6.60 (d; 2H); 5.17 (m, 2H); 4.40 (m; 1H); 4.19 (m; 1H); 3.49 (m; 2H); 3.40 (m; 2H); 2.82 (m; 2H); 2.59 (m; 2H); 1.98 (m; 1H); 1.78 (m; 1H); 1.57 (m; 2H); 1.22 (m; 2H); 1.18 (d; 3H) 1.05 (m; 1H). ¹³C-NMR (300 MHz) δ (ppm) 174.3; 140.7; 139.2; 131.1; 129.8; 129.0; 128.6; 126.3; 120.1; 61.2; 58.0; 54.6; 52.8; 40.4; 34.0; 28.8; 28.3; 25.7; 17.4; 10.3.

EXAMPLE 40

Chiral Chromatographic Purification of Stereoisomers of N-[1-(1-phenethyl-piperidin-3-yl)-ethyl]-N-phenyl-propionamide (24)

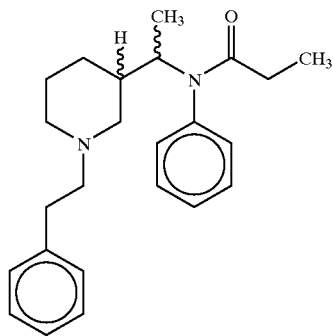

Figure 40:
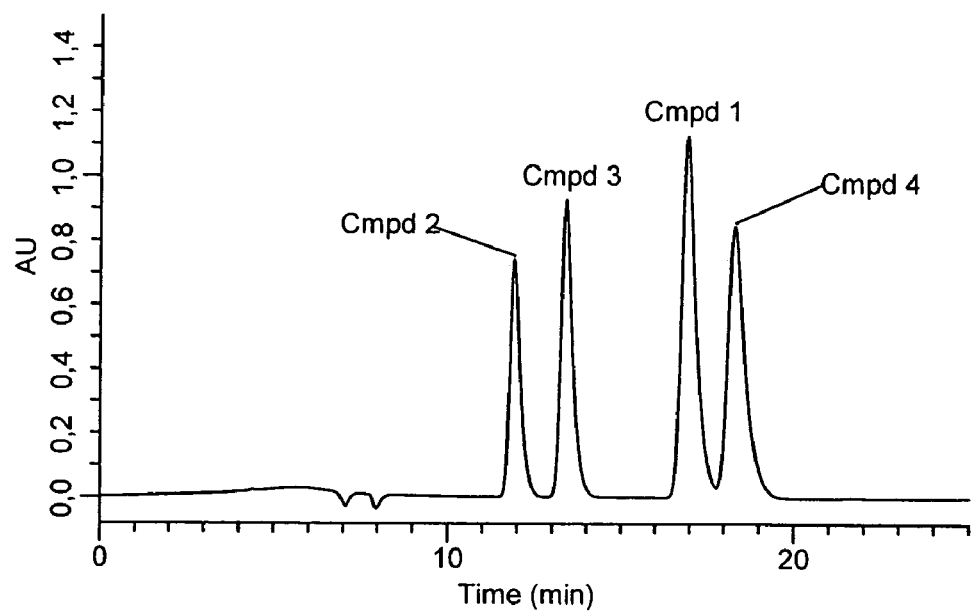
FIG. 40 depicts an HPLC chromatogram of a mixture of stereoisomers 1, 2, 3, and 4.

The chromatographic conditions to separate the four (1, 2, 3, and 4) possible stereoisomers of compound 24 are described below. The chromatographic conditions generated the chromatographic separation depicted in FIG. 40.

| Column: | Chiralcel OD, 10 um, 4.6 × 250 mm |
|---|---|
| Mobile Phase: | Hexane/Ethanol/Methanol/Diethylamine (98:0.5:1.5:0.1) |
| Flow Rate: | 0.7 mL/min |
| Detection: | UV 220 nm |
| Temperature: | Ambient |

Figure 41:
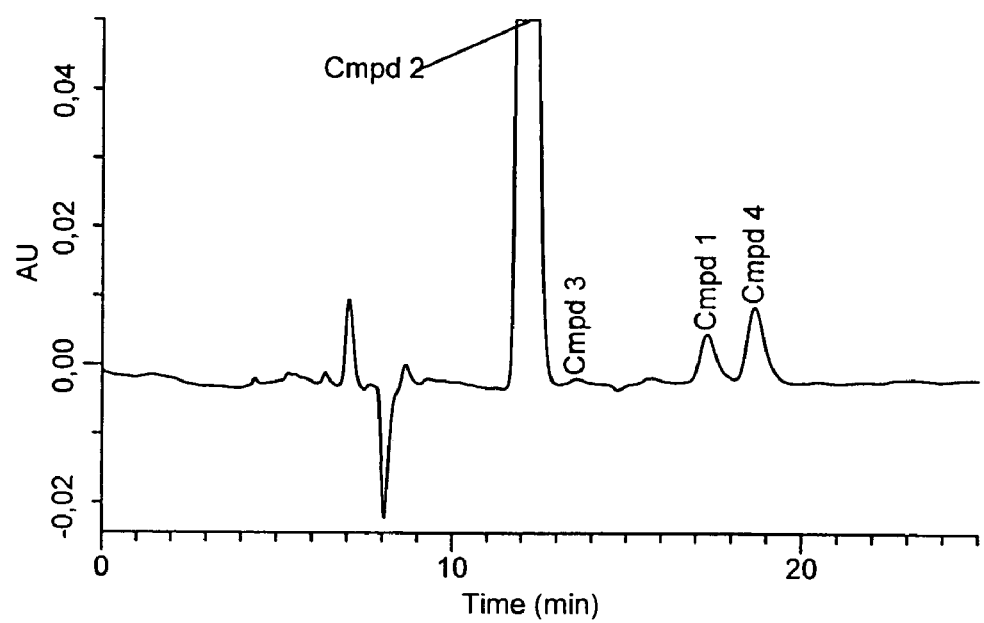
FIG. 41 depicts the HPLC chromatogram of purified stereoisomer 2 (R,S).

Identification of each peak was made by comparison authentic samples of each isomer of N-[1-(1-phenethyl-piperidin-3-yl)-ethyl]-N-phenyl-propionamide (24). This chiral HPLC method was used to analyze 2 obtained from Example 39. See FIG. 41. Using peak area normalization to quantitate the amounts of individual isomers in this sample, the following results were obtained for the sample.

| Sample | %2 (R,S) | %3 (S,R) | %1 (R,R) | %4 (S,S) | % de major isomer | % ee major isomer |
|---|---|---|---|---|---|---|
| Example 39 | 95.46 | 0.14 | 1.67 | 2.73 | 91.2% | 99.7% |

EXAMPLE 41

Achiral (Reverse-phase) HPLC Analysis of 15 (See FIG. 16)

FIG. 16 depicts a series of HPLC analyses (at both 254 and 220 nm) of compound 15 (8.42 mm) alone in the first two analyses, compound 15 co-injected with a mixture of compounds 15 and 16 in the $3^{rd}$ and $4^{th}$ analyses, and of a mixture of compounds 15 and 16 in the $5^{th}$ and $6^{th}$ analyses. The peak at 8.78 mm. is an impurity.

EXAMPLE 42

Achiral (Reverse-phase) HPLC Analysis of 16 (See FIG. 17)

FIG. 17 depicts a series of HPLC analyses (at both 254 and 220 nm) of compound 16 (8.16 mm) alone in the first two analyses, compound 16 co-injected with a mixture of compounds 15 and 16 in the $3^{rd}$ and $4^{th}$ analyses, and of a mixture of compounds 15 and 16 in the $5^{th}$ and $6^{th}$ analyses.

EXAMPLE 43

Achiral (Reverse-phase) HPLC Analyses of 15 and 16 (See FIG. 18)

FIG. 18 depicts a series of HPLC analyses (at both 254 and 220 nm) of compound 15 (8.42 mm) alone in the first two analyses, compound 15 co-injected with compound 16 in the $3^{rd}$ and $4^{th}$ analyses, and compound 16 in the $5^{th}$ and $6^{th}$ analyses.

EXAMPLE 44

Figure 19:
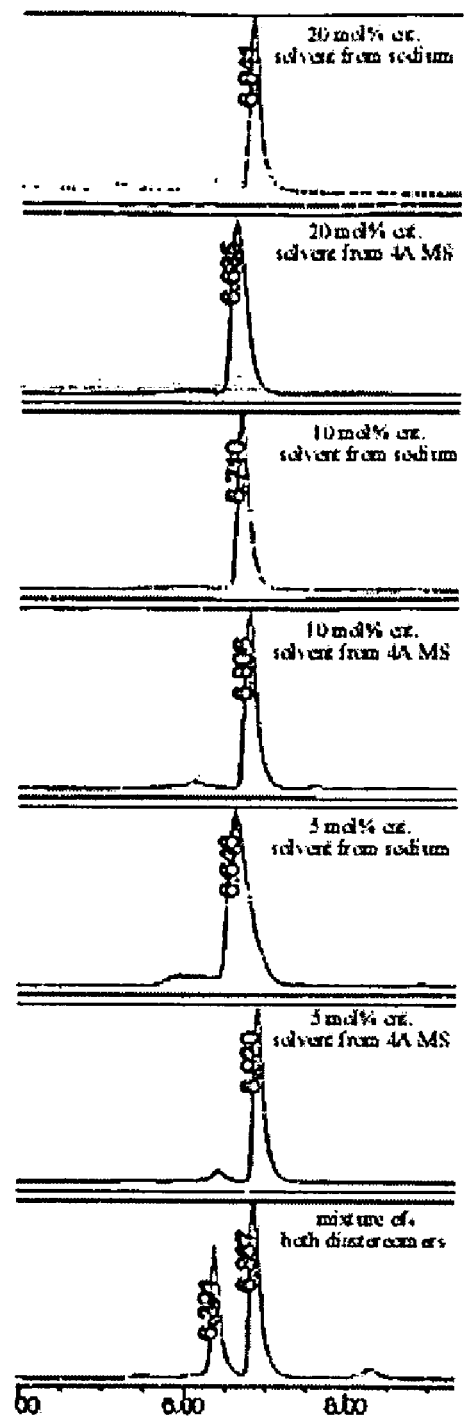
FIG. 19 depicts HPLC traces for various mixtures comprising a compound prepared according to the methods of the present invention.
Figure 21:
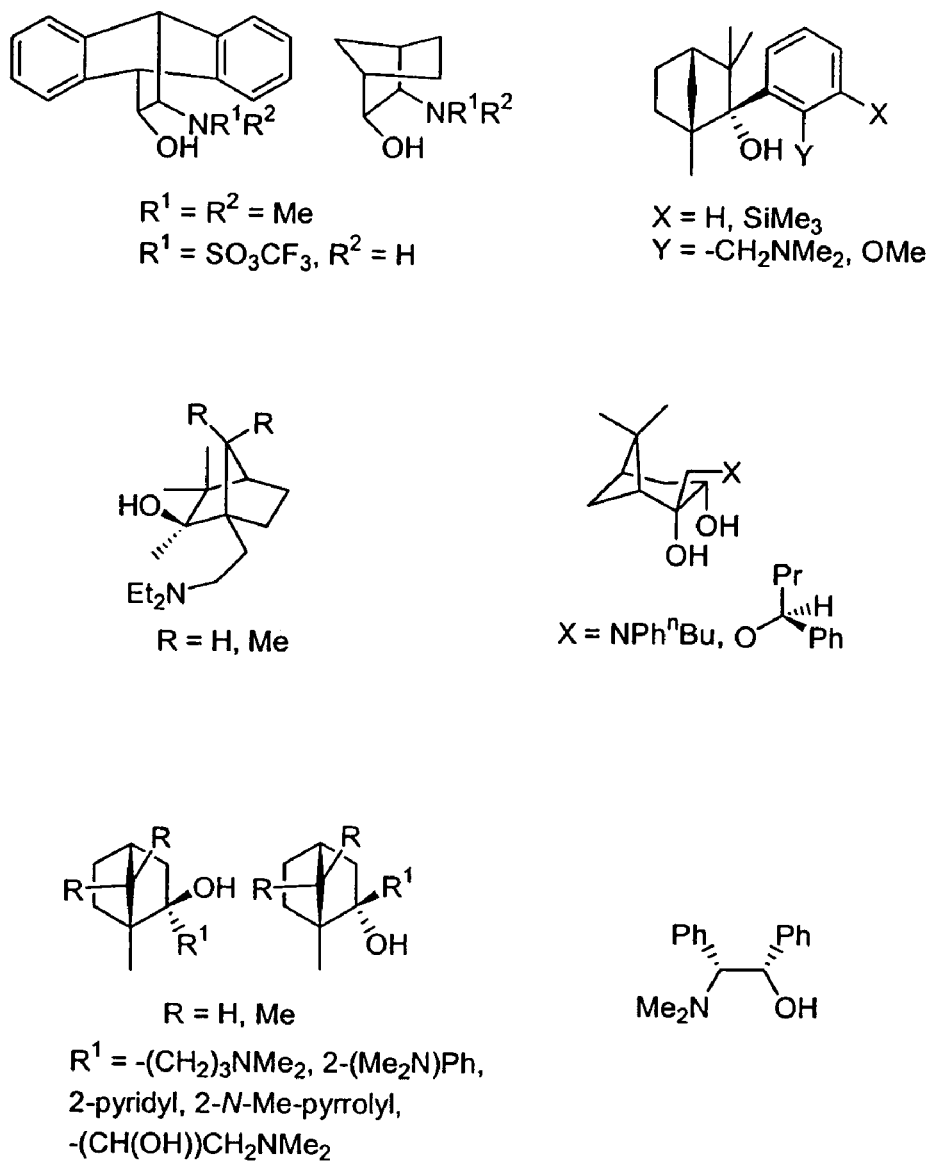
FIG. 21 depicts various asymmetric ligands that may be comprised by the asymmetric catalysts utilized in the asymmetric synthetic methods of the present invention.
Figure 22:
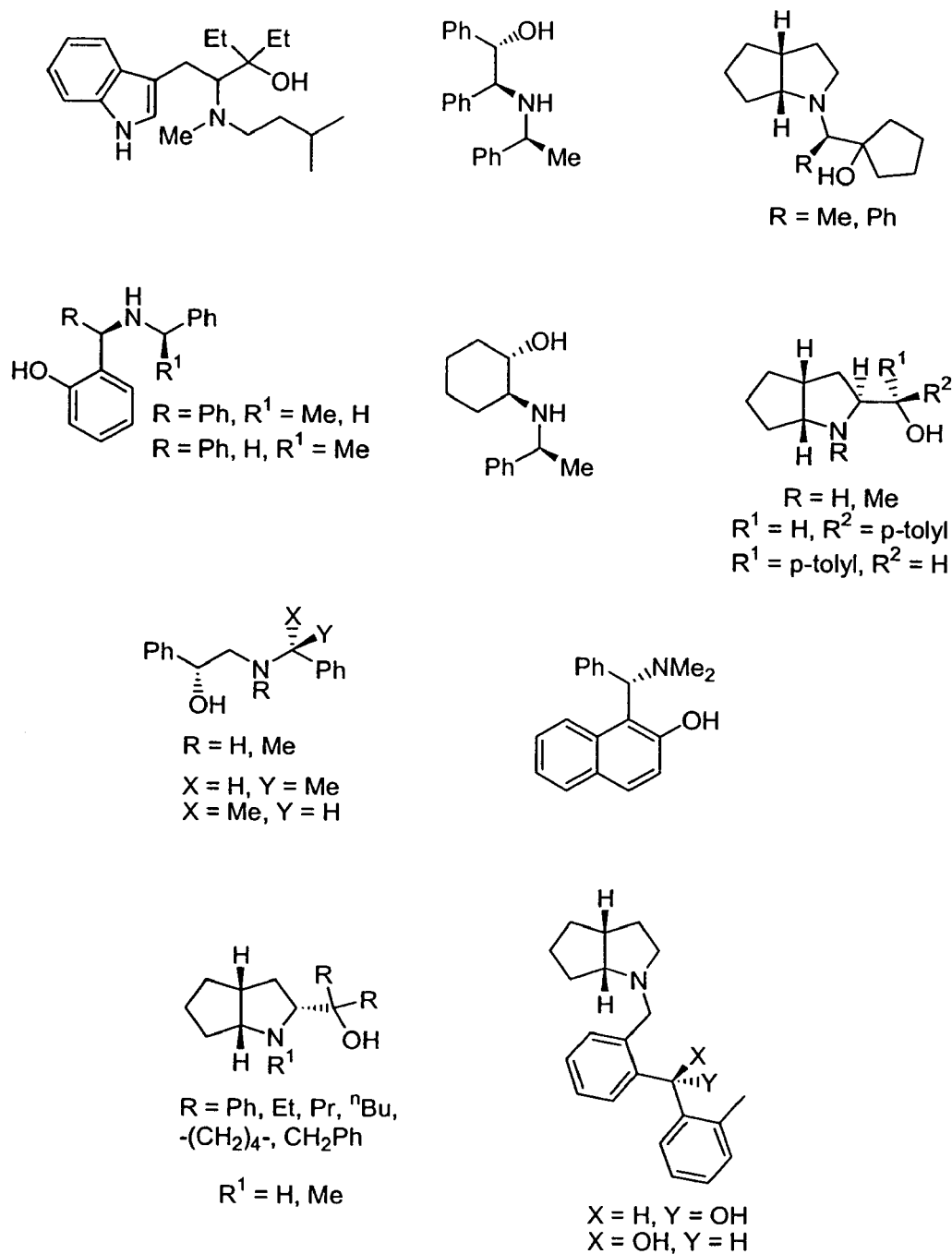
FIG. 22 depicts various asymmetric ligands that may be comprised by the asymmetric catalysts utilized in the asymmetric synthetic methods of the present invention.
Figure 24:
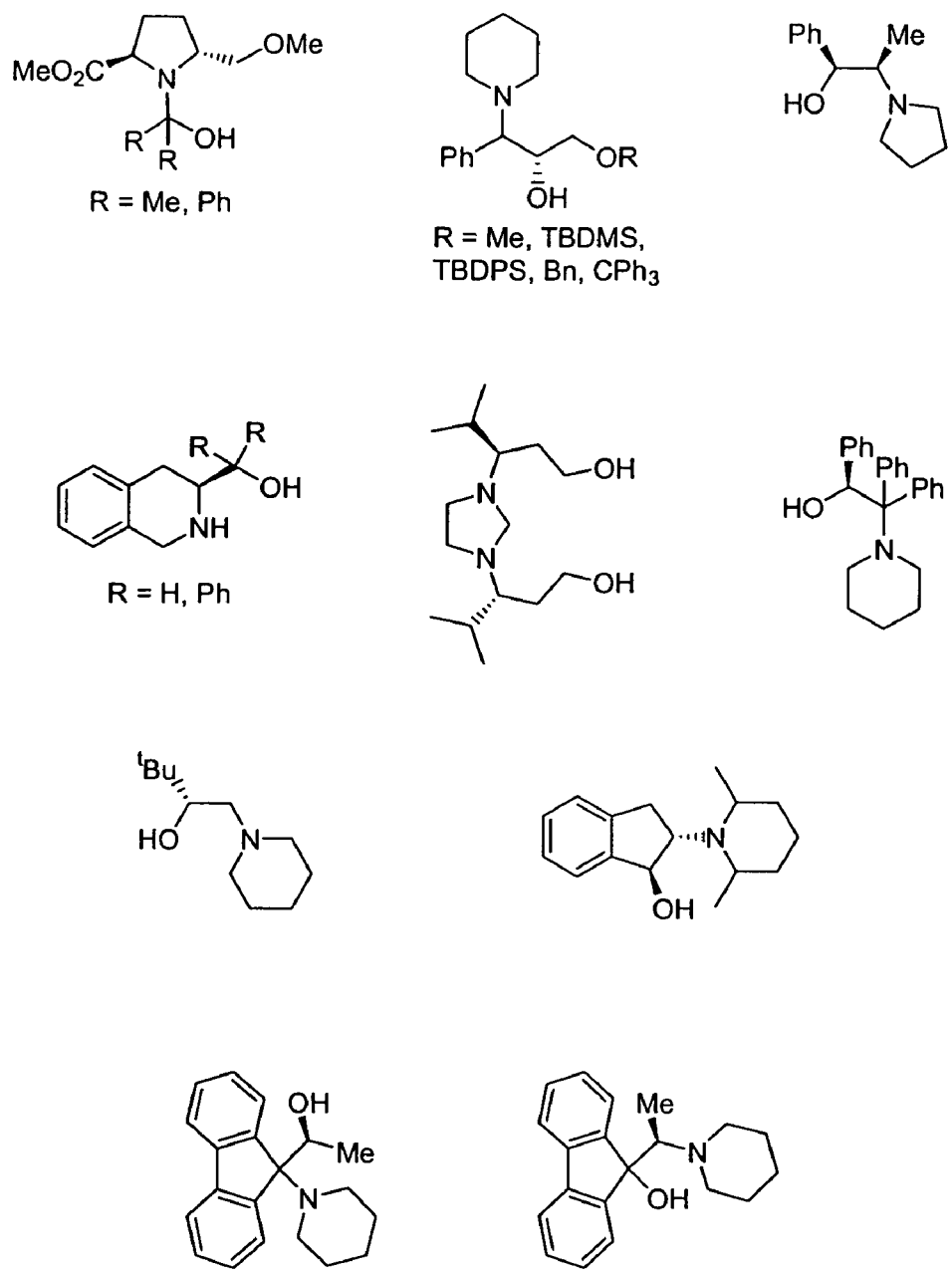
FIG. 24 depicts various asymmetric ligands that may be comprised by the asymmetric catalysts utilized in the asymmetric synthetic methods of the present invention.
Figure 26:
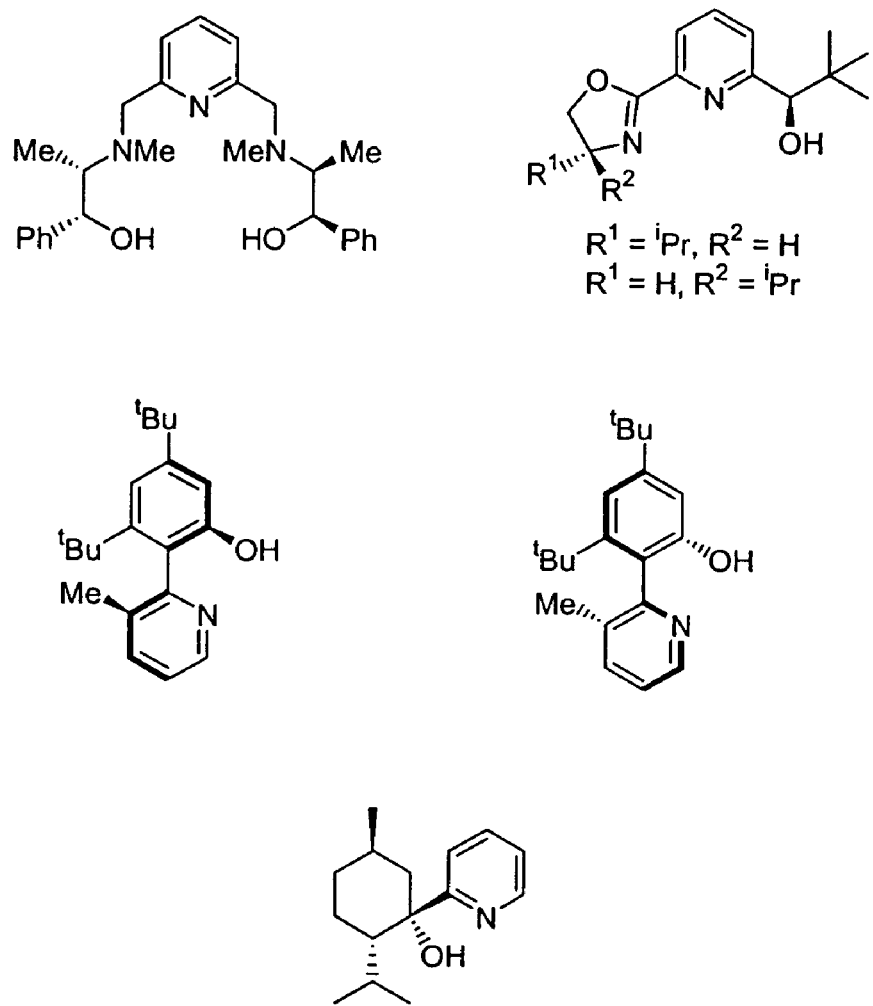
FIG. 26 depicts various asymmetric ligands that may be comprised by the asymmetric catalysts utilized in the asymmetric synthetic methods of the present invention.
Figure 27:
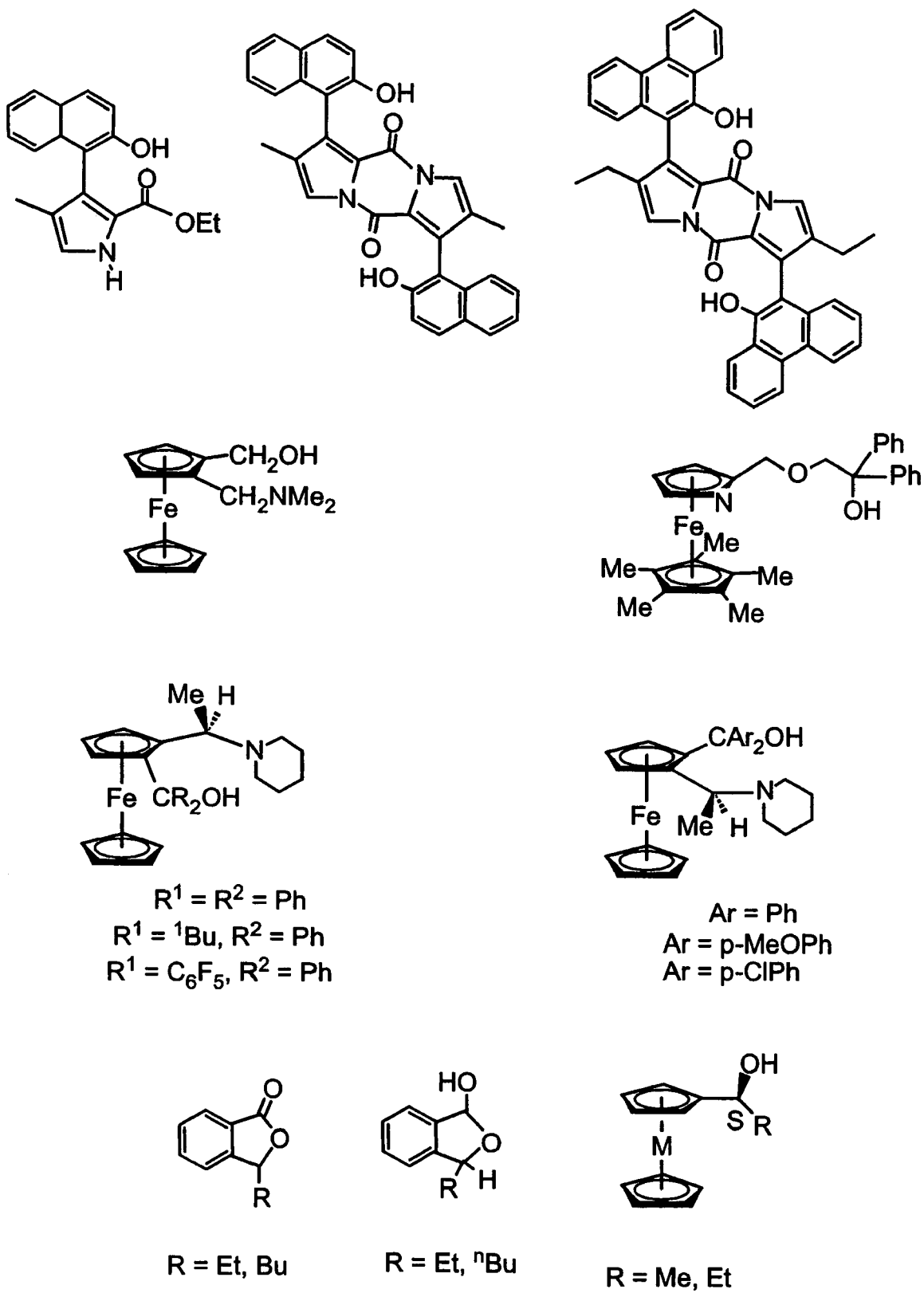
FIG. 27 depicts various asymmetric ligands that may be comprised by the asymmetric catalysts utilized in the asymmetric synthetic methods of the present invention.
Figure 28:
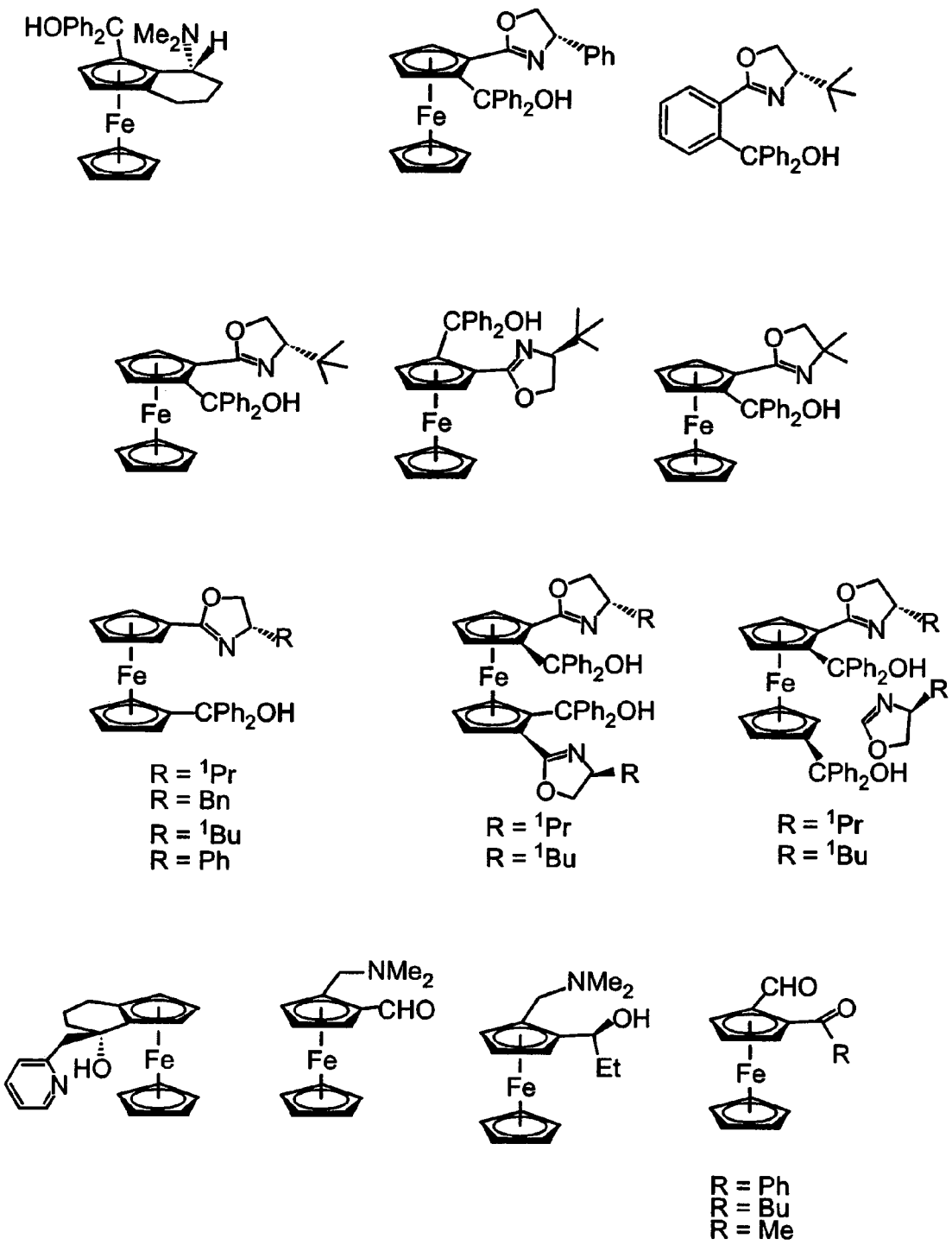
FIG. 28 depicts various asymmetric ligands that may be comprised by the asymmetric catalysts utilized in the asymmetric synthetic methods of the present invention.
Figure 30:
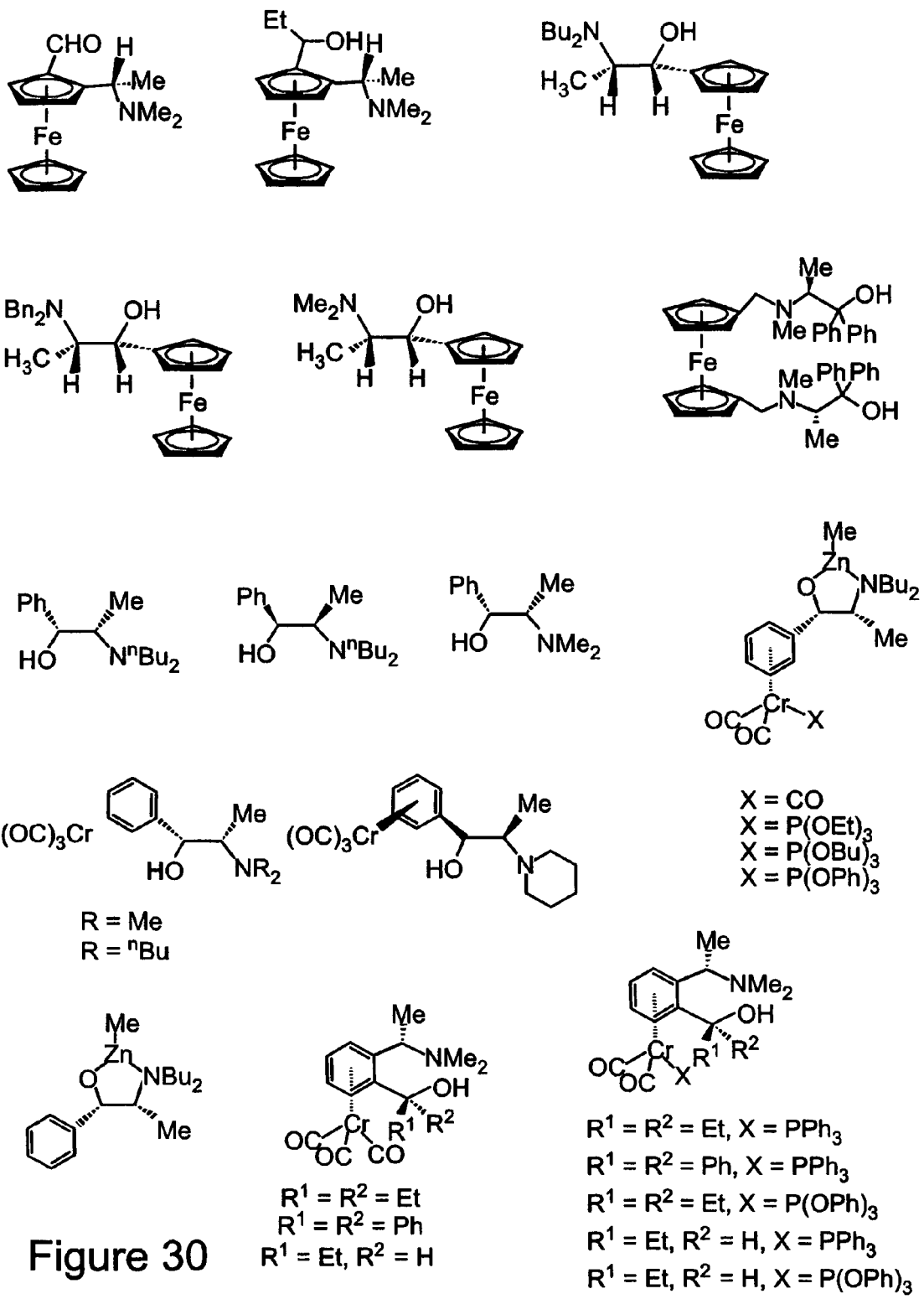
FIG. 30 depicts various asymmetric ligands that may be comprised by the asymmetric catalysts utilized in the asymmetric synthetic methods of the present invention.
Figure 34:
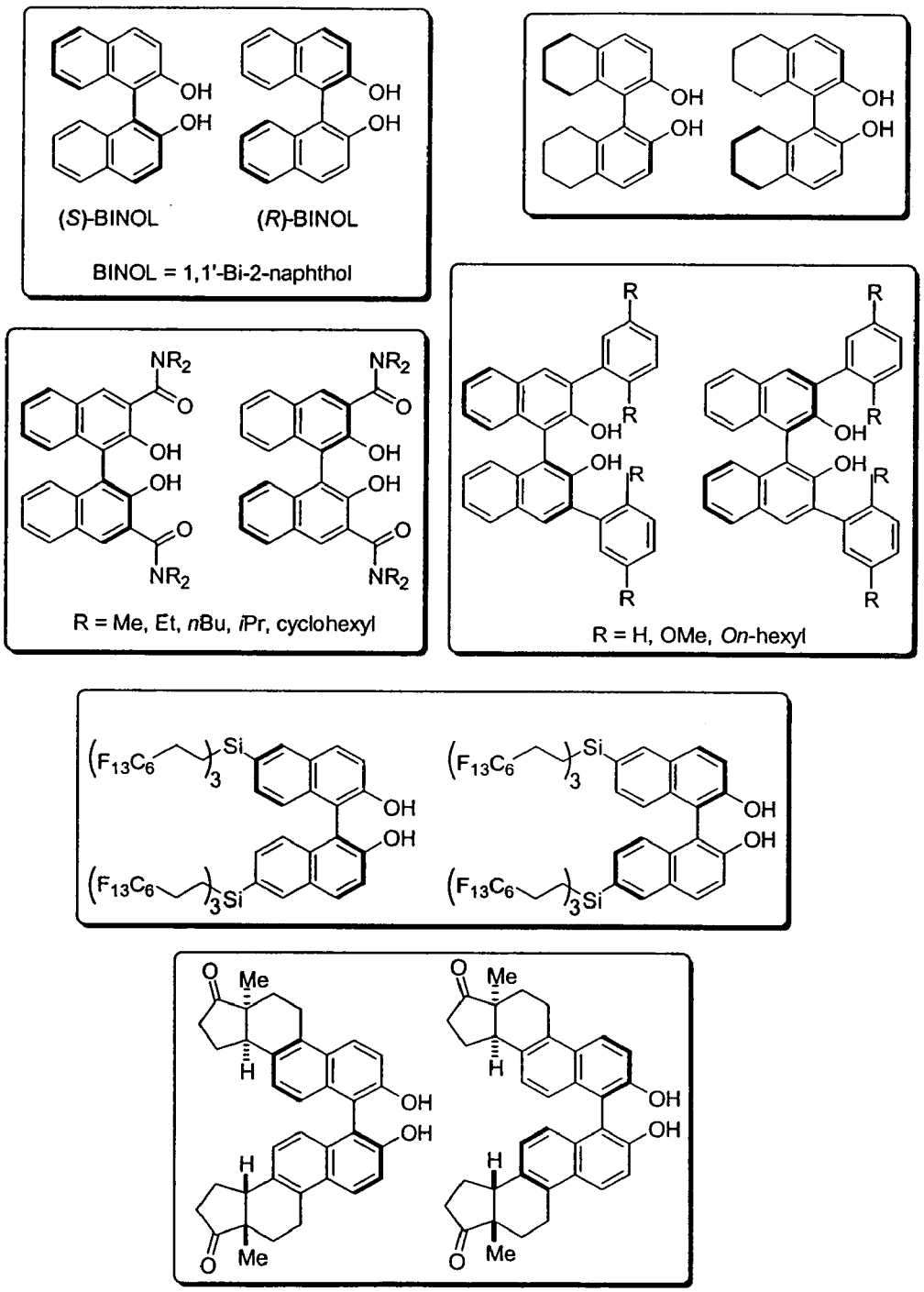
FIG. 34 depicts various asymmetric ligands that may be comprised by the asymmetric catalysts utilized in the asymmetric synthetic methods of the present invention.
Figure 35:
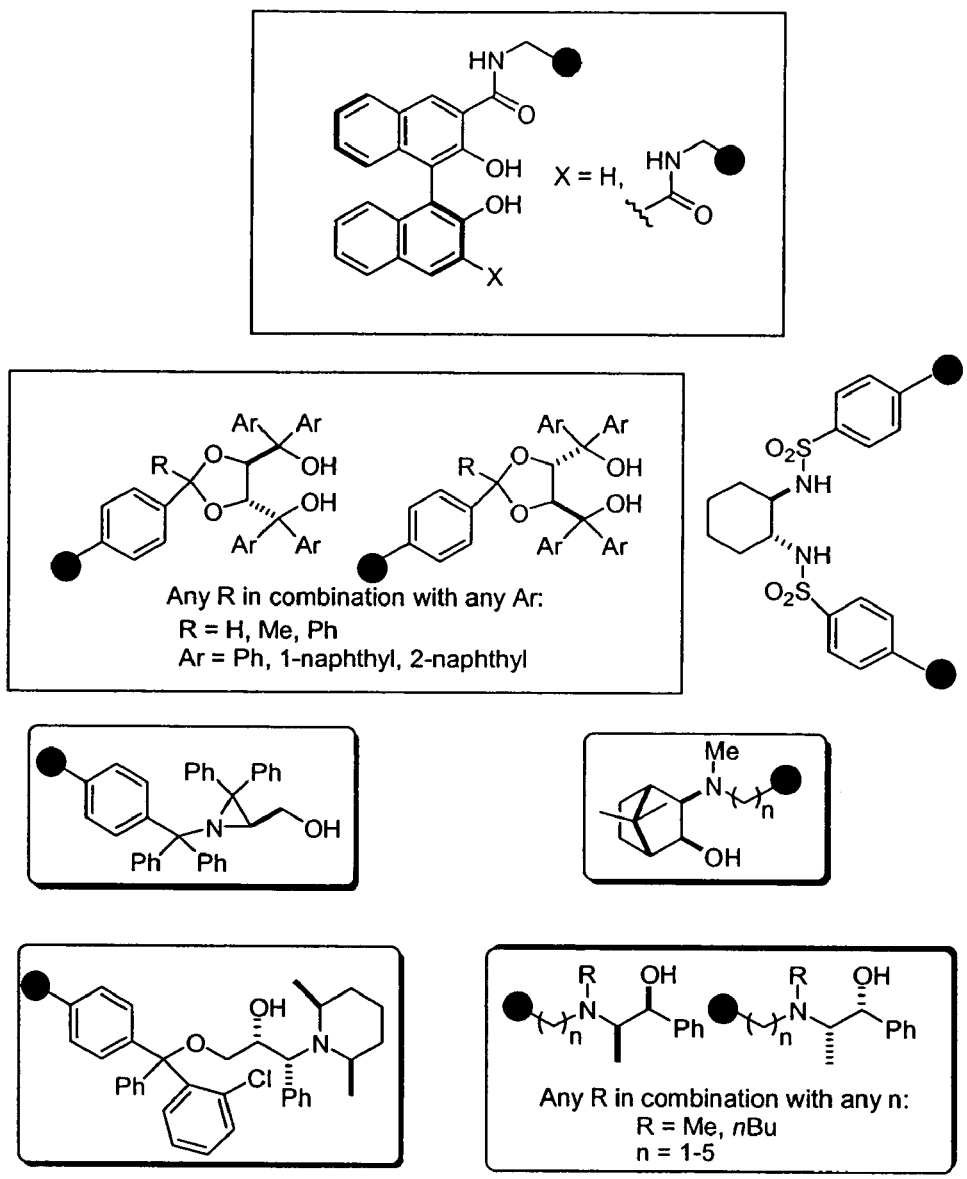
FIG. 35 depicts various asymmetric ligands that may be comprised by the asymmetric catalysts utilized in the asymmetric synthetic methods of the present invention.
Figure 36:
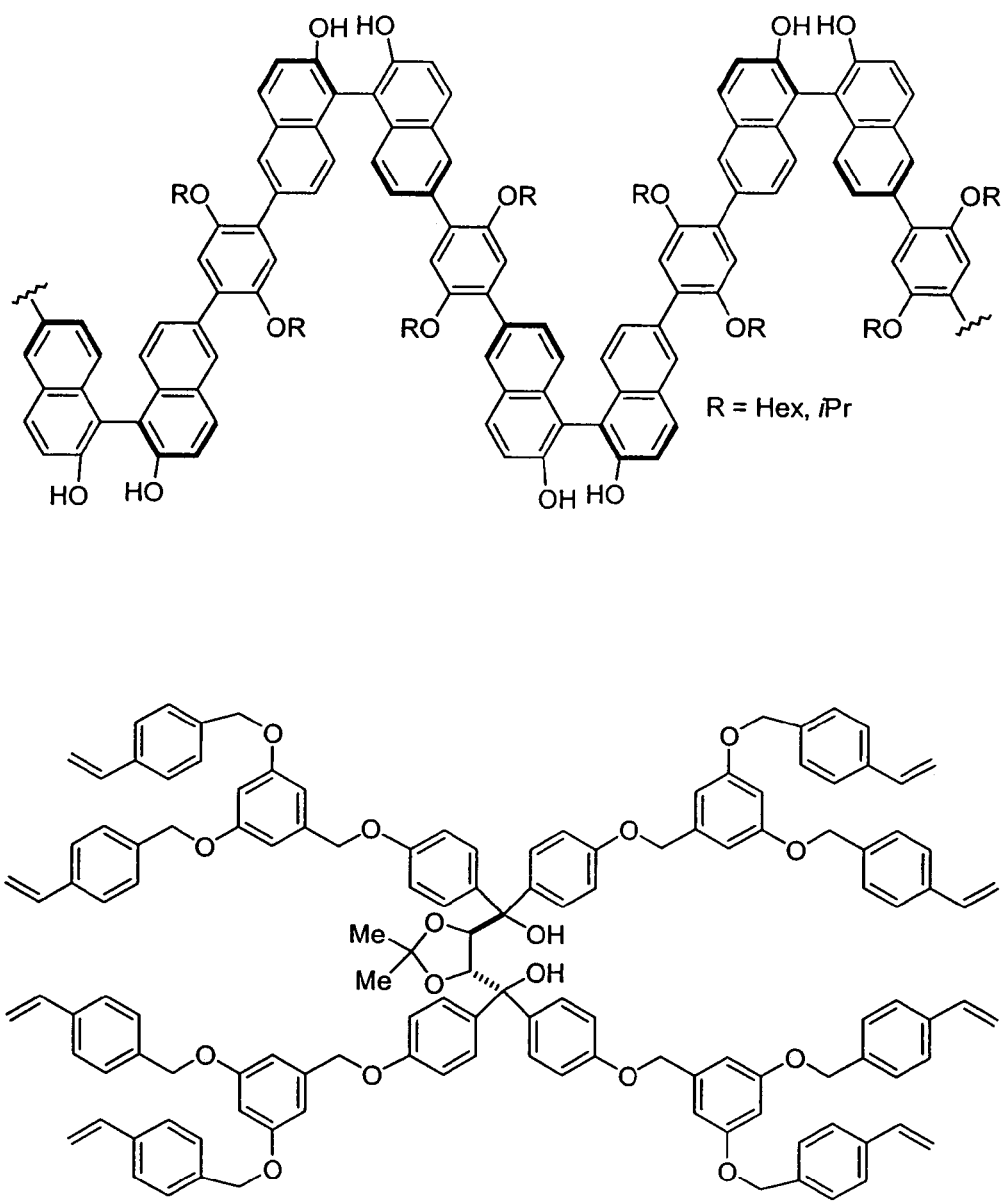
FIG. 36 depicts various asymmetric ligands that may be comprised by the asymmetric catalysts utilized in the asymmetric synthetic methods of the present invention.

Achiral (Reverse-phase) HPLC Analyses of 15 Under a Variety of Reaction Conditions (See FIG. 19)

FIG. 19 depicts a series of HPLC analyses (at 254 nm) of compound 15 (8.8 min) obtained from a variety of experiments run simultaneously and with differing conditions for each reaction. The first two plots are with 20 mol % of catalyst 13. The first reaction used solvents distilled from sodium/benzophenone under argon, and the second used solvents purchased anhydrous from Aldrich and dried with activated 4 Å molecular sieves. The $3^{rd}$ and $4^{th}$ plots are with 10 mol % of catalyst 13. The $3^{rd}$ reaction used solvent distilled from sodium/benzophenone under argon, and the $4^{th}$ experiment used anhydrous solvents pre-dried with activated 4 Å molecular sieves. The $5^{th}$ and $6^{th}$ plots are for experiments which used 5 mol % of catalyst 13. The $5^{th}$ reaction used solvent distilled from sodium/benzophenone under argon, and the $6^{th}$ experiment used anhydrous solvents pre-dried with activated 4 Å molecular sieves. The $7^{th}$ plot is a co-injection of compound 15 obtained from the first reaction (plot 1) with 16 (8.3 min).

EXAMPLE 45

Opiate Receptor Binding of Certain Enantiomerically Pure 3-Substituted Piperidines ($IC_{50}$s)

The opioid ($\mu$, $\kappa$, $\delta$) receptor-binding capabilities of compounds prepared using the methods of the present invention were determined according to the procedures outlined by Wang et al. (*FEBS Letters* 1994, 338, 217), Maguire et al. (*Eur. J. Pharmacol.* 1992, 213, 219), and Simonin et al. (*Mol. Pharmacol.* 1994, 46, 1015). Certain results from these assays are tabulated below.

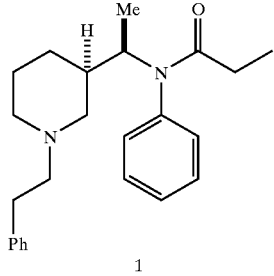

1

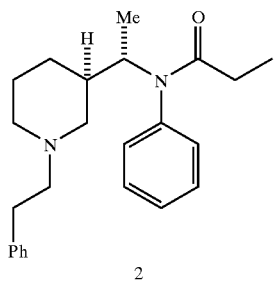

2

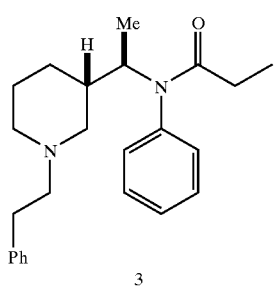

3

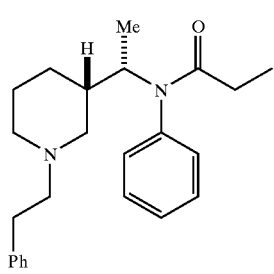

4

| Compound | μ (μM) | κ (μM) | δ (μM) |
|---|---|---|---|
| 1 | <1 | <1 | <10 |
| 2 | <1 | <5 | >10 |
| 3 | <1 | <5 | >10 |
| 4 | <1 | <1 | >10 |

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A compound of formula I:

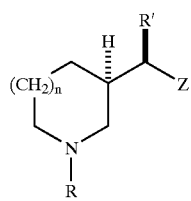

wherein
n is 1;
R is aralkyl;
R' is alkyl;
Z is NHR"; and
R" is unsubstituted aryl.

2. The compound of claim 1, wherein R is —CH$_2$CH$_2$Ph.
3. The compound of claim 1, wherein R' is methyl.
4. The compound of claim 1, wherein R" is phenyl.
5. The compound of claim 1, wherein R' is Me; and R" is phenyl.
6. The compound of claim 1, wherein R is —CH$_2$CH$_2$Ph; and R' is methyl.
7. The compound of claim 1, wherein R is —CH$_2$CH$_2$Ph; R' is methyl; and R" is phenyl.
8. A compound of formula II:

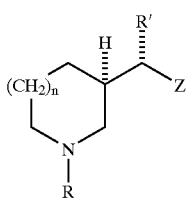

wherein
n is 1;
R is aralkyl;
R' is alkyl;
Z is NHR"; and
R" is unsubstituted aryl.

9. The compound of claim 8, wherein R is —CH$_2$CH$_2$Ph.
10. The compound of claim 8, wherein R' is methyl.
11. The compound of claim 8, wherein R" is phenyl.
12. The compound of claim 8, wherein R' is Me; and R" is phenyl.
13. The compound of claim 8, wherein R is —CH$_2$CH$_2$Ph; and R' is methyl.
14. The compound of claim 8, wherein R is —CH$_2$CH$_2$Ph; R' is methyl; and R" is phenyl.

15. A compound of formula III:

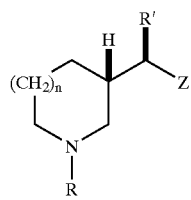

wherein
- n is 1;
- R is aralkyl;
- R' is alkyl;
- Z is NHR"; and
- R" is unsubstituted aryl.

16. The compound of claim 15, wherein R is —$CH_2CH_2Ph$.

17. The compound of claim 15, wherein R' is methyl.

18. The compound of claim 15, wherein Z is R" is phenyl.

19. The compound of claim 15, wherein R' is Me; and R" is phenyl.

20. The compound of claim 15, wherein R is —$CH_2CH_2Ph$; and R' is methyl.

21. The compound of claim 15, wherein R is —$CH_2CH_2Ph$; R' is methyl; and R" is phenyl.

22. A compound of formula IV:

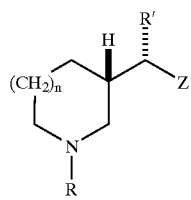

wherein
- n is 1;
- R is aralkyl;
- R' is alkyl;
- Z is NHR"; and
- R" is unsubstituted aryl.

23. The compound of claim 22, wherein R is —$CH_2CH_2Ph$.

24. The compound of claim 22, wherein R' is methyl.

25. The compound of claim 22, wherein R" is phenyl.

26. The compound of claim 22, wherein R' is Me; and R" is phenyl.

27. The compound of claim 22, wherein R is —$CH_2CH_2Ph$; and R' is methyl.

28. The compound of claim 22, wherein R is —$CH_2CH_2Ph$; R' is methyl; and R" is phenyl.

* * * * *